United States Patent
DeBernardis et al.

(10) Patent No.: US 10,004,403 B2
(45) Date of Patent: Jun. 26, 2018

(54) THREE DIMENSIONAL TISSUE IMAGING SYSTEM AND METHOD

(71) Applicants: Frank A. DeBernardis, Ridgewood, NJ (US); Natalie J. Tucker, New York, NY (US); Austin D. Reiter, Great Neck, NY (US); Minhaz Palasara, New York, NY (US)

(72) Inventors: Frank A. DeBernardis, Ridgewood, NJ (US); Natalie J. Tucker, New York, NY (US); Austin D. Reiter, Great Neck, NY (US); Minhaz Palasara, New York, NY (US)

(73) Assignee: Mela Sciences, Inc., Irvington, NY (US)

( * ) Notice: Subject to any disclaimer, the term of this patent is extended or adjusted under 35 U.S.C. 154(b) by 74 days.

(21) Appl. No.: 14/837,120

(22) Filed: Aug. 27, 2015

(65) Prior Publication Data

US 2016/0058288 A1 Mar. 3, 2016

Related U.S. Application Data

(60) Provisional application No. 62/042,858, filed on Aug. 28, 2014.

(51) Int. Cl.
*A61B 5/00* (2006.01)
*G06T 17/10* (2006.01)

(52) U.S. Cl.
CPC .......... *A61B 5/0077* (2013.01); *A61B 5/0075* (2013.01); *A61B 5/444* (2013.01); *G06T 17/10* (2013.01); *A61B 5/742* (2013.01); *A61B 5/748* (2013.01); *A61B 2560/0475* (2013.01); *G06T 2210/41* (2013.01)

(58) Field of Classification Search
CPC ..... A61B 5/0077; A61B 5/0075; A61B 5/444; A61B 5/742; A61B 5/748; A61B 2560/0475; G06T 17/10; G06T 2210/41
See application file for complete search history.

(56) References Cited

U.S. PATENT DOCUMENTS

| | | | |
|---|---|---|---|
| 6,081,612 A * | 6/2000 | Gutkowicz-Krusin | A61B 5/0071 382/128 |
| 6,208,749 B1 * | 3/2001 | Gutkowicz-Krusin | 356/303 |
| 7,747,055 B1 * | 6/2010 | Vining | A61B 6/466 345/419 |

(Continued)

OTHER PUBLICATIONS

PCT Search Report, dated Nov. 24, 2015, pp. 1-8, US.

*Primary Examiner* — Catherine Voorhees
(74) *Attorney, Agent, or Firm* — Carter Ledyard & Milburn LLP

(57) ABSTRACT

Multispectral digitized images are provided by utilizing 2 or more spectral bands, providing images and information regarding a pigmented or other differentiated tissue sample at differing depths. The images are transformed to enhance morphological patterns characteristic of melanoma, such as the statistical properties of the pigment network, image texture or homogeneity, and the lesion reflectance, in order to provide information about lesion morphology at different depths. The images can also be processed and transformed to extract features such as blood volume saturation, oxygen saturation, or other characteristics that can be identified based on differential reflectance or absorption of light.

12 Claims, 18 Drawing Sheets

(56) References Cited

U.S. PATENT DOCUMENTS

| | | | |
|---|---|---|---|
| 7,978,346 B1 | 7/2011 | Riza | |
| 2001/0039422 A1* | 11/2001 | Carol | A61B 90/10 606/130 |
| 2010/0042004 A1* | 2/2010 | Dhawan | A61B 5/0059 600/476 |
| 2011/0304705 A1* | 12/2011 | Kantor | A61B 5/0059 348/49 |
| 2012/0130232 A1* | 5/2012 | Markowitz | A61B 5/0422 600/424 |
| 2014/0049614 A1* | 2/2014 | Yamada | H04N 5/2226 348/46 |

\* cited by examiner

THREE DIMENSIONAL TISSUE IMAGING SYSTEM AND METHOD

CROSS-REFERENCE TO RELATED APPLICATIONS

This application is related to, and claims the benefit of, U.S. Provisional Patent Application Ser. No. 62/042,858, filed Aug. 28, 2014, which is incorporated herein by reference.

FIELD OF THE INVENTION

The present invention relates to systems and methods for optical spectral imaging of tissue in three dimensions using multiple spectrums of light.

BACKGROUND OF THE INVENTION

Conventionally, lesion information is obtained via surface visual analysis by the dermatologist. This limited information results in 20-30% of early melanomas going undetected. The estimated total direct cost associated with the treatment of melanoma in 2010 in the United States due to lack of early detection was $2.36 billion, with 65% of total cost going to continued care and another 20% of total cost going to the last year of life.

To see below the topmost layer of skin, a dermatoscope with a lighted magnifier may be used, but the image is limited to the top few layers of the surface of the skin. Additional imaging tools are available to the market, but none display or quantify the morphological disorganization characteristics as obtained from below the surface of the skin.

In the field of surgery and dermatology, lesion volume and location of disorganized tissue is critical in determining that the proper area is removed through biopsy for subsequent review by the pathologist. Current teaching techniques recommend utilizing a dermatoscope to select sampling location for biopsy. In a study by Dr. Hsu and Dr. Cockerell, 1123 histologically confirmed melanomas were reviewed and found significant diagnostic discrepancy between initial punch biopsies and re-excision specimens. While the excisional biopsy and sauceration shave biopsy demonstrated near 100% accuracy, punch technique was only 86.5% accurate. The paper reveals, "Due to the inherent intralesional heterogeneity of cutaneous melanoma, small punch biopsies may not always obtain representative specimens and may subject the patient to significant risk of misdiagnosis."

Further misdiagnosis occurs among pathologists who either over diagnose or under diagnose a lesion. This is represented in a number of papers where discordance in dermatopathology among reviewers has been reported ranging from 14.3%-62.0%. As a result, typically only 2-5% of the total lesion is examined by the pathologist, and the remaining tissue sample is archived or discarded. This technique results in additional sections being ordered by the dermatologist if he or she believes the diagnosis is not correct, and perhaps the area of interest was not reviewed by the pathologist due to ineffective sectioning. Currently, no imaging device is known that offers the capability to guide sectioning as performed by a pathologist and his or her grossers, and this lack of image guidance in determining which areas of the lesion to section, in addition to subjective evaluation under the microscope, puts patients at undue risk.

For surgeons, ultrasound is the only medium for imaging a lesion below the skin in an attempt to view total volume. Unfortunately, ultrasound is unreliable on pigmented lesions and is difficult to read.

Recently, the MelaFind® Optical Imaging and Analysis Device has become available following FDA approval. It is a multispectral digital skin lesion analysis system used in the detection of melanoma among atypical skin lesions. The device uses light to image the skin through a layer of isopropyl alcohol to generate a classifier score result that provides information on the likelihood of a lesion being melanoma based on predefined image analysis algorithms. The device is used when a dermatologist chooses to obtain additional information on a decision to biopsy.

The MelaFind device currently utilizes multispectral images from 10 wavelengths of light, 430 nm to 950 nm, and produces colorless melanin absorption based images utilizing 10 spectral bands. These images however are not transformed into a 3-dimensional volumetric rendering of the lesion, and require interpretation by the user on the areas between each vertical layer image. The operation of some aspects of the MelaFind device are disclosed in U.S. Pat. Nos. 6,081,612 and 6,208,749, which are hereby incorporated by reference in this application in their entirety.

SUMMARY OF THE INVENTION

Multispectral digitized images are provided by utilizing 2 or more spectral bands, providing images and information regarding a pigmented or other differentiated tissue sample at differing depths. The penetration depth into an object for different bands is based on the fact that the longer the wavelength of light, the deeper the light penetrates tissue.

The images are transformed to enhance morphological patterns characteristic of melanoma, such as the statistical properties of the pigment network, image texture or homogeneity, and the lesion reflectance, in order to provide information about lesion morphology at different depths. The images can also be processed and transformed to extract features such as blood volume saturation, oxygen saturation, or other characteristics that can be identified based on differential reflectance or absorption of light.

The 2D mesh images obtained at each wavelength are then used to create 3D representations of a tissue sample through voxels. The 2D mesh images can be turned into a 3D voxel representation and vice versa. Area and volume calculations on these representations can be provided as guidance for excision or for visualizing specific areas of disorganization or other desired features or characteristics within a 3-dimensional tissue sample.

One possible indication for use of the 3D Optical Spectral Imaging technology disclosed herein may be for Image Guided Tissue Sampling, the intent of which is to sample the most disorganized area of the lesion, thus reducing sampling error. A second possible indication for use of the Optical Spectral Imaging technology may be for Image Guided Tissue Sectioning for dermatopathologists, the intent of which is to select the most disorganized area of the lesion to be used for evaluation by the pathologist under the microscope. A third possible indication for use of the Optical Spectral Imaging technology may be for Image Guided Biopsies, the intent of which is to increase surgery efficiency by viewing the 3-dimensional volume and construct of the lesion for margin guidance. As a result, the present invention is intended to improve the standard of care for biopsies, increase dermatopathology sectioning efficiency and accuracy, as well as aid in the surgeon's excision quality of removed tissue.

Other applications may be in guiding surgeons and interventionists in the evaluation of other tissue constructs. Interventional cardiologists may benefit from examining vessel wall tissue organization as well as myocardial wall cell construct. General surgeons may benefit from using the technology to examine tissue in exploratory procedures.

Further indications are set forth below.

DETAILED DESCRIPTION

Overview

Figure 1:
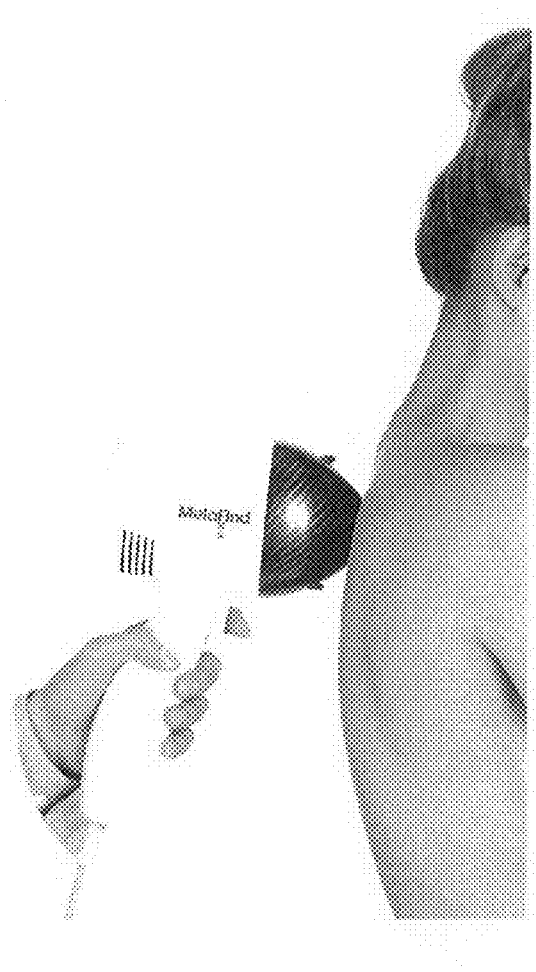
FIG. 1, also referred to as Image 1, illustrates the MelaFind optical scanner being held by a medical professional or technician against a region of interest on the back of a patient.

Medical diagnostic imaging is performed to acquire data about the state of human body parts, including internal organs as well as skin, which is an external organ. In the case of skin, the imaging with visible and near infrared light can be performed in vivo or in vitro to a depth of approximately 2.5 millimeters. In the current invention of Optical Spectral Imaging ("OSI"), the data acquired through this multispectral imaging is processed and analyzed to derive metrics of small volume elements ("voxels") to a depth of approximately 2.5 millimeters, and to provide three dimensional ("3D") representations thereof. Such imaging information can provide metrics and conclusions about the tissue being examined. OSI may assist in improving discordance levels among pathologists by communicating the area of interest to the pathologist to target while sectioning and diagnosing the lesion, with additional sections being reviewed for high-risk lesions or as deemed necessary by the dermatologist.

The system initially yields 10 images, each resulting from a different wavelength and located at an estimated perpendicular depth from the optical center of the camera. Each image contains a slightly more submersed (from the surface of the skin) image of a lesion than the previous. The algorithm employed begins with an image segmentation procedure which automatically identifies which pixels belong to the lesion (and which pixels belong to the background, or normal tissue) at each depth slice, or image layer, of the system. Since the shape of the lesion will change, however slightly, as you move further into the skin, accurate image segmentation is essential to properly capturing the shape of the lesion in 3D. The segmentation procedure yields formation of binary images at each depth slice, meaning an image comprising pixels that can have only 1 of 2 values: 255 if it is part of the lesion, and 0 otherwise. Each pixel location is also defined in terms of 3D spacing because of the known camera calibration of the system, and so 20 microns of separation can be assumed pixel-to-pixel. Using the estimated depth values of each slice, the binary images are transformed into a 3D point cloud using only information from the marked pixels, the pixel spacing (20 micron spacing), and the estimated optical depth distance as the z-coordinates.

To produce a smoother 3D representation, further 3D points are interpolated from the known 3D points in the point cloud using bilinear interpolation. Finally, a voxel reconstruction algorithm grids the 3D space into an even spacing of voxels at a known size, and by voting, each voxel is filled (or left empty) with a known color value which may come from various sources, such as the original imagery or any technical information, such as "texture" or melatonin. This allows for representation of the lesion in 3D with a smooth surface and for filling-in the internals of the lesion with the known color information from the imagery. Then, one can rotate, zoom, and even look inside the 3D lesion with the interpolated volume. Additionally, one may also (possibly) extrapolate 2D images at depths that the MelaFind system did not originally capture by back-projecting the 3D volume into the camera at various depths and interpolating the color values.

Optical Spectral Imaging can be presented to the user in a format via a computer user interface that allows user interaction and manipulation with any selected area of a 3-dimensional image in order to view and quantify targeted features. The user may select the area of interest and quantify information as generated by OSI. Different characteristics can be targeted by the user and a variety of outputs can be selected and manipulated. OSI assigns color codes to quantified algorithmic values as sourced from multispectral images in order to communicate to the user the level of disorganization or other features as imaged by multispectral imaging and transformed into OSI. The visual communication platform through the user interface allows the user to drive the operation and determine his/her area of interest in order to quantify such imaging information.

Users in different locations can share the OSI data and information. For example, the diagnostic imaging can be performed by a user at one location, while the acquired data can be analyzed by another user (or a machine of another user) at a different location.

First Example Implementation

Obtaining Multi-Spectral Images

The inventive system first obtains multi-spectral images. This can be achieved using the hardware and some of the software used with the MelaFind computer-controlled multi-spectral imaging and analysis system, in which ten distinct spectral bands are used to illuminate a skin lesion with wavelengths distributed over visible to near-infrared ranges, from 430 nm (blue) through 950 nm (near infrared spectrum). Appendix Image 1 illustrates the MelaFind optical scanner being held by a medical professional or technician against a region of interest on the back of a patient. Appendix Image 2 shows the wavelengths used to obtain data from various depths below the surface of the skin and examples of the images that can be created using the existing MelaFind system.

In use, the imaging assembly illuminates the skin with light through a thin layer of alcohol, via an illumination circuit containing light-emitting diodes (i.e. LED) composed to generate ten different wavelengths of light, turned on and off in rapid sequence under computer control. A Complementary Metal Oxide Semiconductor (CMOS) sensor inside the imaging assembly captures the set of ten images. Each of the ten images is labeled with its nominal wavelength of light. An automatically generated "segmentation mask" separates the lesion or other features of interest from the surrounding skin, the operation of which is further described below. The ten-image set is then sent for analysis to the on-board computer. One part of the computer's Operating Systems (OS) software automatically checks the image quality and alerts the user to retake images that are not satisfactory, which may be done as specified in U.S. Pat. Nos. 6,081,612 and 6,208,749.

Segmentation Mask Operation

The segmentation algorithm isolates the pixels in the images which belong to the lesion from those that do not (i.e., all background pixels). In practice, the "lesion" may not be a "lesion" in the medical sense, but for purposes of this invention may be considered any tissue or cell structure of interest that can be differentiated from the surrounding tissue based on characteristics such as blood volume saturation, oxygen saturation, or other characteristics that can be identified based on differential reflectance or absorption of light. The algorithm is a completely automated approach, requiring no user input to isolate the lesion. The segmentation is performed at each of the bands, one-by-one, to best capture the shape of the lesion (rather than only segmenting the top-most band and using that throughout the remaining bands, as was done in the existing MelaFind system). Alternatively, the tissue or cell structure of interest may be differentiated from the surrounding tissue based on characteristics such as blood volume saturation, oxygen saturation, or other characteristics that can be identified based on differential reflectance or absorption of light, as taught by, for example, PCT Application PCT/US11/64723 (filed Dec. 13, 2011), PCT Application PCT/US12/58065 (filed Sep. 28, 2012), PCT Application PCT/US13/71269 (filed Nov. 21, 2013), the contents of which are incorporated by reference in their entireties herein.

In the present system, in one embodiment best adapted to identifying lesions and tissue of interest that is generally centrally located in the images, it is assumed that the top-most ("band 0"), 430 nm image, has the best contrast to distinguish the lesion from the background. This is used to initialize all of the remaining images as follows: in the band-0 image, the system seeks to define a region-of-interest (ROI), defined as a rectangular bounding box, which best encompasses the lesion in the image. This allows for immediate disposal of a majority of the image, as this bounding box will suffice to initialize all other remaining images as the contrast decreases. Once the ROI is determined, the system performs an adaptive histogram thresholding in the remaining images within this ROI to associate each pixel as a foreground lesion pixel or as a background non-lesion pixel. More details on each follow below.

Initializing the Region-of-Interest on Band-0 for Segmentation

In order to find the ROI around the lesion in the first image, the system first performs an Expectation-Maximization (EM) unsupervised clustering of the pixels. Using the gray-scale values from the pixels, or other values determined based on the light absorbing or reflecting or other characteristics of the tissue of interest, all pixels in the entire image are collected into a single matrix dataset. The system then seeks to automatically divide these pixels into two groups: foreground and background, based only on the gray-scale or other values. The idea here is that lesion pixels are usually darker or have higher or lower values than background pixels, but defining what "dark", "higher", or "lower" means across all patients in a global sense is difficult, if not impossible. So instead, the system finds the best separation amongst the pixels on a per-patient basis. The EM algorithm is an iterative method for fitting a statistic model to a dataset by finding the maximum likelihood for the parameters of the statistic model. In this case, the system uses a Gaussian Mixture Model (GMM), seeking to maximize the parameters according to the mean, covariance, and mixture components to the dataset using the EM approach. The mean and covariance of each of the two groups represents the lesion-versus-non-lesion groups. In the end, this EM/GMM method allows the algorithm to assign a class-conditional probability at every pixel, meaning one can assign a probability of being in the lesion class as well as the probability of being in the non-lesion class, at every pixel. If the EM clustering works as designed, the probability at a lesion pixel will yield a higher probability in that group from the GMM than the non-lesion group.

If desired, the ROI can be further refined by attempting to eliminate spurious pixels in the image, which may be due to hairs or other tissue features that are not of interest, which can throw off the ROI estimate. To compensate for this, the system can add a prior probability model, such as a Gaussian weighting kernel, to the EM/GMM model which makes some assumption about the location or shape of the lesion. For example, a melanoma lesion would be roughly centered in the image. This does not need to be exact, and to achieve this prior model, the system constructs a Gaussian weighting function which weights pixels in the center of the image higher than those towards the edges of the image. This, along with the EM/GMM unsupervised clustering, allows the algorithm to select and divide pixels and eliminate those spurious detections towards the edges of the image. In practice, for the prior Gaussian model, the mean is set at the exact center of the image and the standard deviation is set as ⅛ of the image dimensions. Then, the system goes through the entire image, pixel-by-pixel, and computes the class-conditional probabilities of both classes, using both the EM/GMM model estimate and the prior Gaussian weighting kernel. Finally, using this information, the system automatically chooses which of the two classes is the lesion class by selecting that class which has the darker/lower mean value from the GMM estimate.

The system automatically selects a threshold on the final probabilities by constructing a histogram of the probabilities from the lesion class, accumulating a Cumulative Distribution Function (CDF), and then cutting off the threshold at 85% of the energy of the CDF. In the end, using the final probability values from the lesion class along with this automatically determined cutoff, the system can threshold the pixels and produce a bounding box or boxes for the ROI estimate to isolate the entire lesion or tissue of interest in the first image.

Applying the ROI Estimate to Segment all Remaining Images

Using the ROI from the first image, the system applies a well-known adaptive gray-thresholding algorithm called Otsu's Method. The ROI is important because the adaptive thresholding will not yield an optimal result if the entire image is considered; however, by just focusing on the lesion and a small region around it, the system is able to extract an optimal gray-level threshold using a histogram of the lesion within the ROI. The threshold then allows the system to assign a value of 255 to all lesion pixels and a value of 0 to all other pixels. The system does this separately at each band image because the gray-level threshold will change from band-to-band. However, the same ROI is used to extract the gray-level threshold from the Otsu algorithm, as this only needs to be a rough estimate around the lesion. The Otsu algorithm assumes that the histogram of pixels is bi-modal (meaning there are only two main classes amongst the pixels, which is true for the lesion/non-lesion assumption), and it calculates the optimal threshold separating these two classes so that their combined spread (intra-class variance) is minimal.

In the end, the system is able to segment all images from the imaging system and assign a binary value to each pixel to isolate the lesion pixels from the non-lesion pixels.

Additionally, the system employs a method to halt the segmentation where the algorithm deems the lesion is no longer visible. Because it is possible that some lesions don't exist deep enough to reach all 10 image depths, it is beneficial to ignore those images where the segmentation has yielded a result that suggests that the lesion is not visible. In this way, the 3D representation of the present invention more accurately represents the full shape of the lesion, without any additional non-lesion information. This is achieved as follows: each segmented image comprises a binary mask yielding which pixels belong to the lesion and which pixels do not belong to the lesion in that image. The system collects the 2D pixel locations (u,v) of all highlighted pixels in a given segmentation mask and computes a Shape feature descriptor using Image Moments. Image Moments are various kinds of weighted averages of an image's pixel intensities, or some function of these averages which is usually chosen to provide some invariance properties. The present system uses the well-known "Hu Invariants" (See http://ieeexplore.ieee.org/xpl/login.jsp?tp=&arnumber=1057692&url=http%3A%2F%2Fieeexplore.ieee.org%2Fxpls%2Fabs_all.jsp%3Farnumber%3D1057692). These yield a 7-element "descriptor", meaning a vector with 7 numbers, each of which uniquely describe the shape of the lesion on this particular segmentation mask. Beginning with the first image (image "0"), the system computes the Hu Moment as $H_0$. Then, the system computes every subsequent Hu Moment at the next image down in the depth dimension, according to the bandwidths, and calculates the Euclidean distance of each next Hu Moment to the previous Hu Moment. In this way, $H_0$ from image 0 is compared with $H_1$ from image 1, and a "shape distance" is computed. The system does this repetitively and pairwise, between $H_1$ and $H_2$, $H_2$ and $H_3$, and so on, for all ten images (i.e., between $H_8$ and $H_9$). If the Euclidean distance for any pairwise check is too large, defined by a Euclidean distance threshold that is empirically determined (e.g., 0.04), the system immediately stops and labels that image as the last valid image representing the lesion. The intuitive explanation for this is that the shape of the lesion, from image to image, should not change significantly. However, if the segmentation were to fail because the contrast of the lesion is too low, the shape will vary significantly and this will be captured by the Hu Moment shape distance checks of the present system. In this way, any further image is deemed to not show the lesion as visible and therefore is ignored. This allows the system to only consider those pixels which are likely to be a part of the lesion and not process the pixels which don't contain the lesion.

This technique can also optionally be used for the melanoma scoring system, as disclosed in U.S. Pat. No. 6,208,749) to improve the scoring accuracy. In that system, a single segmentation mask was used to score all pixels from all images within that mask. However, if the lesion doesn't penetrate deep enough to be contained within all 10 images, then inevitably some pixels will be included in the score which have nothing to do with the lesion, and those pixels will only serve as "noise" in the final score. With the approach of the present system, those pixels which are unlikely to be from the lesion can be ignored, thus reducing the noise in the computation to retrieve a more accurate melanoma score.

Reconstructing the Lesion into a Three Dimensional Image

After checking image quality and completing segmentation, the on board computer contains three sets of images of the skin lesion, which may be displayed as a three dimensional image to the user. Using the segmented lesion pixels, the system is able to construct a point cloud as follows: at every pixel which survives the segmentation algorithm, the system assigns an (x, y, z) point location in units of millimeters (mm). The imaging system is known to have a pixel size of, for example, 20×20 microns, and so the (x,y) location of any pixel (u,v) in any image is transformed to a metric location as follows:

x=u*0.02; // u is the horizontal pixel location, and x is in mm;

y=v*0.02; // v is the vertical pixel location, and y is in mm;

where 0.02 represents 20 microns in mm to transform any pixel to a mm unit. Finally, the z-component comes from the known depths that each bandwidth penetrates the tissue, as a planar representation. In the end, only the segmented lesion pixels are transformed to 3D using this transformation from pixels to mm.

The system defines "texture" or melatonin in images by convolving each gray-scale image with a pre-defined kernel that highlights spatial gradients in the image. A "convolution" is a mathematical operation on two functions (in the present case, the image is one function and the pre-defined kernel is the other function), producing a third function (in the present case, this would be the texture image). In image processing, convolving images with kernels typically highlights different characteristics of the image. In this case, the objective is to highlight where local spatial gradients are high, i.e., where nearby pixels in small square neighborhoods have very different values (referred to as high texture), conversely marking those areas with very similar values in small neighborhoods within the image having low texture. A convolution allows the system to estimate this with a single operation. The kernel, k, that the system uses to compute the texture image via convolution is a 3×3 matrix defined as follows:

k=[−2.0 1.0 −2.0;
  1.0 8.0 1.0;
  −2.0 1.0 −2.0]

To assign a color, the system knows the color from the original (u, v) used to create (x_k, y_k, z_k), so this can be looked up directly in the image. So, for example, referring to the original gray-scale image at level k as I_k, and the associated "texture" image as T_k, the system can assign a gray-scale color to (x_k, y_k, z_k) by taking the pixel value at I_k(v, u), and similarly, the system can retrieve the RGB color associated with the texture image T_k as T_k(v, u). Then, when the 3D point is rendered, the system can assign the appropriate color straight from the image.

It is further possible to "fill in" the 3D image of the present invention by interpolating data in planes between each of the 10 images measured at each different wavelength. Weighted averages of the data from adjacent measured images can be calculated to create an interpolated "image." The present invention achieves this via bilinear interpolation, where the key idea is to perform linear interpolation first in one direction and then again in the other direction. By interpolating a pixel from two different images at that same pixel location, bilinear interpolation allows the system to take a contribution from both images to produce the "interpolated" value. Linear interpolation, on the other hand, would be to use some weighted version of that pixel from only one image. The present system could use linear interpolation (as well as any other known method of interpolation), but bilinear interpolation produces more accurate results. For example, static depths can be assigned to each image according to the bandwidth (band 0=0.4 mm, band 1=0.7 mm, band 2=0.8 mm, band 3=0.9 mm, band 4=1.3 mm, band 5=1.7 mm, band 6=1.9 mm, band 7=2.0 mm, band 8=2.2 mm, and band 9=2.5 mm). Therefore, using bilinear interpolation, the system can interpolate any image at any depth using the two closest images from this original set of 10 images, according to their depths. Suppose the system wanted to interpolate an image at 0.5 mm. First, it would go through the list of 10 images listed above and find the two consecutive images with the closest depths, one above and one below the desired depth. This would yield the images at 0.4 mm (band 0) and 0.7 mm (band 1). The appropriate weights are then assigned to linearly interpolate first forward from 0.4 mm and then backwards from 0.7 mm, and this is done simultaneously. More specifically, given a desired depth, the depths of the two closest consecutive images, $I_0$ and $I_1$, are found from the original set of 10, as d0 and d1. The system then computes weights on these images as:

$$w0=1.0-((desiredDepth-d0)/(d1-d0))$$

$$w1=1.0-((d1-desiredDepth)/(d1-d0))$$

These weights then determine how to weight the pixel values from each pixel in $I_0$ and $I_1$ in the interpolated image, referred to as $I_{int}$. For example, considering any given pixel (u, v), the system computes:

$$I_{int}(u,v)=w0*I_0(u,v)+w1*I_1(u,v)$$

Examples of the 3D images thereby produced are illustrated in the Images in the Appendix, starting with Image 3. The 3D images, once created, can be rotated in space in the Lesion Renderer embodiment of the present invention. Rotation and other image manipulation is enabled by using programming techniques well known in the art for manipulating computer-rendered 3D images. The 3D images can also be "sliced" to show interior portions from left to right, from right to left, and from top to bottom, using programming techniques known in the art. In the Lesion Renderer used with this embodiment of the present invention, this "slicing" is accomplished by sliding the bars on the left hand side of the Renderer, as shown in Image 3.

Image 3 shows a multispectral gray-scale image of a lesion created by the present inventive system. The 3D image was created by using 2D images taken at successive layers, up to 2.5 mm deep into the skin below the lesion, as described above. The gray-scale tone of each pixel corresponds to a "texture" or other parameter calculated for each pixel, which may be calculated according to the method described in U.S. Pat. Nos. 6,081,612 and 6,208,749 or as described elsewhere herein. As the pixels get darker, the imaged tissue is more disorganized. A 3D gray-scale image with the right side of the lesion removed to show the interior of the lesion, as is possible using the system of the present invention, is shown in Image 4. A zoomed-in 3D gray-scale image is shown in Image 5. A 3D gray-scale image with the top of the lesion removed is shown in Image 6.

It is also possible to render images of the lesion using pseudo-colored representations of features. Image 7 shows a 3D image of a lesion colorized according to "texture." Image 8 shows the same lesion with the top "sliced" off to show the interior. For areas of homogeneity, the algorithm colors the location with cool colors. For areas of high disorganization, the algorithm colors them with warm colors.

The images may be rendered in gray-scale or false color to reflect any of the parameters described in U.S. Pat. Nos. 6,081,612 and 6,208,749, and as set forth herein. For example, the images could be rendered in grayscale or color according to the amount of asymmetry of the lesion. This asymmetry calculation works by first finding the major axis of the lesion. The algorithm then folds the lesion in half along that imaginary line and measures and displays a difference of the two halves. In areas where there is significant asymmetry, it colors the area with warm colors like reds, oranges, and yellows. For areas showing little to no asymmetry, the feature colors the location with cool colors like blues, greens, or black.

Likewise, the grayscale or false color may be applied using parameters determined by direct comparison with lesions previously labeled by experienced medical professionals. By cycling through every possible texture value, texture values can be correlated with clinical observations regarding the depth of cell disorganization, and optimal threshold levels for rendering texture can be determined.

Image 9 shows a 3D image of a lesion where the threshold for showing "texture" has been adjusted. An RGB color is assigned to each 3D point according to the value of the real-valued texture at that 3D point, which is retrieved from the appropriate image. Blue signifies a very high texture, and red signifies a very low texture. All other points are scaled evenly in between blue and red towards green. The slider bar, as shown in Image 9, adjusts a threshold that is used to "hide" or "show" points based on the value of their texture. In other words, each position of the slider bar specifies some threshold on the texture values. For a given value, all 3D points that are larger than that texture threshold value are hidden, while all 3D points that are smaller or equal to that threshold value are shown. By adjusting the threshold with the slider bar, one can observe how the 3D points are distributed based on their texture values. As shown in Image 9, a very low fixed background level of grey color is applied so that the viewer can see in ghostly form the outlines of the entire lesion, so that the areas of high disorganization are seen "floating" inside the lesion. In this way, those 3D points which do not conform to the given texture threshold value from the slider bar are drawn with a lower alpha value, and are much more transparent. This is done so one can observe where the highlighted 3D points are located relative to the rest of the lesion, using different levels of transparency.

The 3D lesion imaging system of the present invention can also be used to image tissue that has been removed from a patient. The removed tissue may be fixed in some material like paraffin, for example, before it is imaged. Similarly, a viewer may also prepare a 3D image of a lesion using the imager of the present invention and then use the 3D image while directly examining the lesion. By viewing the tissue directly under a microscope, while also referring to a previously prepared 3D image of the lesion, it is possible to improve analysis and diagnosis of lesions.

Image 10 shows the operation of the measuring mode in the Lesion Renderer embodiment of the present invention. The distance between the two red dots shown on the lesion is 1.19651 mm, as displayed in the upper left hand of the Lesion Renderer image. Alternatively, the measuring mode can switch to a 2D point cloud to ensure consistent dimensionality for depth measurement.

OpengGL Rendering

Another embodiment of the 3D lesion visualization application is described below in subsections A, B, C and D. For example, the prior art MelaFind system extracts lesion appearance in gray scale images at 10 different depths beneath the skin surface. One can convert this information to other textures for better understanding of shape and intensity variations using RGB coloring. Thus, to display a single layer of lesion with size 1024×1280, one needs total 1310720 vertices, and texture color for each vertex. The memory requirement to store this information would be (1310720×3 (vertex, XYZ)+1310720×3 (texture, RGB)) units.

As opengl doesn't store the state of vertices and texture, the complete information is required to be transferred to an opengl context on every small change in the display angles. This operation with such a high volume of information results in a high turnaround time leading to a considerable lag while moving point cloud. One of the options to reduce the data transfer time could be to store vertices and textures in the GPU buffer (VBOs or VAOs), and get shaders to load this information to the opengl context. This option fails due to the limitation on the graphic card memory for the Surface Pro 3.

As all the pixels in a single layer of lesion image are assumed to be at same depth and at relative position w.r.t the other pixels, depth (z, same for all pixels in an image), X and Y position is known for each pixel. This assumption can be used to reduce the number of vertices to 4, independent of the image size. It also makes feasible to store the texture (color for all the pixels) on the GPU buffer. Once the texture information is transferred to the buffer, opengl could refer this information with faster turnaround time resulting in a smooth movements of point cloud. Following sections explain the step by step procedure to achieve the proposed method.

Preferably, the 3D visualization system for lesion supporting grayscale, RGB and irregular (non rectangular) objects rendering. The proposed method is being adapted to handle all the requirements. Following topics explain procedures with code snippets to achieve every requirement.

A. Transferring Textures to the GPU Buffer:

This is done only once for an image in the opengl context—not every display call. When not required, it is cleared from the memory. At one time one needs to load texture for every layer in a lesion, including the interpolated layers.

Every texture in the opengl context is identified by a unique id (interger). First a request is made to the opengl context to generate the required number of texture ids. A custom integer could also be used, but there are chances of it colliding with a reserved number.

```
GLuint tex; glGenTextures(1, &tex); // for one texture
OR
GLuint *tex; tex = new GLuint[n]; glGenTextures(n, tex);//for n number of texture ids
```

Now for each texture load an image, for this purpose GLEW is used. GLEW is a very light utility around the glut, it is used specifically for loading images to textures. As the MelaFind vision system is using opencv Mat for storing image information, a code snippet is written to transfer Mat information to the GPU buffer (texture mapping). Every line in the code snippet is explained with comments:

Select the texture id

First, select the texture id for which the given image should be transferred to the buffer or binding an image to texture id.

glBindTexture(GL_TEXTURE_2D, textureID);

Since the number of pixels in original image is resolution independent, they won't always match pixels while displaying. This happens when a texture image is stretched beyond its original size (more number of vertices) or when it's sized down. OpenGL offers various methods to decide on the sampled color when this happens.

```
glTexParameteri(GL_TEXTURE_2D, GL_TEXTURE_MIN_FILTER,
GL_LINEAR); //set to linear interpolation
glTexParameteri(GL_TEXTURE_2D, GL_TEXTURE_MAG_FILTER,
GL_LINEAR); //set to linear interpolation
```

When a texture needs to be applied to a surface with more number of vertices than the number of pixels in the original image, interpolation should be avoided. There could be multiple option to handle such case. The options are GL_REPEAT, GL_MIRRORED_REPEAT, GL_CLAMP_TO_EDGE and GL_CLAMP_TO_BORDER. This functionality is not being used in this embodiment of the lesion rendering system, but it could be.

```
glTexParameteri(GL_TEXTURE_2D, GL_TEXTURE_WRAP_S, wrap_Filter);
glTexParameteri(GL_TEXTURE_2D, GL_TEXTURE_WRAP_T, wrap_Filter);
```

Now, calling a glew routine to load the mat information in the referenced texture,

```
glTexImage2D(GL_TEXTURE_2D,  // Type of texture
    0,  // Pyramid level (for mip-mapping) - not useful in the system
    GL_RGBA,  //Internal colour format to convert to
    image_height,  // number of rows in an image
    image_width,  // Image height i.e. 480 for Kinect in standard mode
    0,  // Border width in pixels (can either be 1 or 0)
    input_Colour_Format,  // Input image format (i.e. GRAY, RGB and RGBA .)
    GL_UNSIGNED_BYTE,  // Image data type
    mat.ptr( ));  // The actual image data itself
```

These steps would bind an image with a texture id in the opengl context.

In order to clear the buffers when not required or new set of textures needs to be loaded,

```
GLuint tex; glDeleteTextures(1, &tex); //for one texture
GLuint *tex; tex = new GLuint[n]; glDeleteTextures(n, tex); //for n number of
texture ids
```

Figure 11:
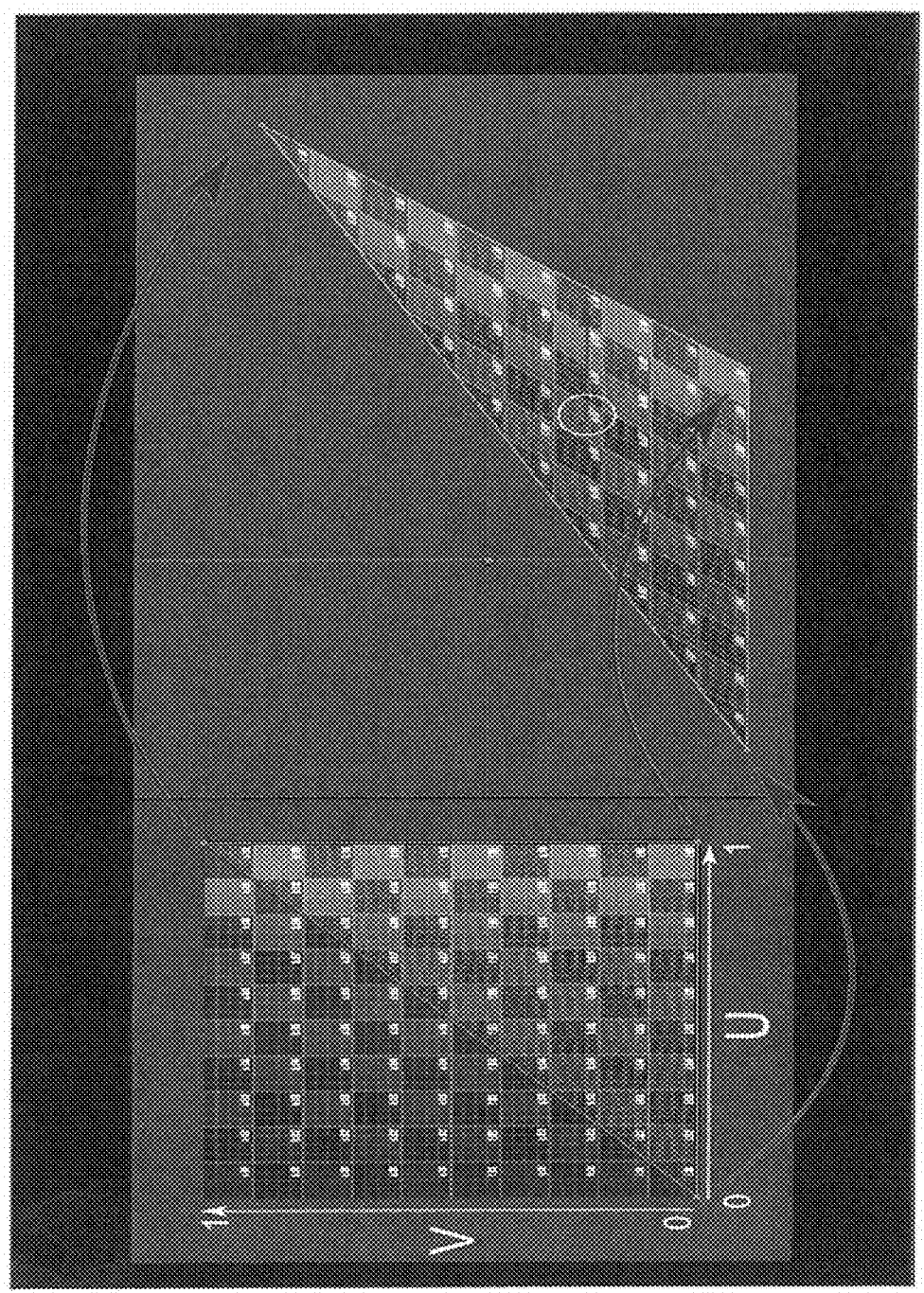
FIG. 11 illustrates texture to plane mapping in the OpenGL embodiment of the present invention.

B. Displaying a Complete Image Using 4 Vertices:

Every 2D texture in the opengl context is mapped in the a unit coordinate system, where 4 corners are mapped to (0,0), (0,1), (1,0) and (1,1). This coordinate system can be used to extract a specific part of a loaded texture, be it a point, line, triangle, square or polygon in general. FIG. 11 visually shows mapping of a triangular texture to a 3D plane.

This could be achieved using a simple code snippet,

```
glEnable(GL_TEXTURE_2D);
    glBindTexture(GL_TEXTURE_2D, texture_id); //the texture want to use, it should
already be loaded
    glBegin(GL_TRIANGLES);
        glTexCoord2f(0.0, 0.0); glVertex3f(0.0, 0.0, 0.0);
        glTexCoord2f(0.0, 1.0); glVertex3f(0.0, 1.0, 0.0);
        glTexCoord2f(1.0, 1.0); glVertex3f(1.0, 1.0, 1.0);
    glEnd( );
glDisable(GL_TEXTURE_2D);
```

As explained earlier, the pixels in an image are at same depth (Z) and having a relative position (X and Y), use of Square (Quad) reduces the number of vertices required to describe image pixels to vertices mapping. We could have a complete texture mapped to a horizontal plane (having fixed width w and height h) placed at a predefined value (depth, z) on the Z axis and around the origin. This can be done using the following code

```
glEnable(GL_TEXTURE_2D);
    glBindTexture(GL_TEXTURE_2D, texture_id);
        glBegin(GL_QUADS);
```

-continued

```
            glTexCoord2f(1.0f, 1.0f); glVertex3f(-w/2, h/2, z);
            glTexCoord2f(0.0f, 1.0f); glVertex3f(w/2, h/2, z);
            glTexCoord2f(0.0f, 0.0); glVertex3f( w/2, h/2, z);
            glTexCoord2f(1.0f, 0.0f); glVertex3f(-w/2, -h/2, z);
    glEnd( );
    glDisable(GL_TEXTURE_2D);
```

Figure 12A:
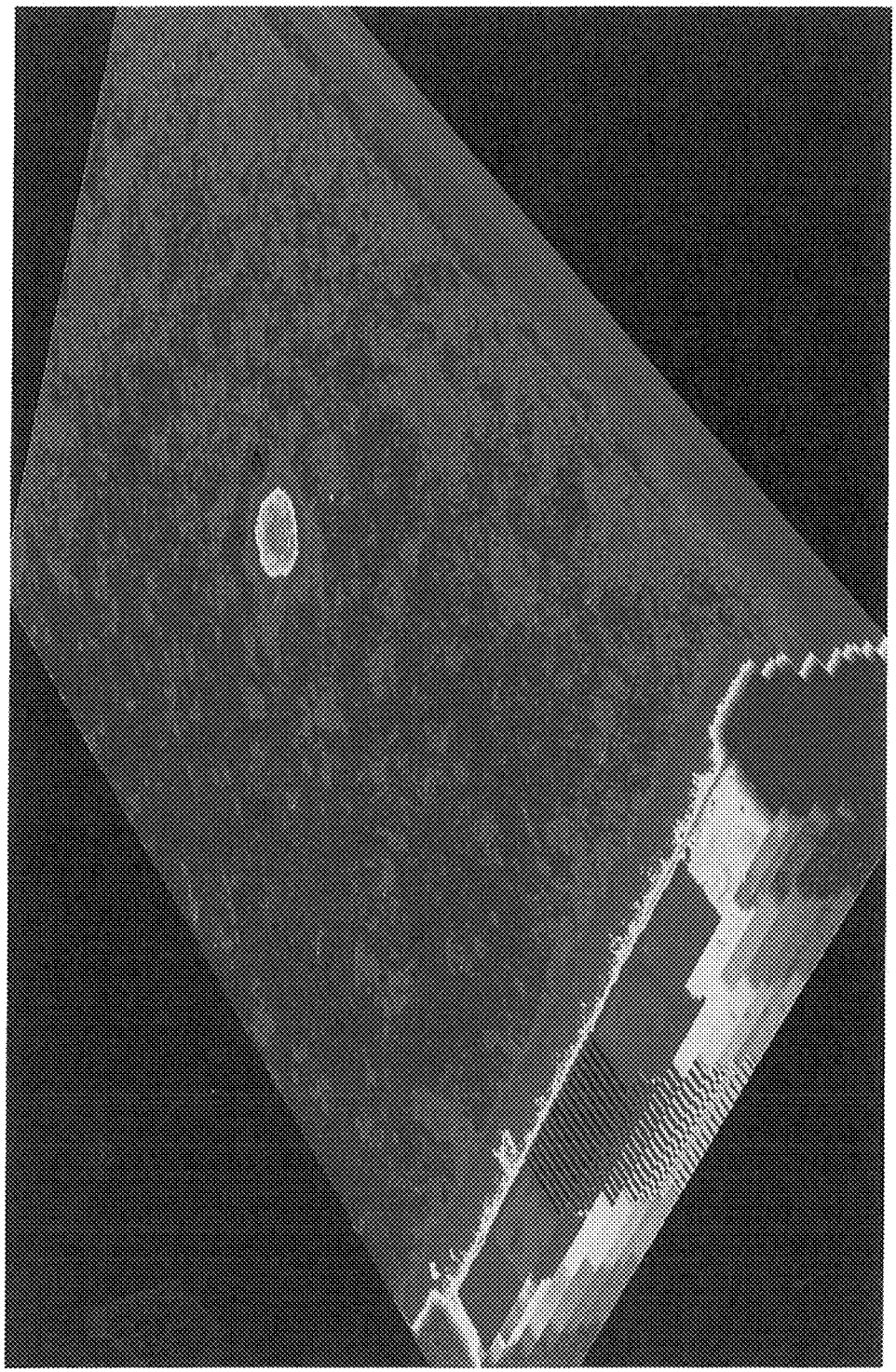
FIGS. 12A and 12B illustrates a complete lesion point cloud in the OpenGL embodiment of the present invention.
Figure 12B:
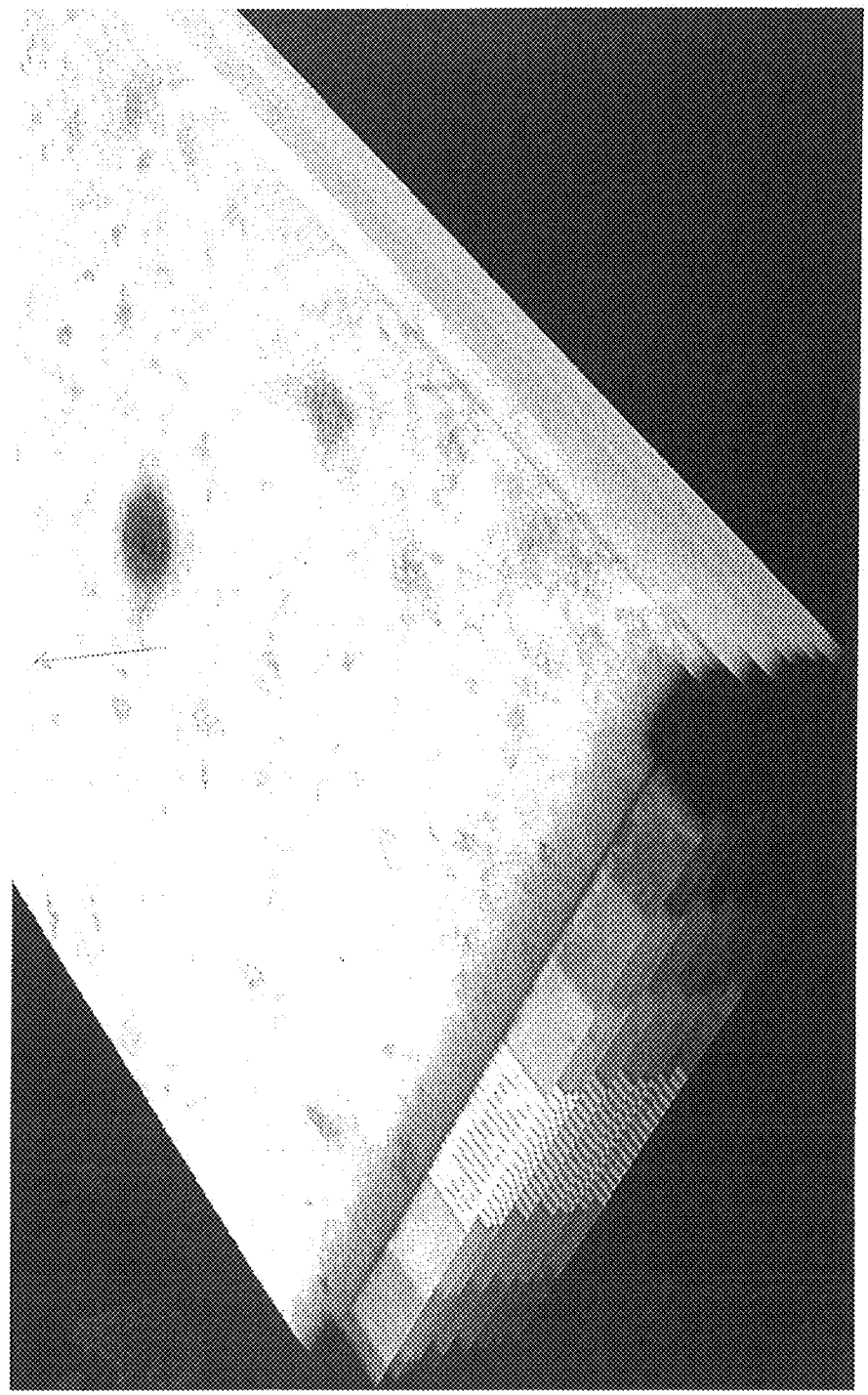

This is done for all the layers in a lesion by changing the texture_id and replacing z with a desired depth to display complete lesion point cloud in 3D as shown in FIGS. 12A and 12B. If the area of plane (in pixels) is bigger than the actual number of pixels in the mapped texture, the defined magnification filter would be applied by opengl before display.

C. Displaying an Image with Cutoff:

In the lesion explorer, one needs a way to observe the variance of an intermediate pixel (at a specific width and height) in a lesion. This is selected by user using the sliders in the User Interface ("UI") as shown in FIGS. 13A (full size lesion rendering) and 13B (partial lesion rendering).

Figure 13A:
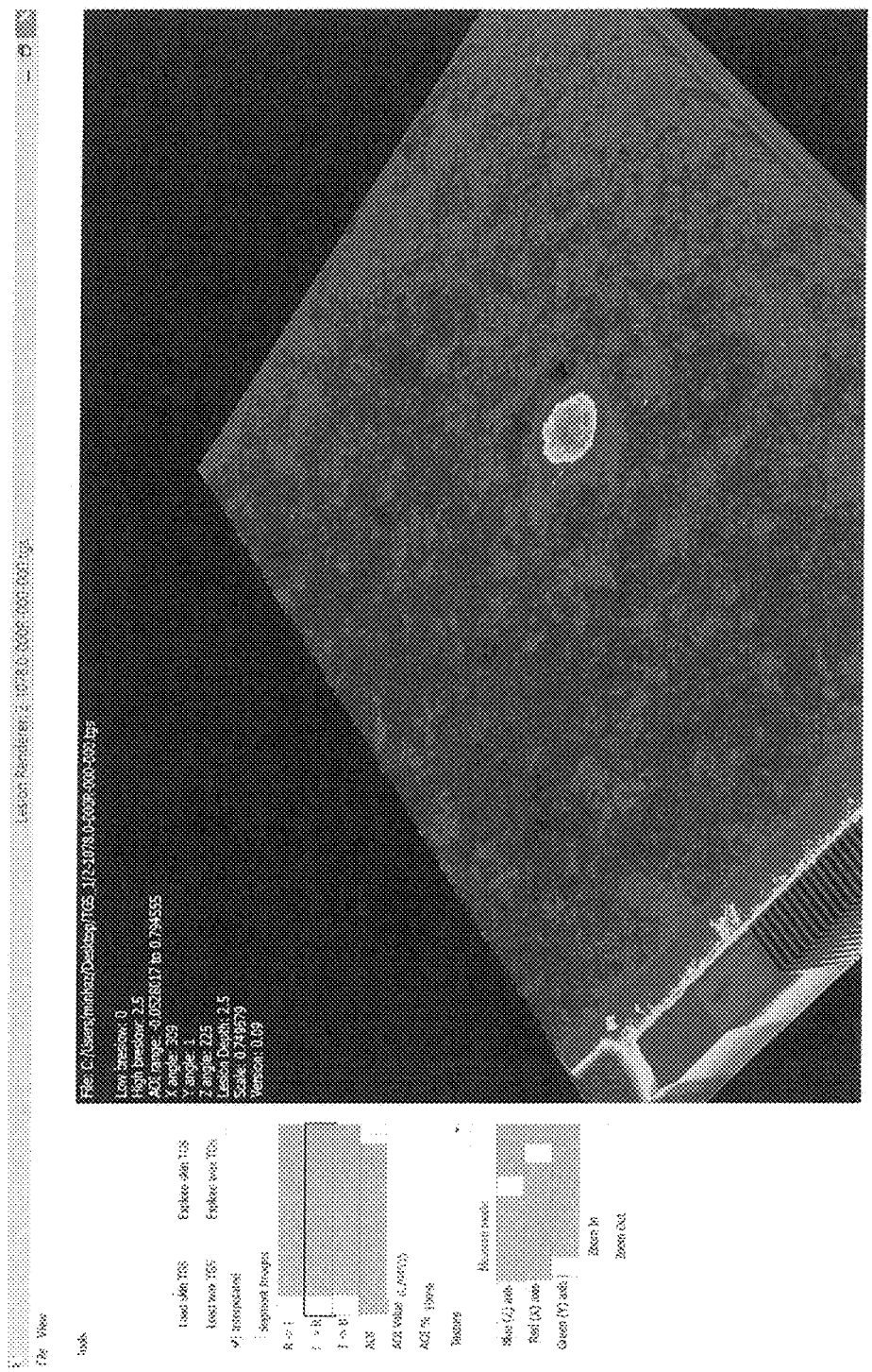
FIGS. 13A and 13B illustrates the variance of an intermediate pixel (at a specific width and height) in a lesion as selected by user in the OpenGL embodiment of the present invention.

Complete image display using method explained till now is not essential for this functionality (as shown in FIG. 13A).

Figure 13B:
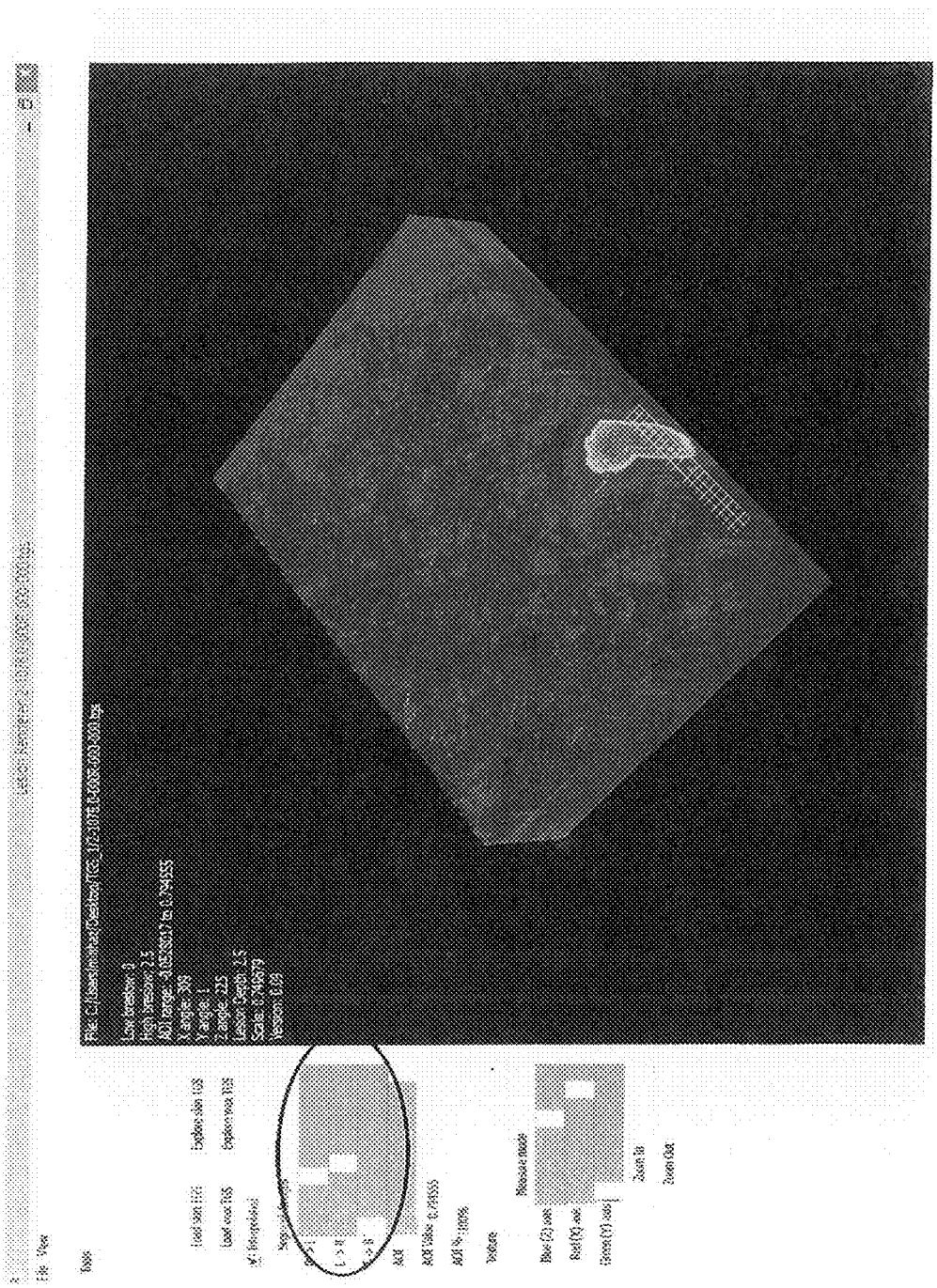

To handle this case partial texture mapping is done based on the user selected cutoffs (as shown in FIG. 13B). The cutoffs are restricted between 0 and 1. Total 3 cutoffs are used for each axis, X, Y and z axes mapped to width, height and depth respectively. The partial texture mapping is done using the following code snippet.

```
if z is within the z_cutoff
    glEnable(GL_TEXTURE_2D);
```

```
    glBindTexture(GL_TEXTURE_2D, texture_id);
        glBegin(GL_QUADS);
        glTexCoord2f(1.0f, 1.0f - y_cutoff); glVertex3f( -w/2, h/2- h * y_cutoff, z);
        glTexCoord2f(0.0f + x_cutoff, 1.0f - y_cutoff); glVertex3f(w/2 - w * x_cutoff,
        h/2 - h * y_cutoff, z);
        glTexCoord2f(0.0f + x_cutoff, 0.0); glVertex3f( w/2 - w * x_cutoff, -h/2, z);
        glTexCoord2f(1.0f, 0.0f);
        glVertex3f(-w/2, -h/2, z);
        glEnd( );
    glDisable(GL_TEXTURE_2D);
```

D. Displaying an Irregular Object:

Approaches explained till now are enough for displaying lesion images in full and partial sizes. However, it can only display multiple rectangular textures with specific height and width placed at specific depths in 3D. Generally lesions are of irregular shape as shown in the images below.

Figure 14:
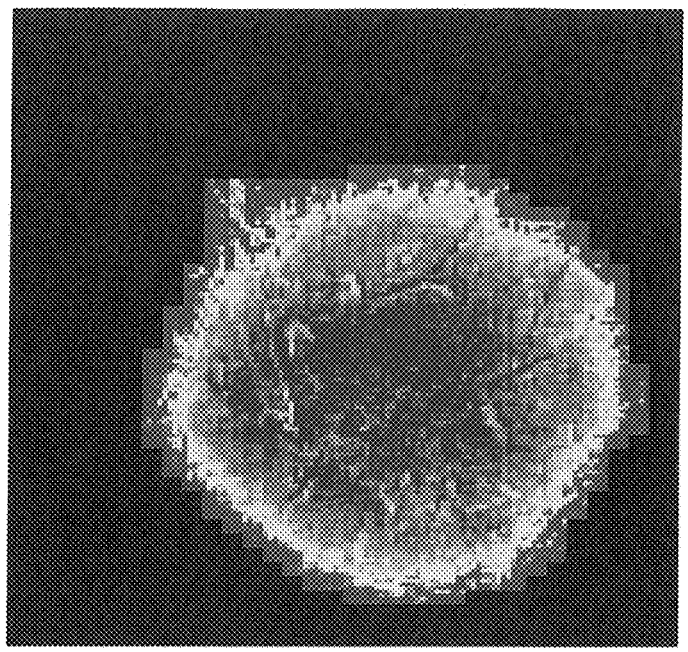
FIG. 14 illustrates a segmented lesion rendered in the OpenGL embodiment of the present invention in which the black region is background.

It is stored in a normal rectangular image holder (Mat in opencv), black are in the FIG. 14 is background. An additional binary image (FIG. 15) is used to define the foreground (lesion) pixels within a segmented lesion image. The size (width and height in pixels) is same of both the images. The pixels with binary value 1 are part of lesion, the pixels with binary value 0 belong to the background.

To display only the lesion pixels, one of the approach could be to look up the binded texture buffer for all pixels one by one.

```
glBegin(GL_POINTS);
    if a point is part of lesion
    glTexCoord3f(R, G, B); glVertex3f( X, Y, Z);
glEnd( );
```

The color (R, G and B) for every pixel could be extracted from a texture buffer by querying at a coordinate. The coordinate for a point is found by normalizing the width and height between 0 and 1, and rounding off the number to the nearest whole number.

The approach has a limitation as lookup is done for every pixel. In this approach it is not useful to load textures in the GPU buffer, as each pixel is read again in the code and sent to the opengl context. The resolution might also be very low. So, one possibility is to do look up from the original image, which may lead to a large turnaround time in displaying a full size point cloud.

Another solution is to do pixel filtration on the fragment shader. The fragment shader could be customized to skip the pixels not part of the foreground. As the opengl supports RGBA rendering, the alpha channel shader is directly used to achieve filtration.

Figure 16:
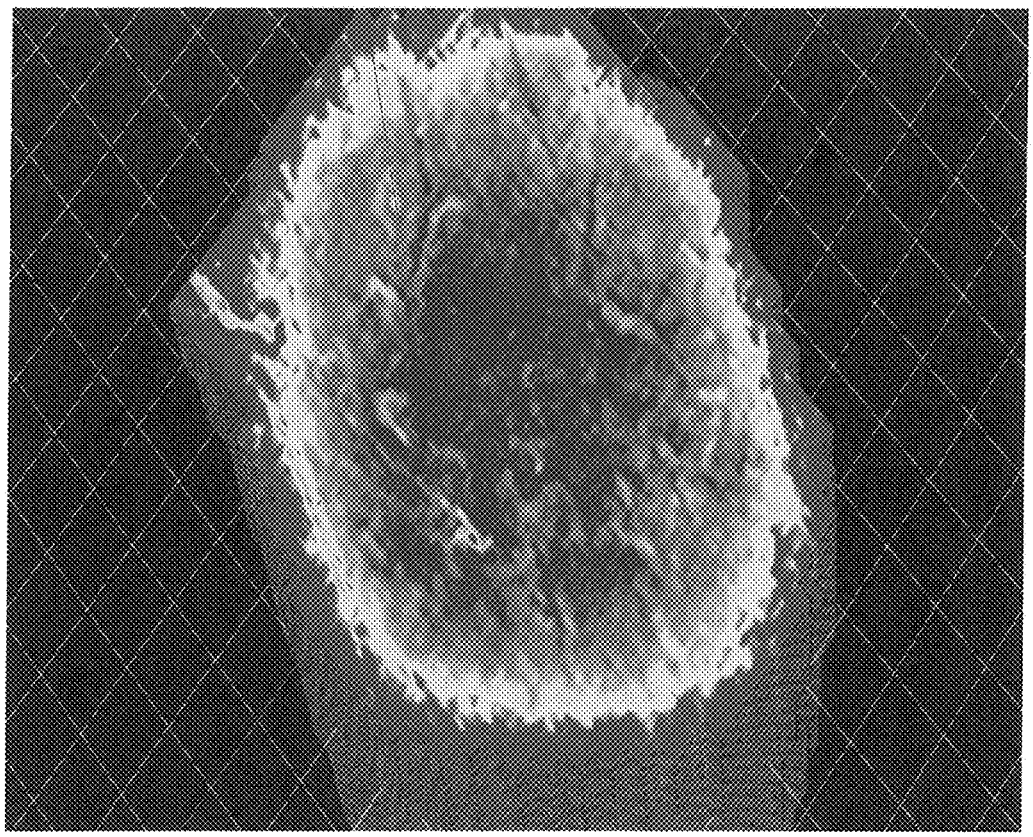
FIG. 16 illustrates a segmented lesion rendered in the OpenGL embodiment of the present invention.
Figure 1:
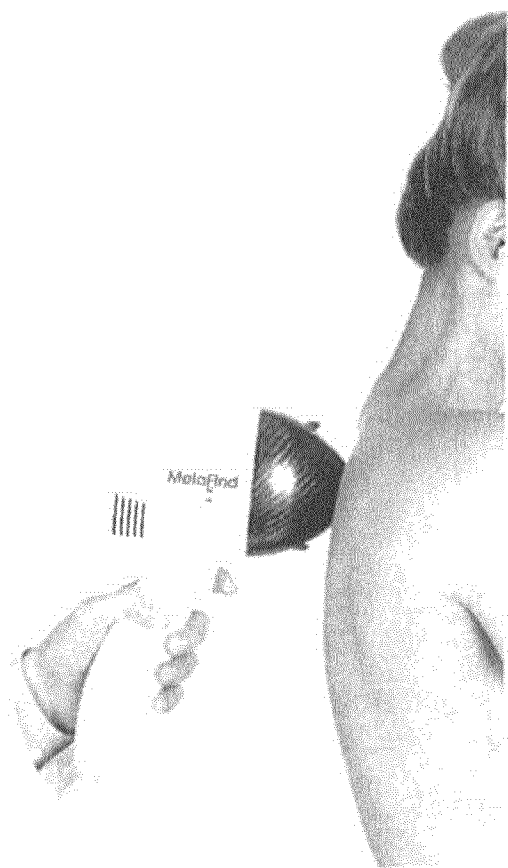
Figure 2:
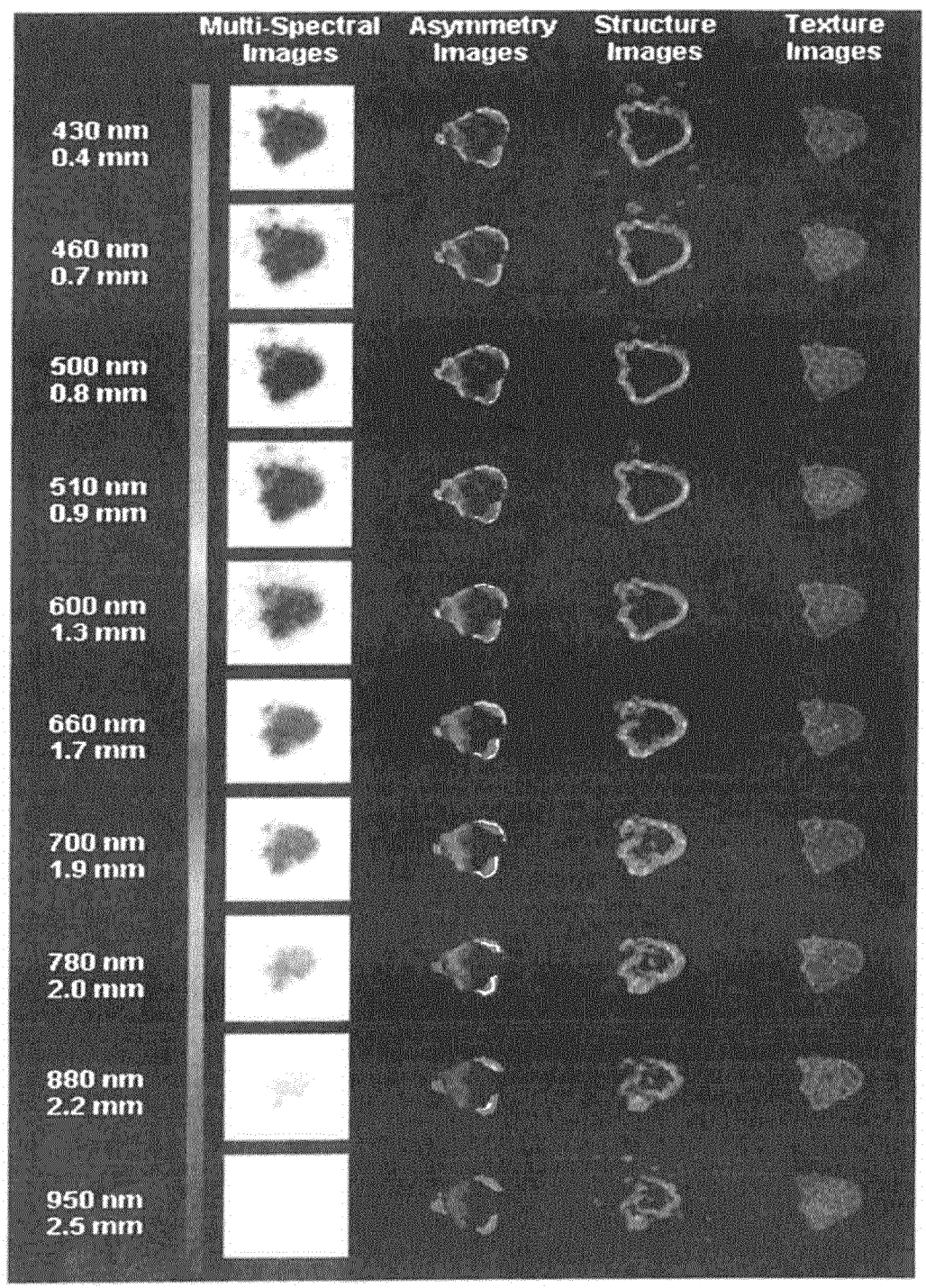
Figure 3:
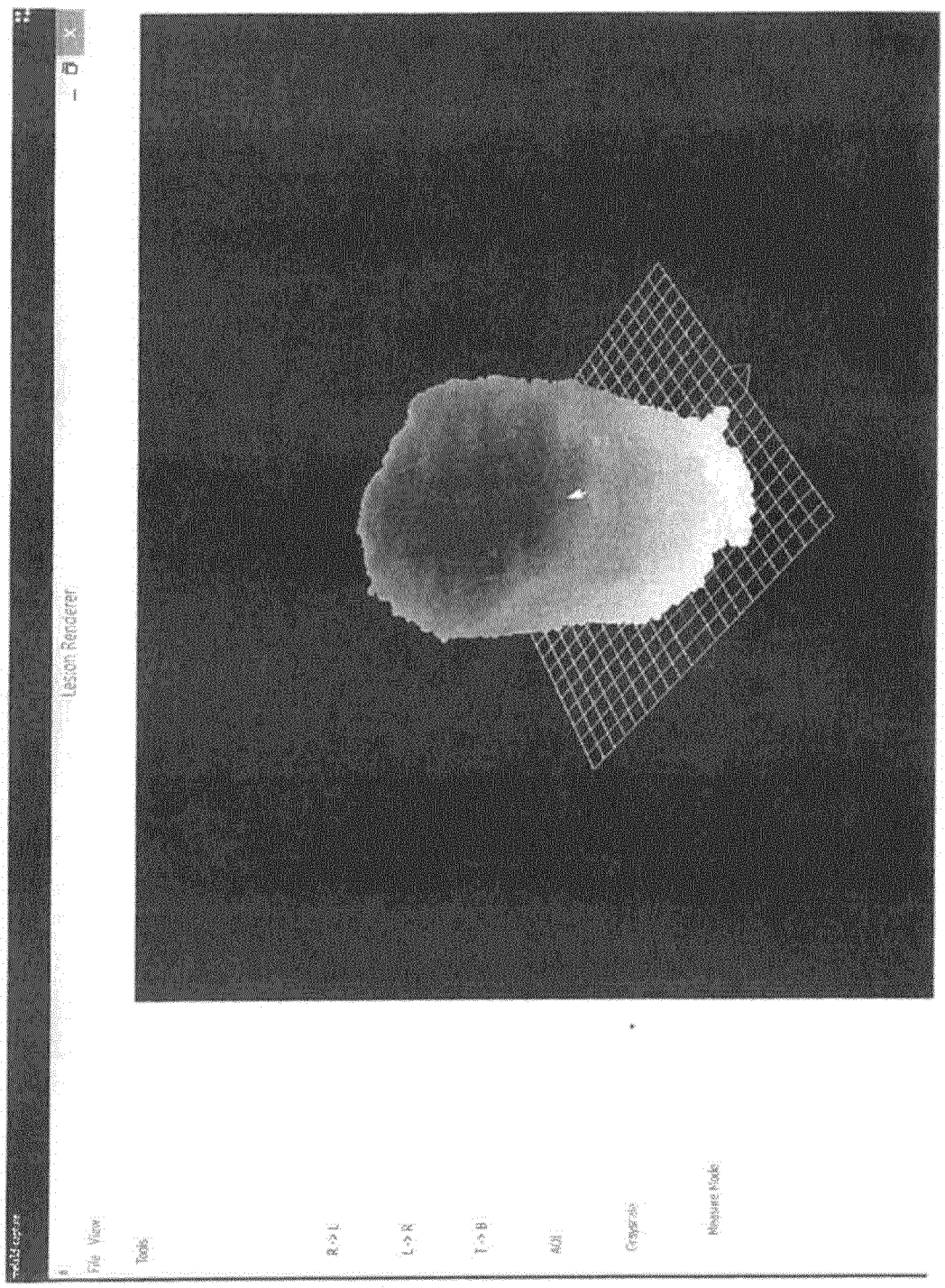
Figure 4:
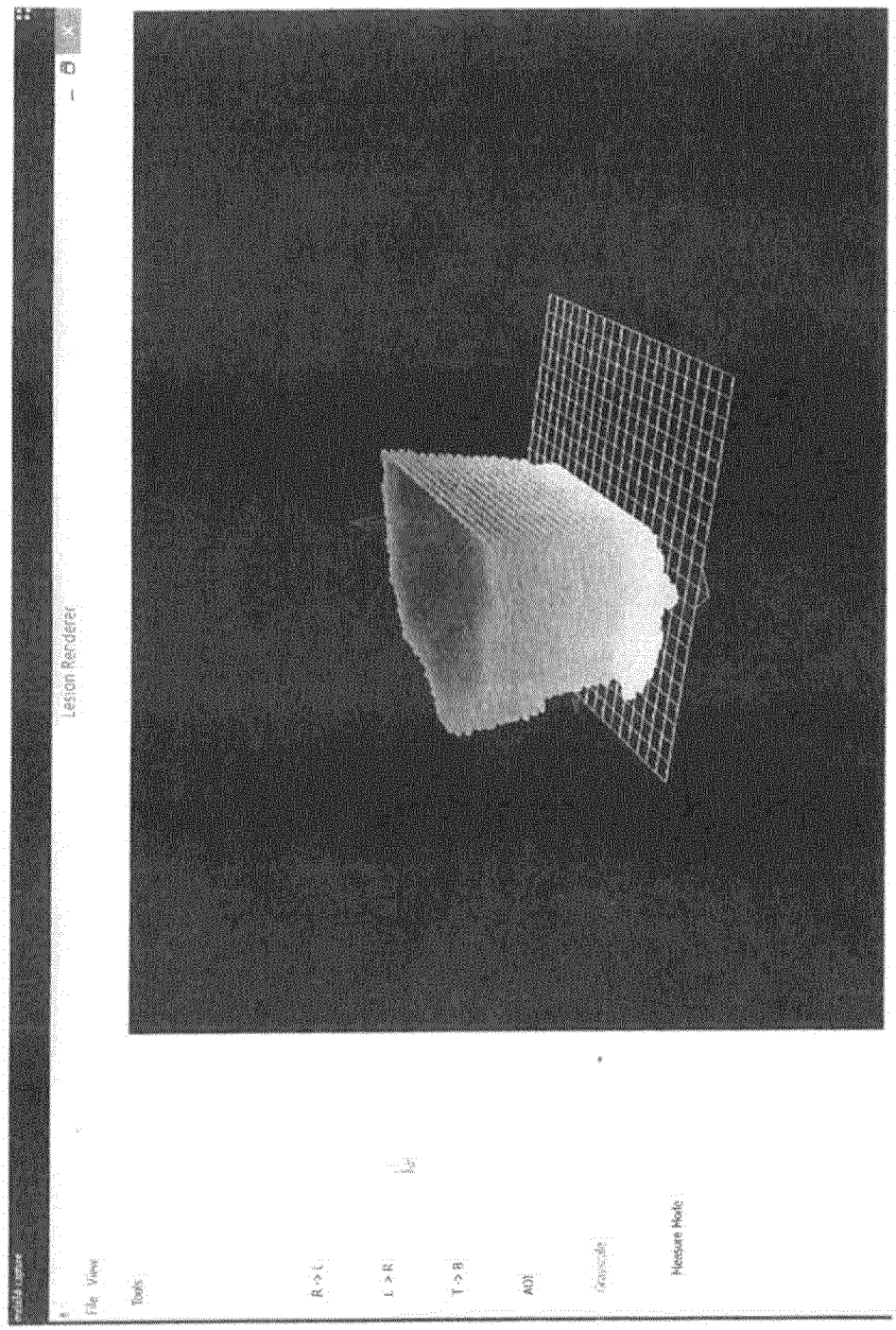
Figure 5:
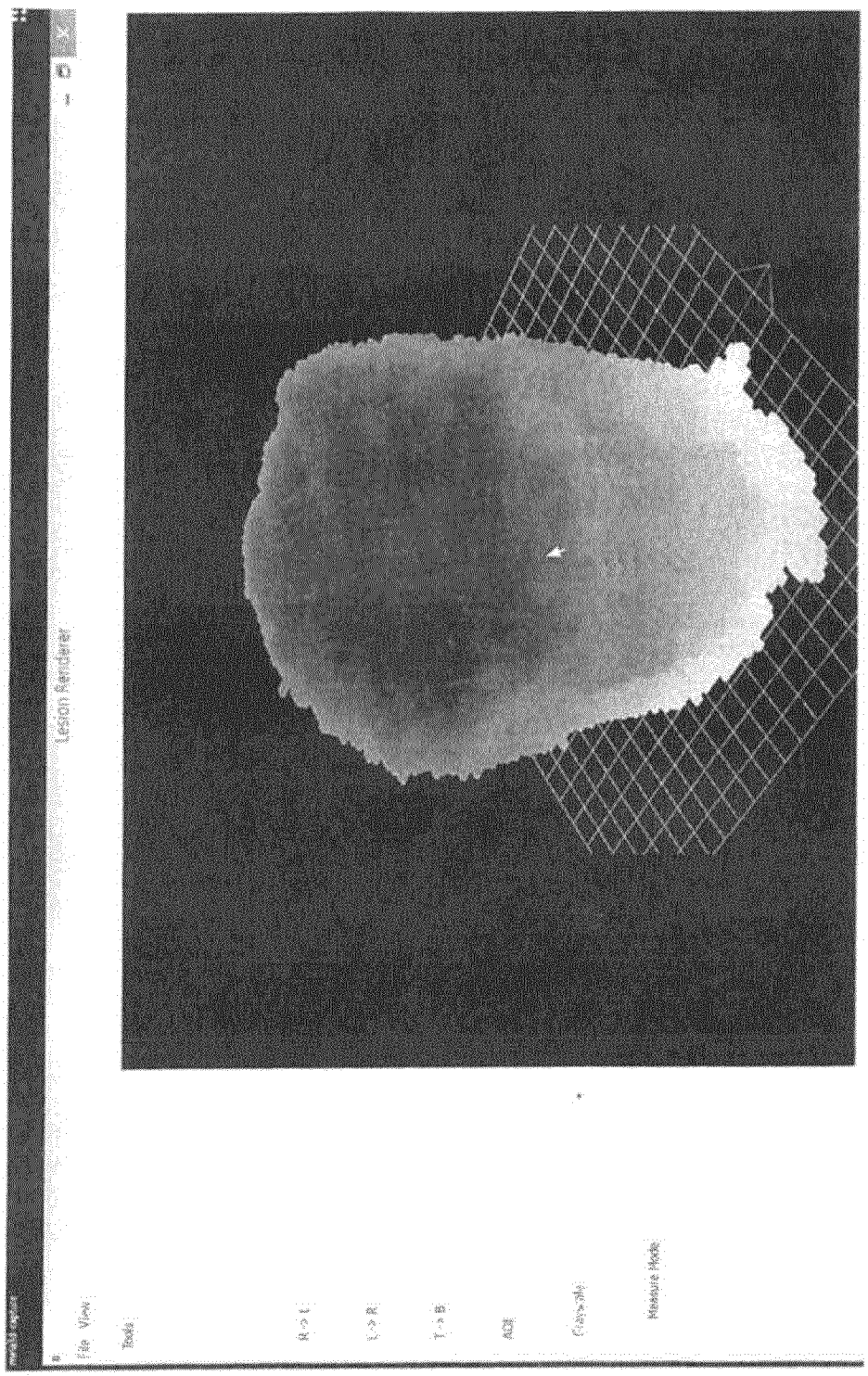
Figure 6:
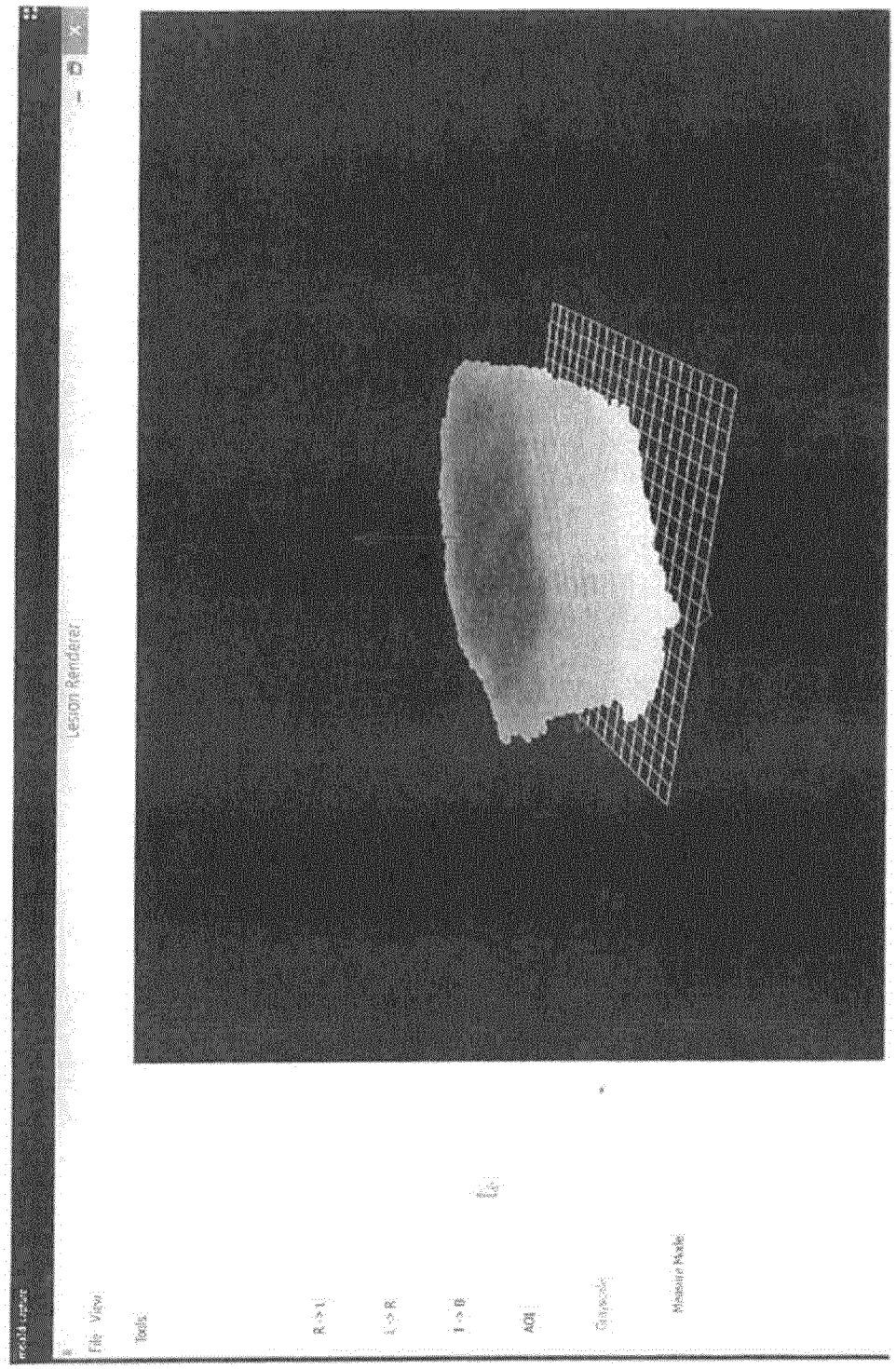
Figure 7:
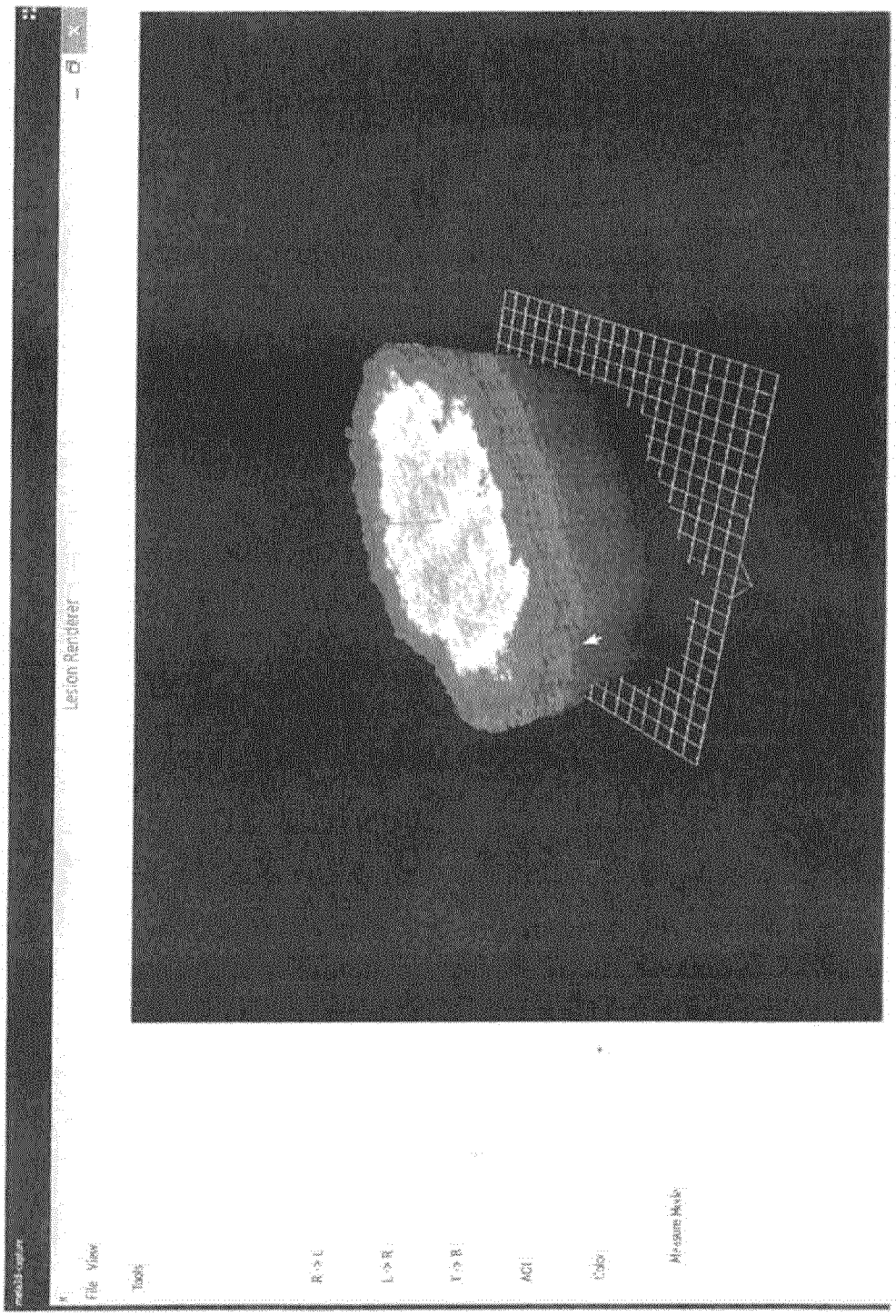
Figure 8:
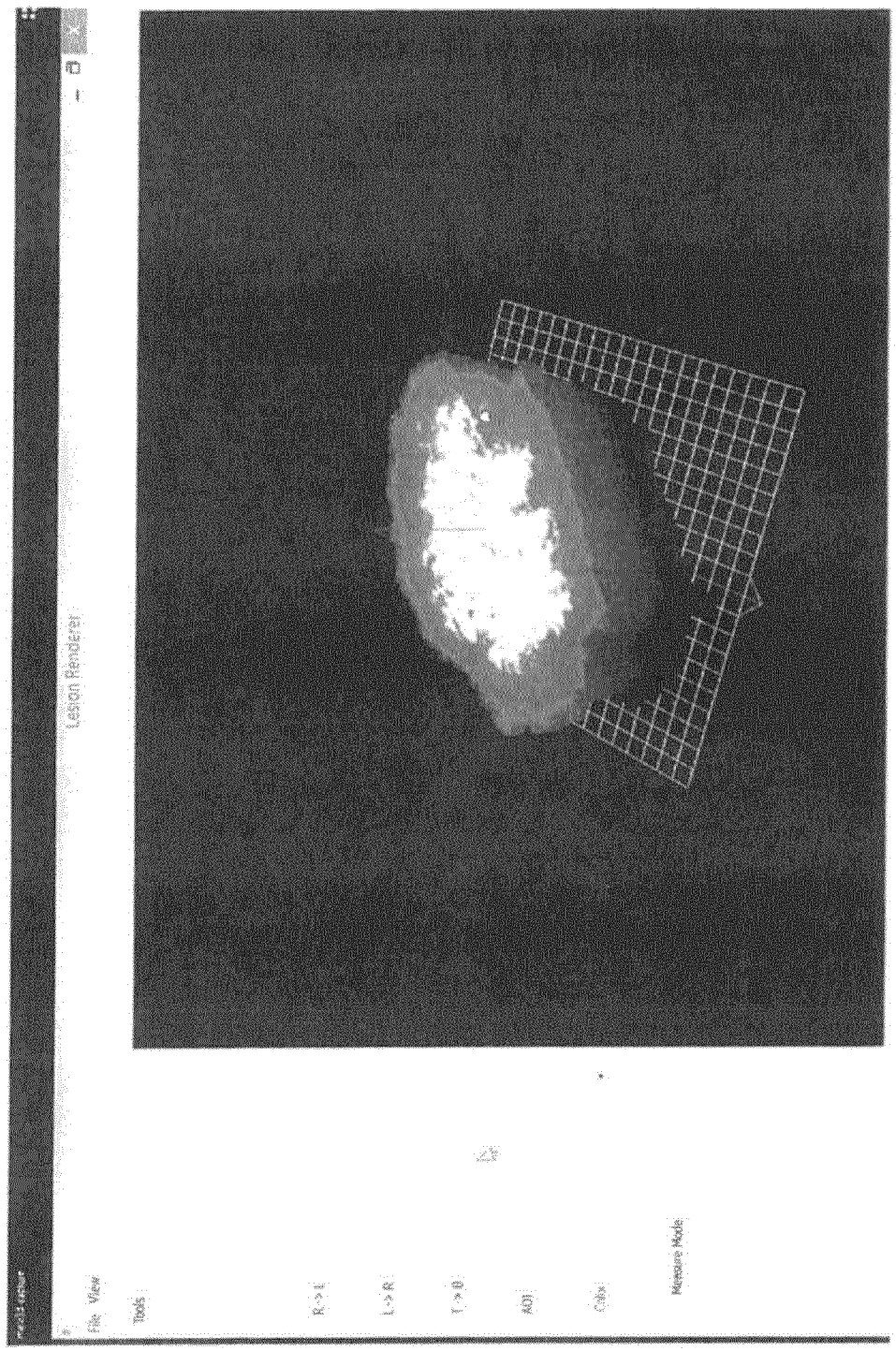
Figure 9:
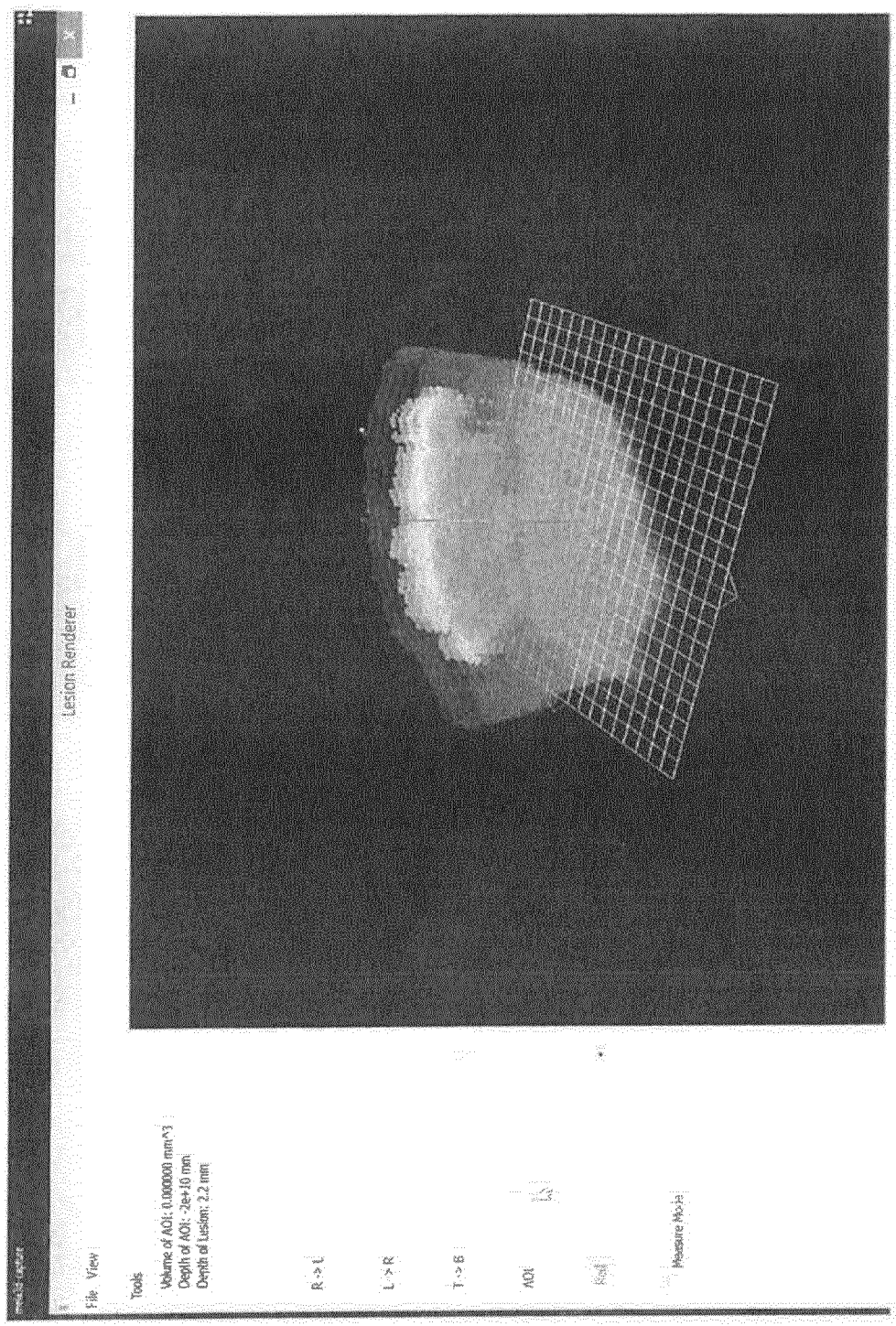
Figure 10:
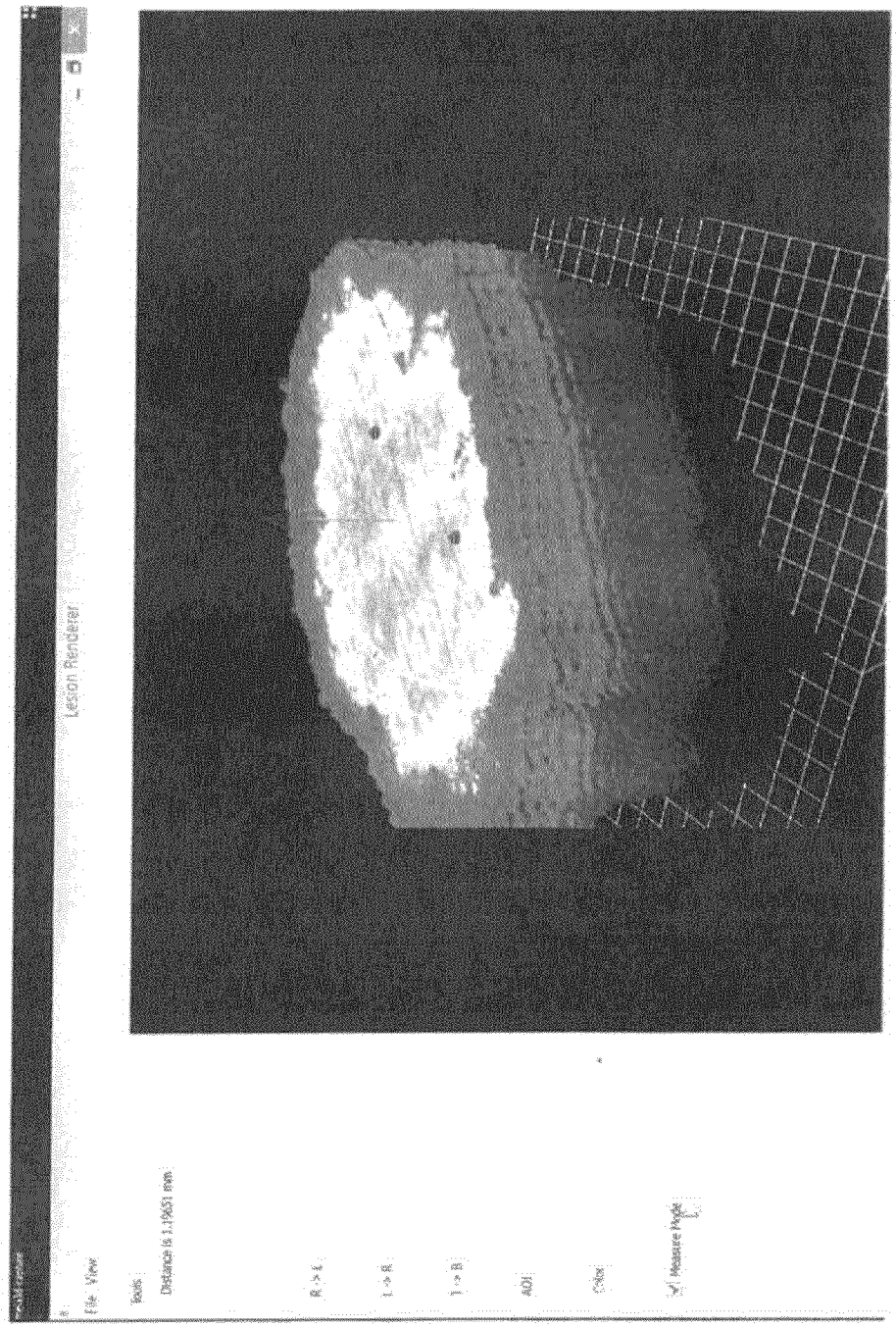
Figure 12A:
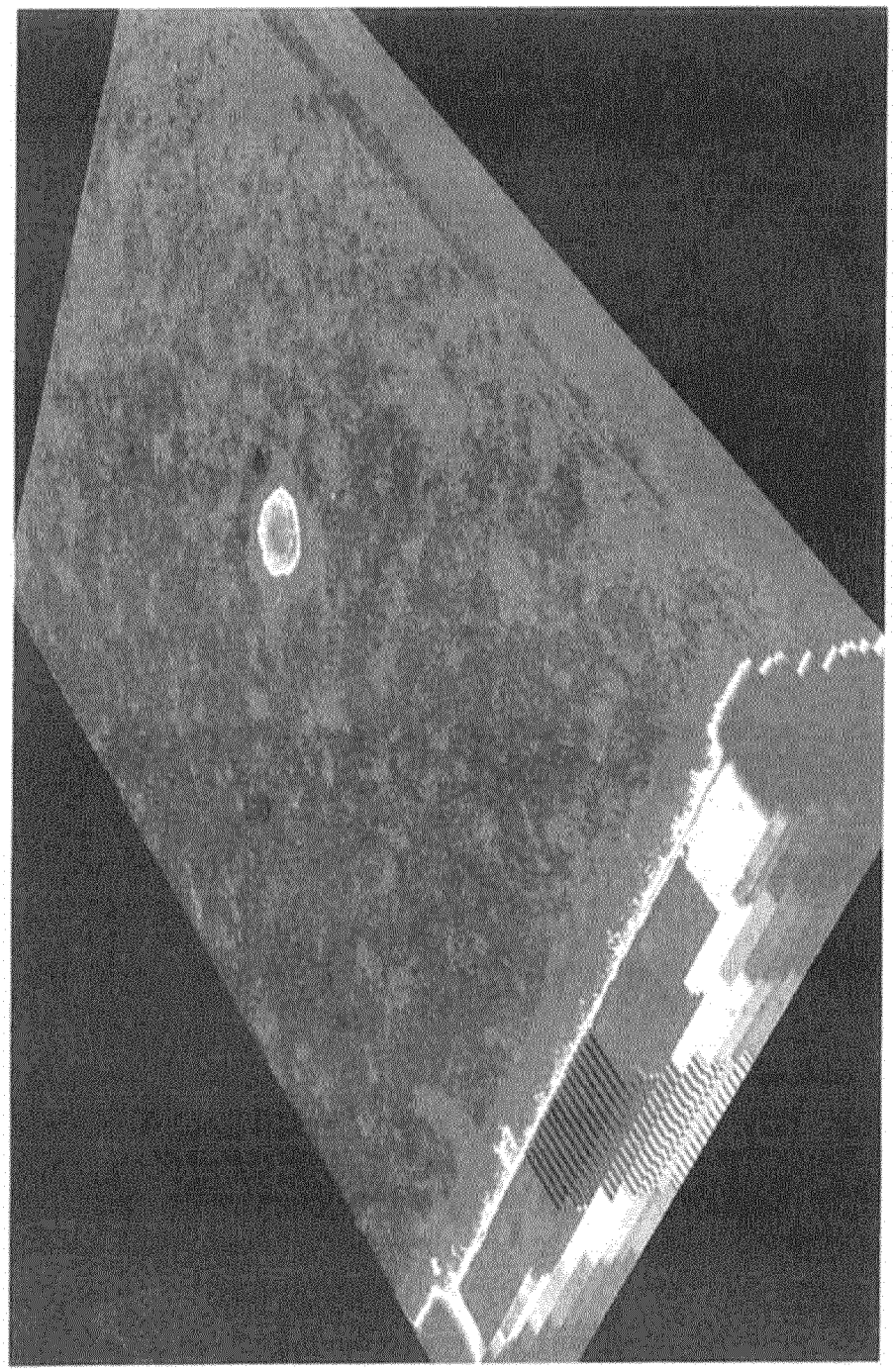
Figure 12B:
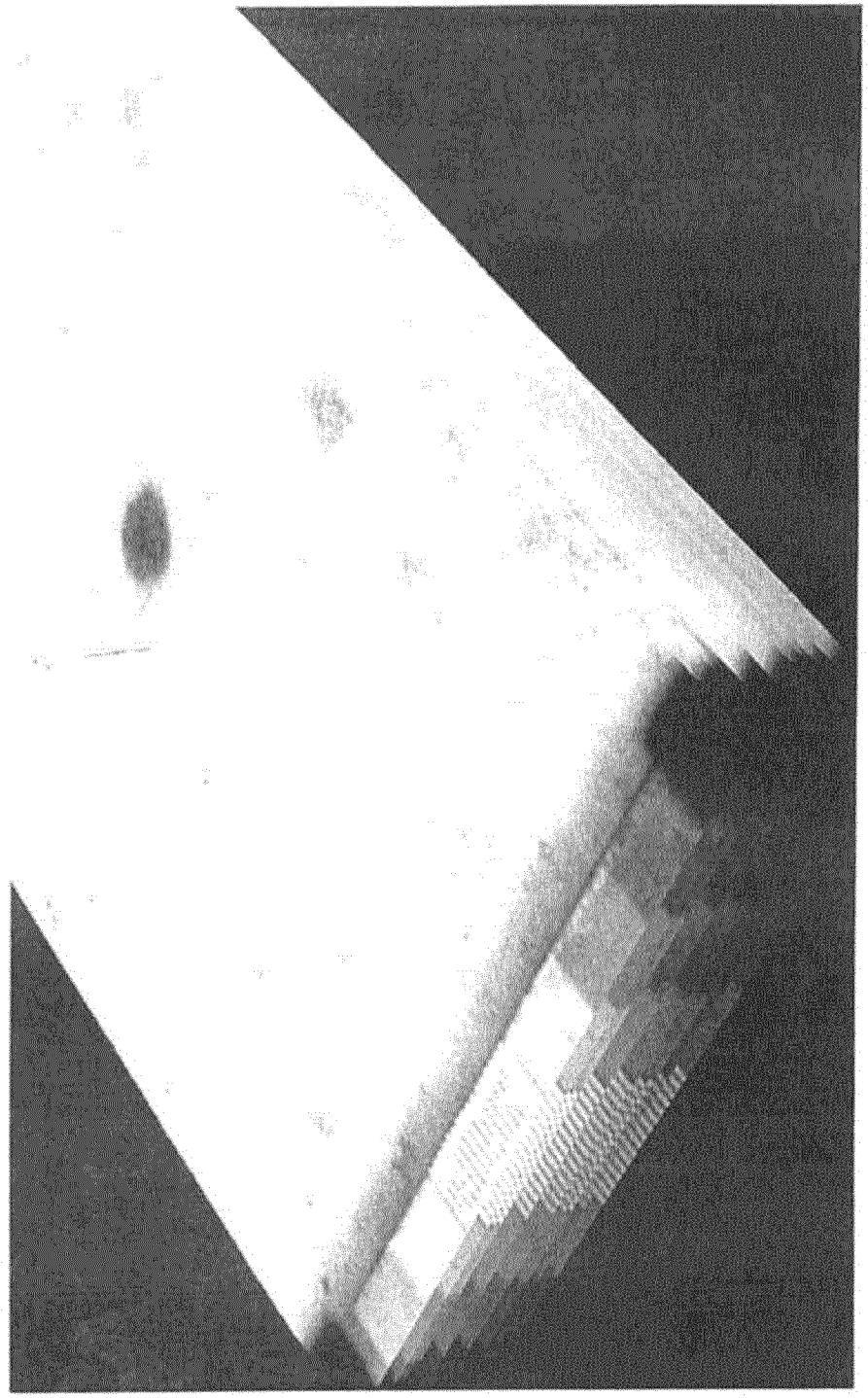
Figure 13A:
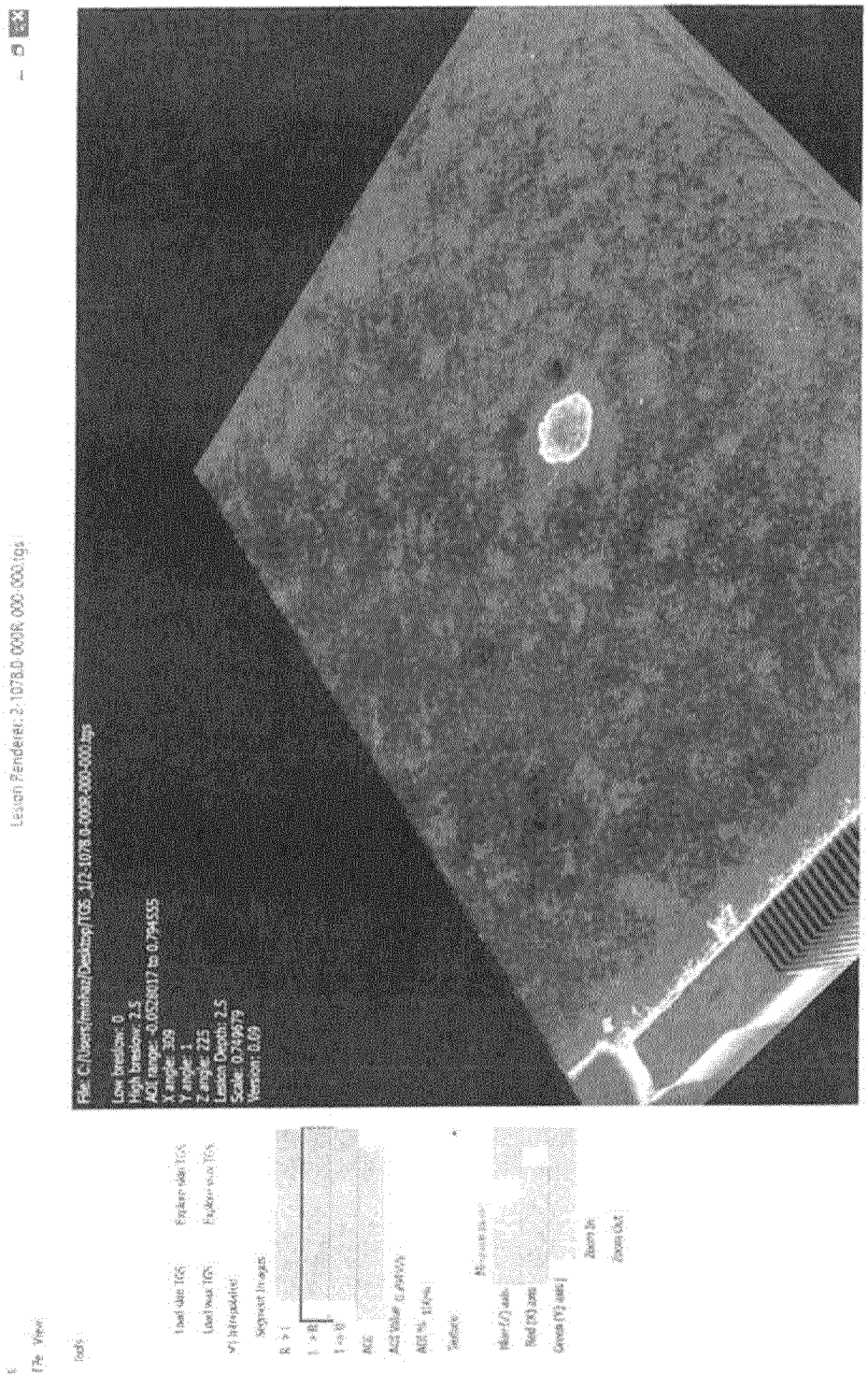
Figure 13B:
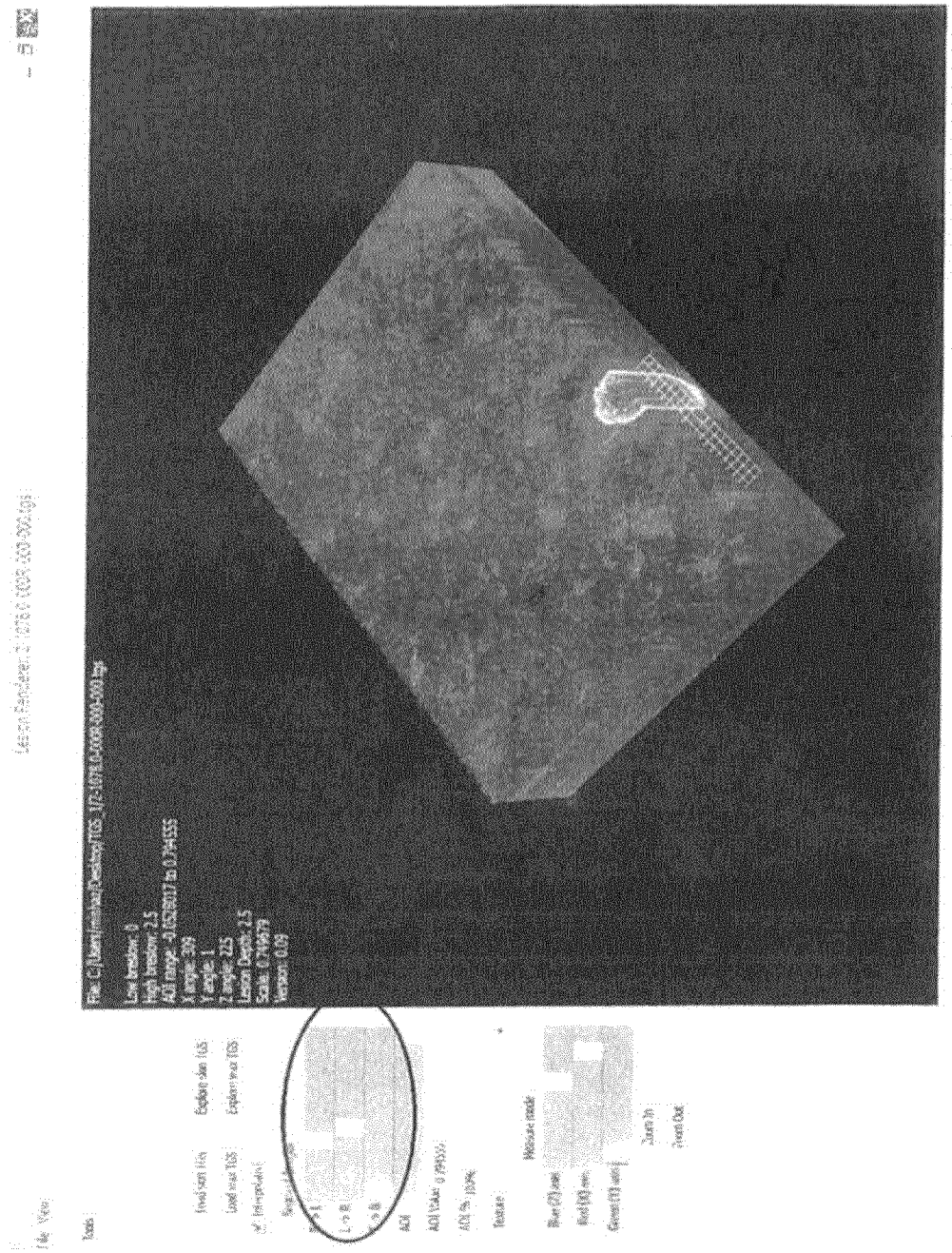
Figure 14:
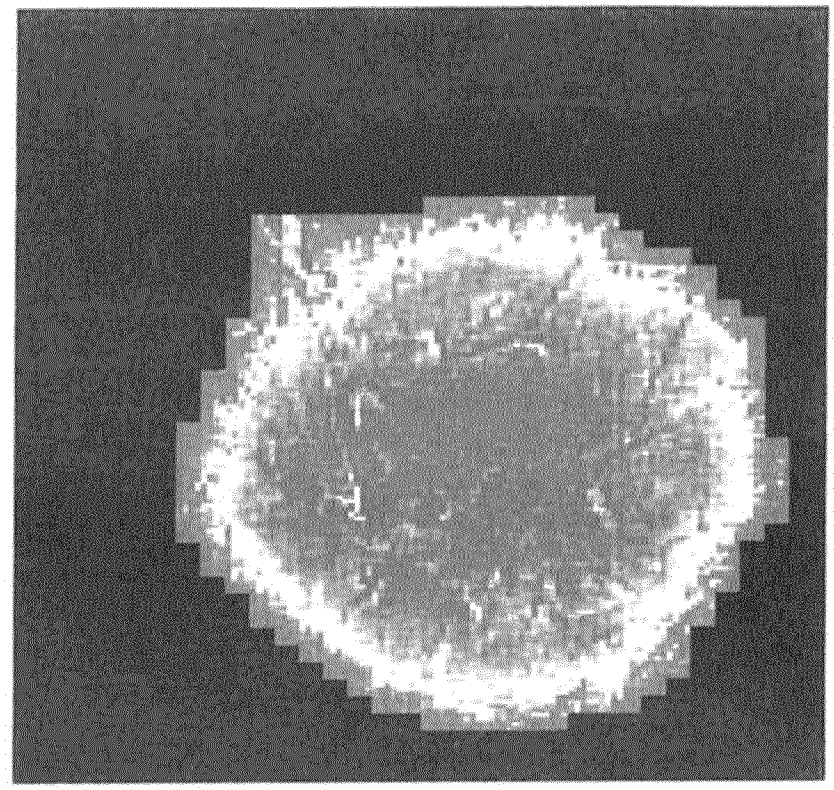
Figure 15:
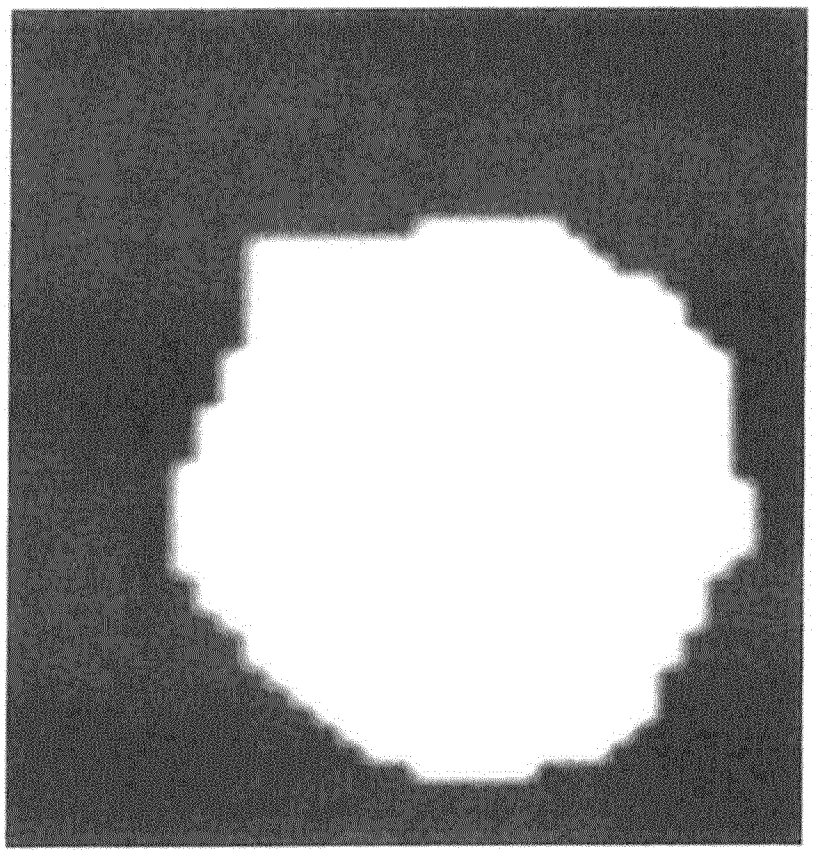
Figure 16:
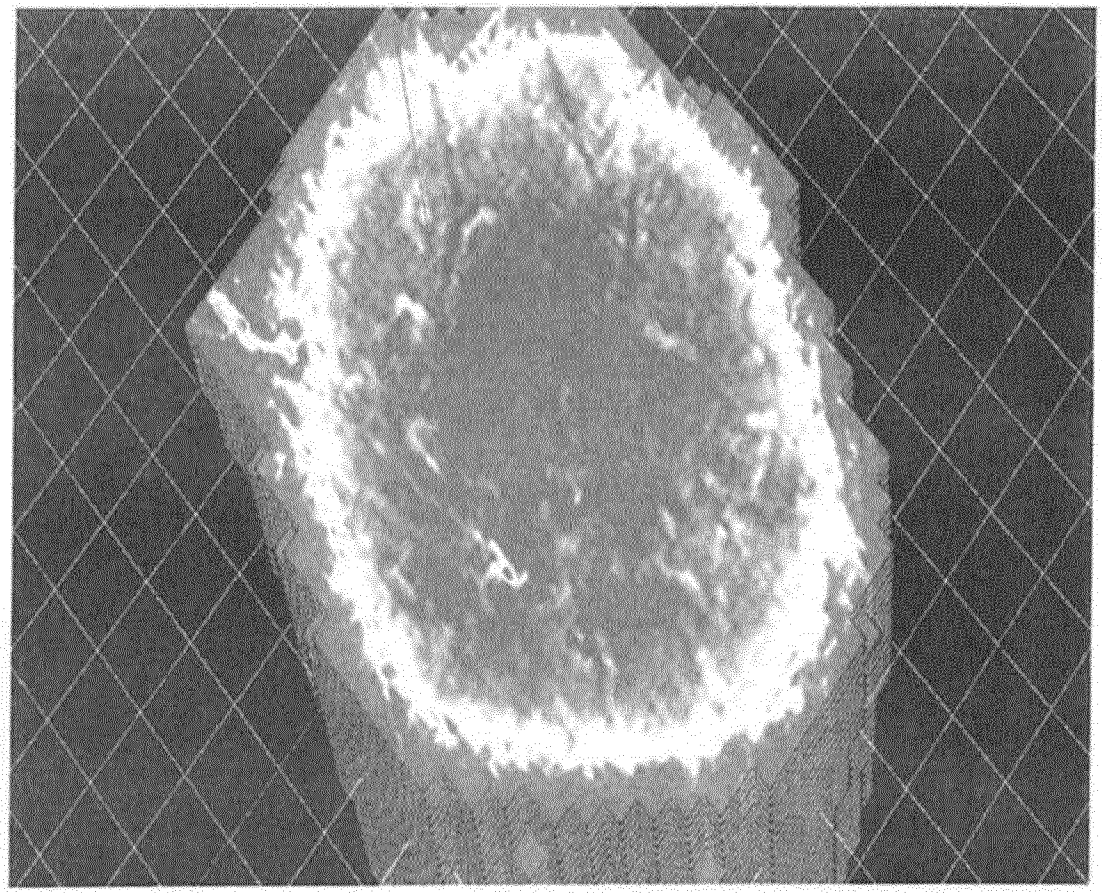

A rectangular lesion image is first converted to the RGBA format by attaching the binary image as an alpha channel. For a gray scale image (single channel image), present channel is repeated three times and the binary image is added as the fourth channel. For a colored (RGB) image, the binary image is added as the fourth channel. The RGBA images for all the layers are loaded in the opengl buffer and displayed using same techniques explained above. The only required change is enabling ALPHA_TEST as shown below,
    glEnable(GL_ALPHA_TEST);    glAlphaFunc (GL_GREATER, 0.0f);

This forces the fragment shader to avoid the background. Thus, an irregular shaped lesion could be displayed in opengl with a shorter turnaround time, as shown in FIG. 16.

Exposure Times for Obtaining Images

Exposure times and values are calculated during the imaging process. After the main control loop receives the trigger event (i.e. the user presses a triggering mechanism that starts the imaging process), the operating system (OS) goes through the following steps to capture eleven high resolution images and send the images to the host computer:

1. Capture a low resolution image (320×256×8-bit) at 430 nm (band 0).

2. Estimate the nominal exposure times for all the bands using the low resolution image.

A "skin_type_adjuster" is calculated to compensate for band-to-band differences that depend on skin type, as determined experimentally:

skin_type_adjuster=(−0.007×blue_band_LED-current× MAXIMUM_AVG/preview-average+1.245)×100/(100+ band_index) where preview-average is the intensity average of the low resolution image (320×256×8-bit).

MAXIMUM_AVG=60, which is the maximum 8-bit intensity average.

3. Optional use of high dynamic range imaging to produce segmentations that are independent of skin pigment:

High dynamic range (HDR) images allow for more than 8 bits per imaging channel to widen the span of the visual dynamic range that an image can capture simultaneously. In one aspect of the present inventive system, HDR can be achieved by first computing the camera's response function (possibly separately for each wavelength, or possibly for all wavelengths taken together). This works by collecting a series of images from the camera, each at different exposure times. A minimum of 3 images is required; however, more images (and at more exposures) will yield a better HDR solution. Using the images and associated exposure times, the camera response is estimated using a known method (See http://www.pauldebevec.com/Research/HDR/debevec-siggraph97.pdf). Then the camera response and a known weighting scheme is used to combine the images into a single HDR image, where each pixel contains values with a 32-bit range (rather than an 8-bit range), capturing a wider range of lighting conditions. Optionally, the 32-bit HDR image can then be mapped back into an 8-bit image which retains the properties of the HDR range using a process called tone-mapping. For this, a bilateral filter with a gamma correction allows for mapping back into a more visible 8-bit imaging range.

Other Example Implementations (1) Providing output that identifies for the pathologist where in the tissue the biopsy slice should be taken, based on the 3D representation of the tissue or of metrics associated with the tissue. The 3D representation can show the pathologist the concentration of malignancy texture (or cellular disorganization), based on which the pathologist can take the slices more precisely than with a collection of 2D images. The 3D rendering can be color-coded at each 3D location with information from the 2D texture images so that the pathologist can visually correlate low and high texture areas geometrically within the 3D representation of the lesion.

(2) Tele-dermatology—allowing for remote consultation, so that the technician operating the optical scanner on the patient is remotely located from the physician, surgeon, or dermapathologist who is viewing and manipulating the 3D image created by the system of the present invention. The remote medical professional can then instruct the technician, for example, on where and how to operate the scanner and where to biopsy the patient's skin or tissue.

(3) Providing volume metrics output that identifies for the dermatologist how deep and vast suspected tissue has penetrated into the skin—based on the 3D representation of the tissue or of metrics associated with the tissue. The 3D representation can show the dermatologist the volume and depth penetration of malignant texture (or cellular disorganization), which can aid the dermatologist with diagnosis more accurately than if the diagnosis was based solely on a collection of 2D images. In addition, the system can calculate a total value for any feature or characteristic identified, such as average or total texture disorganization within a lesion.

(4) Providing surface characteristics and volume metrics output that identifies for the surgeon the topographical area with a field of depth (e.g. topical height variations along with width and length of a designated area of the skin's tissue to be excised)—based on the 3D representation of the tissue or of volume based metrics associated with the tissue. The 3D representation can show the surgeon the volume and depth penetration of malignancy texture (or cellular disorganization), based on which the surgeon can excise more precisely than excision based solely on a collection of 2D images.

(5) Providing metrology—using the 3D representation, the pathologist can select various points on the model and measure the distances between these points precisely. Furthermore, using the interpolated volume, the pathologist can zoom to sub-surface data and observe and measure on sub-surface tissue.

(6) Using the texture image representation, the pathologist can define a cutoff value to identify an area-of-interest, specifying suspicious locations of tissue either on the surface and/or the interior of the lesion. The system can automatically extract these regions of interest and highlight them to easily signify the regions of the lesion to address.

(7) The system can be extended to capture a stream of images at each wavelength over time to produce a 3D video rather than a single set of 3D images. This would allow for a live intervention either directly or remotely, where tools may be tracked and viewed with respect to the lesion in 3D, to further assist in excising tissue and identifying only the portion desired to be removed. This live interaction can be incorporated into the 3D rendering system, showing temporal dynamically changing information during the intervention.

(8) Similar to the classifier mentioned previously which works on the 2D images, 3D geometric analysis can be incorporated to assess correlations between melanoma and non-melanoma lesions.

Possible Other Implementations Other than on Skin Tissue

The system can be used to monitor how wounds heal over time.

If used intra-operatively, the system can be used for monitoring tumors beneath the surface of organs, which would eliminate the need for expensive CT/MRI scans which are difficult or impossible to use intra-operatively. This would allow for better situational awareness during a biopsy or during removal of cancerous tissue.

Often during emergency situations, ER physicians are trying to locate the source of a bleed which is internal and difficult to isolate. Being able to scan to sub-surface levels of the body can help to more quickly isolate the source of bleeds in such and other emergency situations.

Cochlear applications. The small structures of the ear, internally and externally, can be visualized.

Pathology imaging of biopsy samples. When applied to an in-vitro sample such as paraffin, OSI can be used to determine the location of sectioning the tissue in order to ensure the most disorganized tissue is reviewed by the pathologist under the microscope. The technique can also be applied to understand how much of the lesion has been discarded by imaging both sides of a paraffin sample after sectioning, thus evaluating the performance of the grosser. Similarly, the imaging can be used to determine how far into the paraffin the current lesion has been sectioned.

Surgery biopsy and tissue related image guidance. The imaging of the present invention may be used either as a live video feed or through images in order to guide surgeons and physician in excisions by determining features such as lesion volume and area of disorganization. In addition, the ability to image surrounding tissue allows the physician to determine a baseline of tissue features, thus utilizing imaging to guide margins when visually unattainable.

Ex vivo imaging of tissue. A 3D image sample of a lesion may be obtained after it has been excised from the body to help grossers image the portion of the lesion for sectioning prior to setting the lesion in paraffin.

Determining margins for surgery, both pre and post excision. A 3D image may be used to visualize any selected remaining tissue "left behind" after surgery or may be used for surgery planning to identify margin for excision.

Other applications may be in guiding surgeons and interventionists in the evaluation of other tissue constructs other than potentially cancerous lesions. Interventional cardiologists may benefit from examining vessel wall tissue organization as well as myocardial wall cell construct. General surgeons may benefit from using the inventive technology to examine tissue in exploratory procedures. Plastic and Aesthetic physicians may use the images created to evaluate skin properties before and after aesthetic procedures. Digital visualization of tissue vascularity, construct of fibrin and collagen, angiogenesis, hair follicles, depth of wrinkles, and other dermal features may assist in documentation of wrinkles and enable measurement of treatment outcomes.

The description of certain embodiments of this invention is intended to be illustrative and not limiting. Therefore, although the present invention has been described in relation to particular embodiments thereof, many other variations and other uses will be apparent to those skilled in the art. It is understood therefore that the present invention is not limited by the specific disclosure herein, but only by the broadest scope of the appended claims. Possible and known variations for the systems and methods described herein can be implemented in a number of different ways as long as the operation of the inventive system and method falls within the appended claims.

The invention claimed is:

1. A method of non-destructive imaging of an anomalous tissue in a region of interest, the method comprising:

a) illuminating the region of interest with light in multiple spectral bands, each of the spectral bands being associated with a respective predetermined depth value in the tissue;
b) capturing, with a camera, a two-dimensional image of the region of interest under illumination by the light in each of the spectral bands;
c) identifying a first anomaly area containing the anomalous tissue within the image of a topmost spectral band;
d) applying the first anomaly area to each of the images of the spectral bands that are deeper than the topmost;
e) segmenting each of the images of the deeper spectral bands, one by one, wherein the segmenting automatically identifies pixels belonging to the anomalous tissue, isolating a shape of the anomalous tissue;
f) halting the segmentation of the images of the deeper spectral bands when the anomalous tissue is no longer detected;
g) determining a set of data points for each of the segmented images, wherein each set of data points has lateral position data defining a position within a respective spectral plane at a respective depth value;
h) transforming each set of data points for each segmented image into a single three-dimensional anomaly volume by additionally applying the predetermined depth value to each of the respective set of data points for each segmented image, yielding transformed sets of data points, respectively, each data point within each of the transformed sets of data points thereby assigning lateral position and depth data values;
i) rendering an image of the three-dimensional anomaly volume by plotting the transformed sets of data points; and
j) displaying the rendered image to a user.

2. The method of claim 1, wherein the segmentation comprises segmenting the image of the deeper spectral bands into a binary image.

3. The method of claim 1, wherein the camera includes optical components and a sensor.

4. The method of claim 3, wherein of each of the predetermined depth values is based on the respective spectral band of light and optical calibration of the camera.

5. The method of claim 3, wherein the sensor is a complementary metal oxide semiconductor-type sensor.

6. The method of claim 1, wherein the multiple spectral bands of light are provided by one or more light-emitting diodes.

7. The method of claim 1, further comprising rendering texture within the image of the three-dimensional anomaly volume by additionally processing at least one of the spectral band anomaly areas with a pre-defined computation, in order to illustrate differences in spatial gradient.

8. The method of claim 1, wherein:
the topmost spectral band is a wavelength of light of about 430 nm and the first depth value is about 0.4 mm.

9. The method of claim 1 wherein identifying the region of interest comprises the following steps:
performing an Expectation Maximization (EM) and Gaussian Mixture Model (GMM) clustering of the pixels;
automatically dividing all of the pixels into the anomalous tissue or a background and assigning a conditional probability at every pixel for being in an anomalous tissue class or a non-anomalous tissue class;
selecting a threshold on a final probability;
accumulating a Cumulative Distribution Function; and
cutting off the threshold to produce a bounding box for the anomalous tissue.

10. The method of claim 9 further comprising adding a Gaussian weighting kernel to the EM/GMM model to eliminate spurious pixels.

11. A system for non-destructive imaging of an anomalous tissue in a region of interest, comprising:
a) a source of illumination of light in multiple spectral bands;
b) a camera for acquiring digital images of the region of interest based on the light re-emitted from the region of interest when illuminated at multiple each of the at least two spectral bands, the digital image comprising digital signals whose values are a function of a condition of the region of interest;
c) a memory for storing the digital images;
d) a digital processor adapted and configured for
i) processing the digital image of a topmost spectral band stored in memory and computing an estimated value of parameters which are a function of the processed topmost image to define a first anomaly area;
ii) processing and applying the first anomaly area to each of the deeper spectral band images;
iii) segmenting each of the images of the deeper spectral bands, one by one, wherein the segmenting automatically identifies pixels belonging to the anomalous tissue, isolating a shape of the anomalous tissue;
iv) halting the segmentation of the images of the deeper spectral bands when the anomalous tissue is no longer detected;
v) determining a set of data points for each of the segmented images, wherein each set of data points has lateral position data defining a position within a respective spectral plane at a respective depth value;
vi) transforming the each set of data points for each segmented image into a single three-dimensional anomaly volume; and
vii) rendering an image of the three-dimensional anomaly; and
e) a display adapted and configured for displaying the rendered image to a user.

12. A non-transitory computer-readable storage medium comprising a plurality of instructions configured to execute on at least one computer processor to enable the computer processor to:
a) initiate illumination of a region of interest with light in multiple spectral bands, each of the spectral bands being associated with a respective predetermined depth value in the tissue;
b) initiate capture, with a camera, a two-dimensional image of the region of interest under illumination by the light in each of the spectral bands;
c) identify a first anomaly area containing the anomalous tissue within the image of a topmost spectral band;
d) apply the first anomaly area to each of the images of the spectral bands that are deeper than the topmost;
e) segment each of the images of the deeper spectral bands, one by one, wherein the segmenting automatically identifies pixels belonging to the anomalous tissue, isolating a shape of the anomalous tissue;
f) halt the segmentation of the images of the deeper spectral bands where the anomalous tissue is no longer detected;

g) determine a set of data points for each of the segmented images, wherein each set of data points has lateral position data defining a position within a respective spectral plane at a respective depth value;
h) transform each set of data points for each segmented image into a single three-dimensional anomaly volume by additionally applying the predetermined depth value to each of the respective setoff data points for each segmented image, yielding transformed sets of data points, respectively, each data point within each of the transformed sets of data points thereby assigning lateral position and depth data values;
i) render an image of the three-dimensional anomaly volume by plotting the transformed sets of data points; and
j) display the rendered image to a user.

* * * * *

UNITED STATES PATENT AND TRADEMARK OFFICE
CERTIFICATE OF CORRECTION

PATENT NO. : 10,004,403 B2
APPLICATION NO. : 14/837120
DATED : June 26, 2018
INVENTOR(S) : DeBernardis et al.

It is certified that error appears in the above-identified patent and that said Letters Patent is hereby corrected as shown below:

Please delete Patent No. 10,004,403 B2 in its entirety and insert Patent No. 10,004,403 B2 as shown on the attached pages.

Signed and Sealed this
Twenty-ninth Day of October, 2019

Andrei Iancu
*Director of the United States Patent and Trademark Office*

(12) United States Patent
DeBernardis et al.

(10) Patent No.: US 10,004,403 B2
(45) Date of Patent: Jun. 26, 2018

(54) THREE DIMENSIONAL TISSUE IMAGING SYSTEM AND METHOD

(71) Applicants: Frank A. DeBernardis, Ridgewood, NJ (US); Natalie J. Tucker, New York, NY (US); Austin D. Reiter, Great Neck, NY (US); Minhaz Palasara, New York, NY (US)

(72) Inventors: Frank A. DeBernardis, Ridgewood, NJ (US); Natalie J. Tucker, New York, NY (US); Austin D. Reiter, Great Neck, NY (US); Minhaz Palasara, New York, NY (US)

(73) Assignee: Mela Sciences, Inc., Irvington, NY (US)

( * ) Notice: Subject to any disclaimer, the term of this patent is extended or adjusted under 35 U.S.C. 154(b) by 74 days.

(21) Appl. No.: 14/837,120

(22) Filed: Aug. 27, 2015

(65) Prior Publication Data
US 2016/0058288 A1 Mar. 3, 2016

Related U.S. Application Data

(60) Provisional application No. 62/042,858, filed on Aug. 28, 2014.

(51) Int. Cl.
*A61B 5/00* (2006.01)
*G06T 17/10* (2006.01)

(52) U.S. Cl.
CPC .......... *A61B 5/0077* (2013.01); *A61B 5/0075* (2013.01); *A61B 5/444* (2013.01); *G06T 17/10* (2013.01); *A61B 5/742* (2013.01); *A61B 5/748* (2013.01); *A61B 2560/0475* (2013.01); *G06T 2210/41* (2013.01)

(58) Field of Classification Search
CPC ...... A61B 5/0077; A61B 5/0075; A61B 5/444; A61B 5/742; A61B 5/748; A61B 2560/0475; G06T 17/10; G06T 2210/41
See application file for complete search history.

(56) References Cited

U.S. PATENT DOCUMENTS 6,081,612 A * 6/2000 Gutkowicz-Krusin ........... A61B 5/0071 382/128
6,208,749 B1 * 3/2001 Gutkowicz-Krusin ........ 356/303
(Continued)

OTHER PUBLICATIONS

PCT Search Report, dated Nov. 24, 2015, pp. 1-8, US.

*Primary Examiner* — Catherine Voorhees
(74) *Attorney, Agent, or Firm* — Carter Ledyard & Milburn LLP

(57) ABSTRACT

Multispectral digitized images are provided by utilizing 2 or more spectral bands, providing images and information regarding a pigmented or other differentiated tissue sample at differing depths. The images are transformed to enhance morphological patterns characteristic of melanoma, such as the statistical properties of the pigment network, image texture or homogeneity, and the lesion reflectance, in order to provide information about lesion morphology at different depths. The images can also be processed and transformed to extract features such as blood volume saturation, oxygen saturation, or other characteristics that can be identified based on differential reflectance or absorption of light.

12 Claims, 18 Drawing Sheets
(18 of 18 Drawing Sheet(s) Filed in Color)

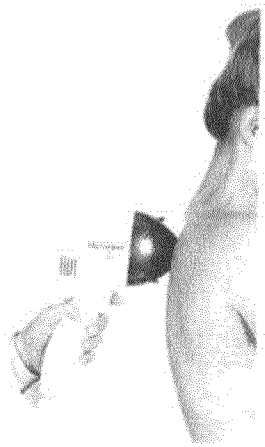

US 10,004,403 B2
Page 2

(56) References Cited

U.S. PATENT DOCUMENTS

| | | | |
|---|---|---|---|
| 7,747,055 B1* | 6/2010 | Vining | A61B 6/466 345/419 |
| 7,978,346 B1 | 7/2011 | Riza | |
| 2001/0039422 A1* | 11/2001 | Carol | A61B 90/10 606/130 |
| 2010/0042004 A1* | 2/2010 | Dhawan | A61B 5/0059 600/476 |
| 2011/0304705 A1* | 12/2011 | Kantor | A61B 5/0059 348/49 |
| 2012/0130232 A1* | 5/2012 | Markowitz | A61B 5/0422 600/424 |
| 2014/0049614 A1* | 2/2014 | Yamada | H04N 5/2226 348/46 |

* cited by examiner

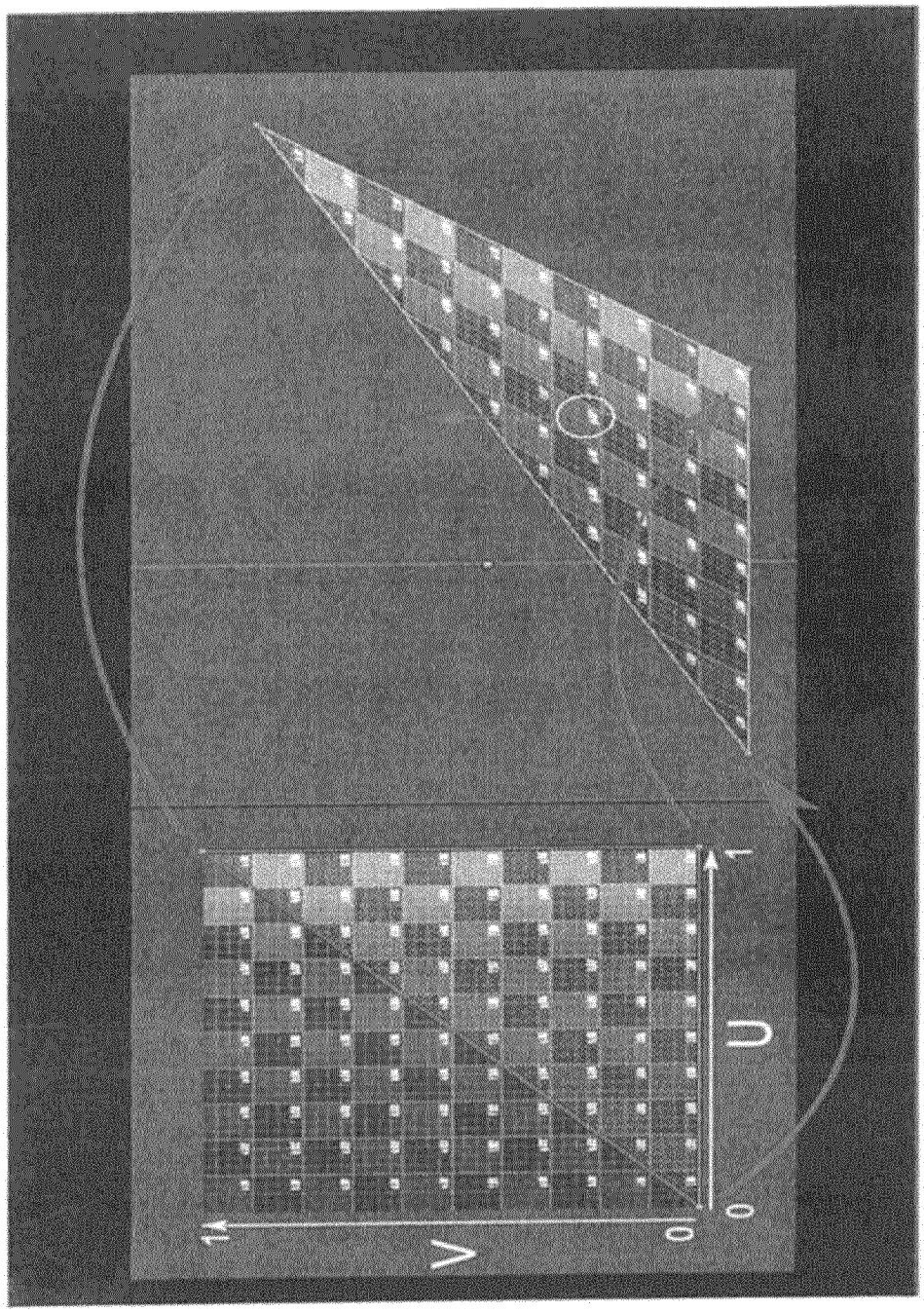

THREE DIMENSIONAL TISSUE IMAGING SYSTEM AND METHOD

CROSS-REFERENCE TO RELATED APPLICATIONS

This application is related to, and claims the benefit of, U.S. Provisional Patent Application Ser. No. 62/042,858, filed Aug. 28, 2014, which is incorporated herein by reference.

FIELD OF THE INVENTION

The present invention relates to systems and methods for optical spectral imaging of tissue in three dimensions using multiple spectrums of light.

BACKGROUND OF THE INVENTION

Conventionally, lesion information is obtained via surface visual analysis by the dermatologist. This limited information results in 20-30% of early melanomas going undetected. The estimated total direct cost associated with the treatment of melanoma in 2010 in the United States due to lack of early detection was $2.36 billion, with 65% of total cost going to continued care and another 20% of total cost going to the last year of life.

To see below the topmost layer of skin, a dermatoscope with a lighted magnifier may be used, but the image is limited to the top few layers of the surface of the skin. Additional imaging tools are available to the market, but none display or quantify the morphological disorganization characteristics as obtained from below the surface of the skin.

In the field of surgery and dermatology, lesion volume and location of disorganized tissue is critical in determining that the proper area is removed through biopsy for subsequent review by the pathologist. Current teaching techniques recommend utilizing a dermatoscope to select sampling location for biopsy. In a study by Dr. Hsu and Dr. Cockerell, 1123 histologically confirmed melanomas were reviewed and found significant diagnostic discrepancy between initial punch biopsies and re-excision specimens. While the excisional biopsy and sauceration shave biopsy demonstrated near 100% accuracy, punch technique was only 86.5% accurate. The paper reveals, "Due to the inherent intralesional heterogeneity of cutaneous melanoma, small punch biopsies may not always obtain representative specimens and may subject the patient to significant risk of misdiagnosis."

Further misdiagnosis occurs among pathologists who either over diagnose or under diagnose a lesion. This is represented in a number of papers where discordance in dermatopathology among reviewers has been reported ranging from 14.3%-62.0%. As a result, typically only 2-5% of the total lesion is examined by the pathologist, and the remaining tissue sample is archived or discarded. This technique results in additional sections being ordered by the dermatologist if he or she believes the diagnosis is not correct, and perhaps the area of interest was not reviewed by the pathologist due to ineffective sectioning. Currently, no imaging device is known that offers the capability to guide sectioning as performed by a pathologist and his or her grossers, and this lack of image guidance in determining which areas of the lesion to section, in addition to subjective evaluation under the microscope, puts patients at undue risk.

For surgeons, ultrasound is the only medium for imaging a lesion below the skin in an attempt to view total volume. Unfortunately, ultrasound is unreliable on pigmented lesions and is difficult to read.

Recently, the MelaFind® Optical Imaging and Analysis Device has become available following FDA approval. It is a multispectral digital skin lesion analysis system used in the detection of melanoma among atypical skin lesions. The device uses light to image the skin through a layer of isopropyl alcohol to generate a classifier score result that provides information on the likelihood of a lesion being melanoma based on predefined image analysis algorithms. The device is used when a dermatologist chooses to obtain additional information on a decision to biopsy.

The MelaFind device currently utilizes multispectral images from 10 wavelengths of light, 430 nm to 950 nm, and produces colorless melanin absorption based images utilizing 10 spectral bands. These images however are not transformed into a 3-dimensional volumetric rendering of the lesion, and require interpretation by the user on the areas between each vertical layer image. The operation of some aspects of the MelaFind device are disclosed in U.S. Pat. Nos. 6,081,612 and 6,208,749, which are hereby incorporated by reference in this application in their entirety.

SUMMARY OF THE INVENTION

Multispectral digitized images are provided by utilizing 2 or more spectral bands, providing images and information regarding a pigmented or other differentiated tissue sample at differing depths. The penetration depth into an object for different bands is based on the fact that the longer the wavelength of light, the deeper the light penetrates tissue.

The images are transformed to enhance morphological patterns characteristic of melanoma, such as the statistical properties of the pigment network, image texture or homogeneity, and the lesion reflectance, in order to provide information about lesion morphology at different depths. The images can also be processed and transformed to extract features such as blood volume saturation, oxygen saturation, or other characteristics that can be identified based on differential reflectance or absorption of light.

The 2D mesh images obtained at each wavelength are then used to create 3D representations of a tissue sample through voxels. The 2D mesh images can be turned into a 3D voxel representation and vice versa. Area and volume calculations on these representations can be provided as guidance for excision or for visualizing specific areas of disorganization or other desired features or characteristics within a 3-dimensional tissue sample.

One possible indication for use of the 3D Optical Spectral Imaging technology disclosed herein may be for Image Guided Tissue Sampling, the intent of which is to sample the most disorganized area of the lesion, thus reducing sampling error. A second possible indication for use of the Optical Spectral Imaging technology may be for Image Guided Tissue Sectioning for dermatopathologists, the intent of which is to select the most disorganized area of the lesion to be used for evaluation by the pathologist under the microscope. A third possible indication for use of the Optical Spectral Imaging technology may be for Image Guided Biopsies, the intent of which is to increase surgery efficiency by viewing the 3-dimensional volume and construct of the lesion for margin guidance. As a result, the present invention is intended to improve the standard of care for biopsies, increase dermatopathology sectioning efficiency and accuracy, as well as aid in the surgeon's excision quality of removed tissue.

Other applications may be in guiding surgeons and interventionists in the evaluation of other tissue constructs. Interventional cardiologists may benefit from examining vessel wall tissue organization as well as myocardial wall cell construct. General surgeons may benefit from using the technology to examine tissue in exploratory procedures.

Further indications are set forth below.

BRIEF DESCRIPTION OF THE DRAWINGS

FIG. 1, also referred to as Image 1, illustrates the MelaFind optical scanner being held by a medical professional or technician against a region of interest on the back of a patient.

Figure 2:
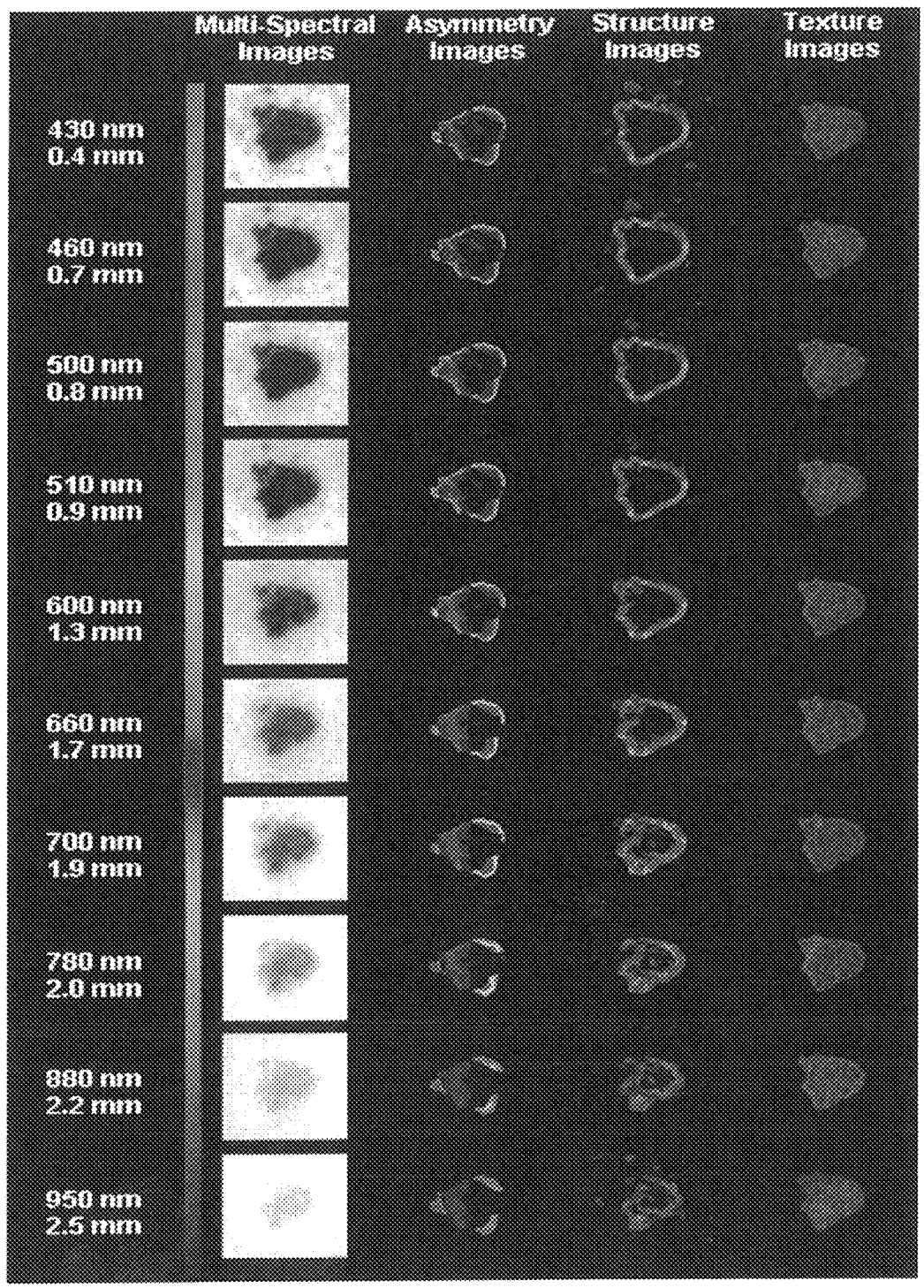
FIG. 2, also referred to as Image 2, shows the wavelengths used to obtain data from various depths below the surface of the skin and examples of the images that can be created using the existing MelaFind system.

FIG. 2, also referred to as Image 2, shows the wavelengths used to obtain data from various depths below the surface of the skin and examples of the images that can be created using the existing MelaFind system.

Figure 3:
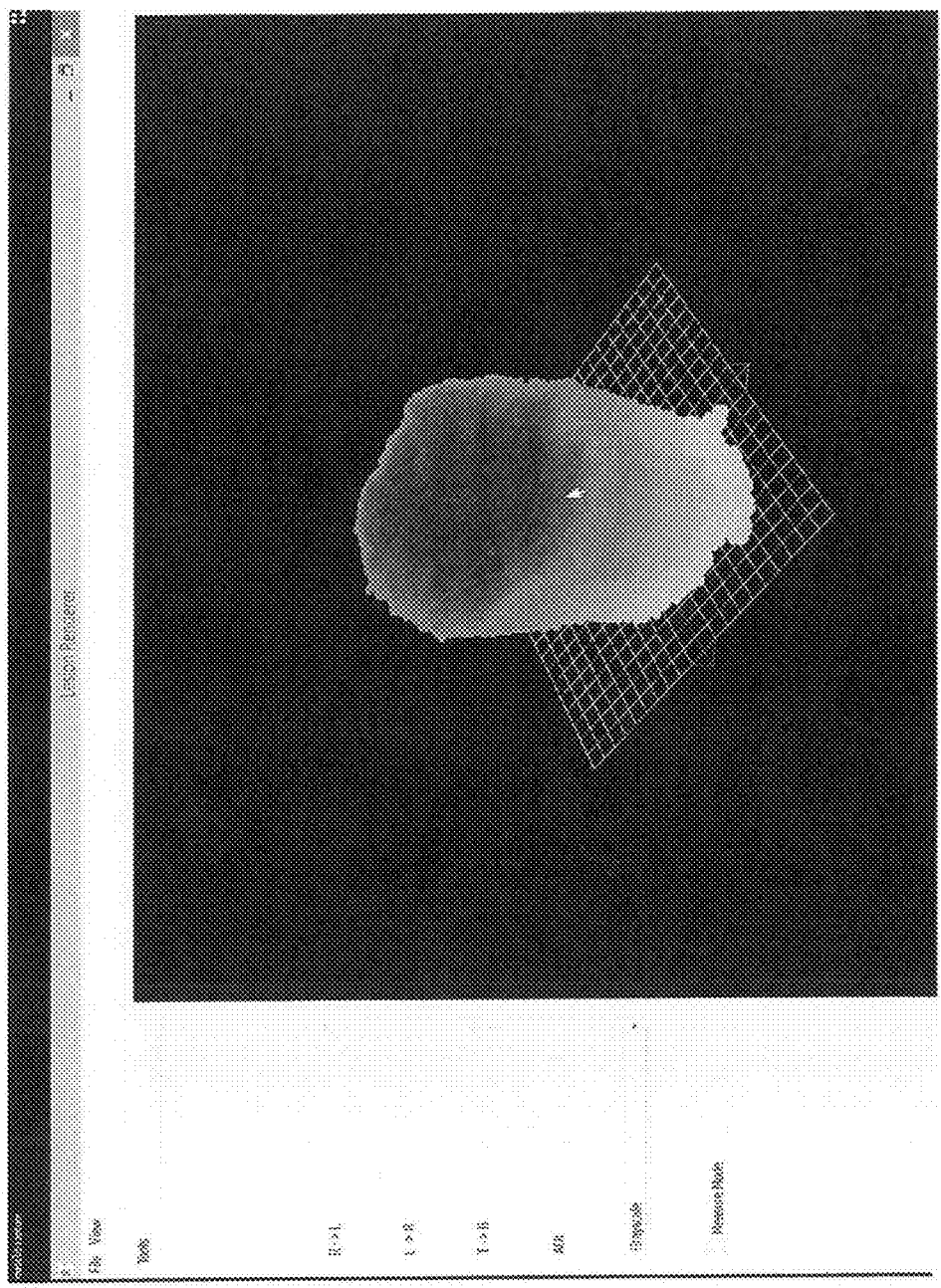
FIG. 3, also referred to as Image 3, shows a multispectral gray-scale image of a lesion created by the present inventive system.

FIG. 3, also referred to as Image 3, shows a multispectral gray-scale image of a lesion created by the present inventive system.

Figure 4:
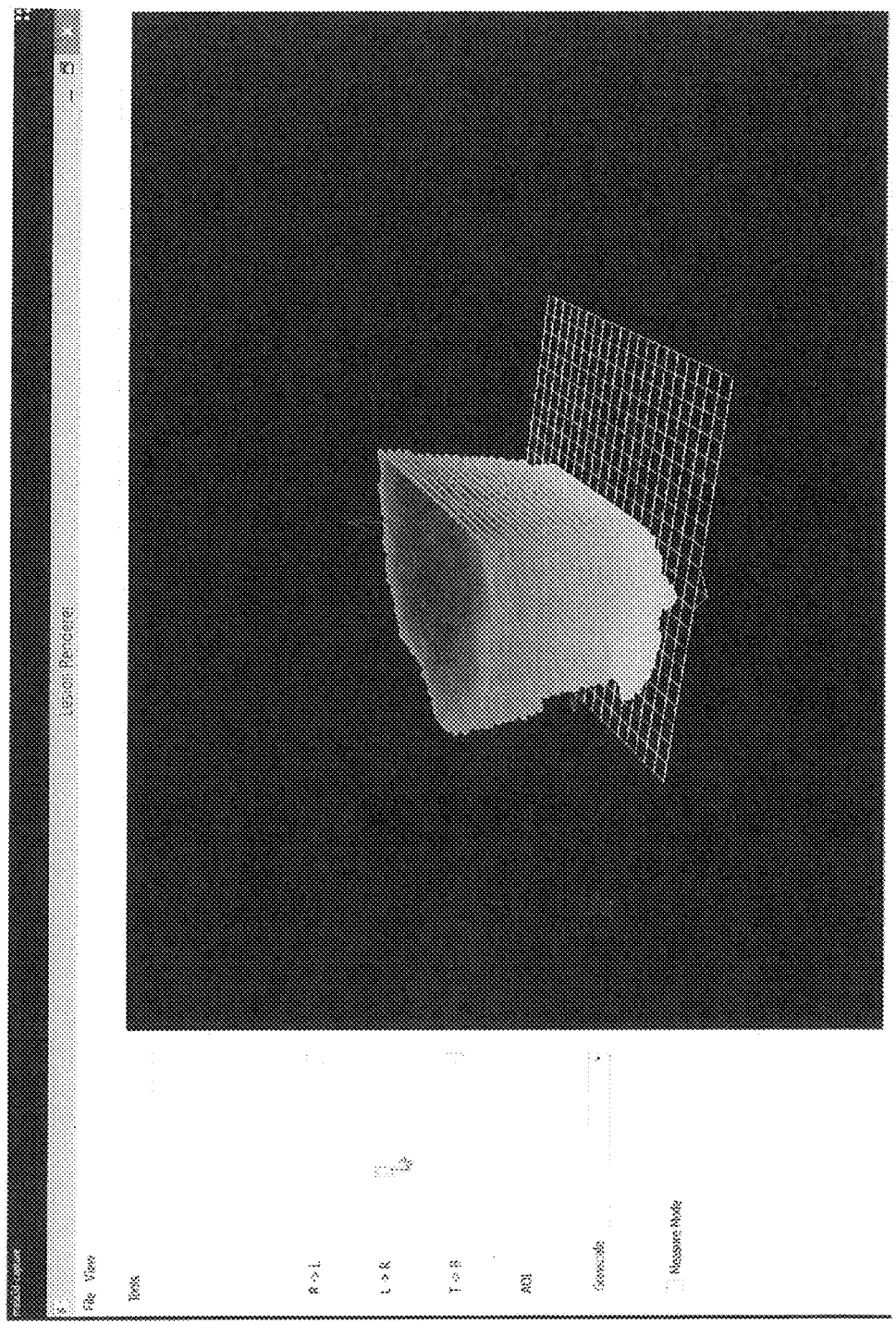
FIG. 4, also referred to as Image 4, is a 3D gray-scale image created by the present inventive system with the right side of the lesion removed to show the interior of the lesion.

FIG. 4, also referred to as Image 4, is a 3D gray-scale image created by the present inventive system with the right side of the lesion removed to show the interior of the lesion.

Figure 5:
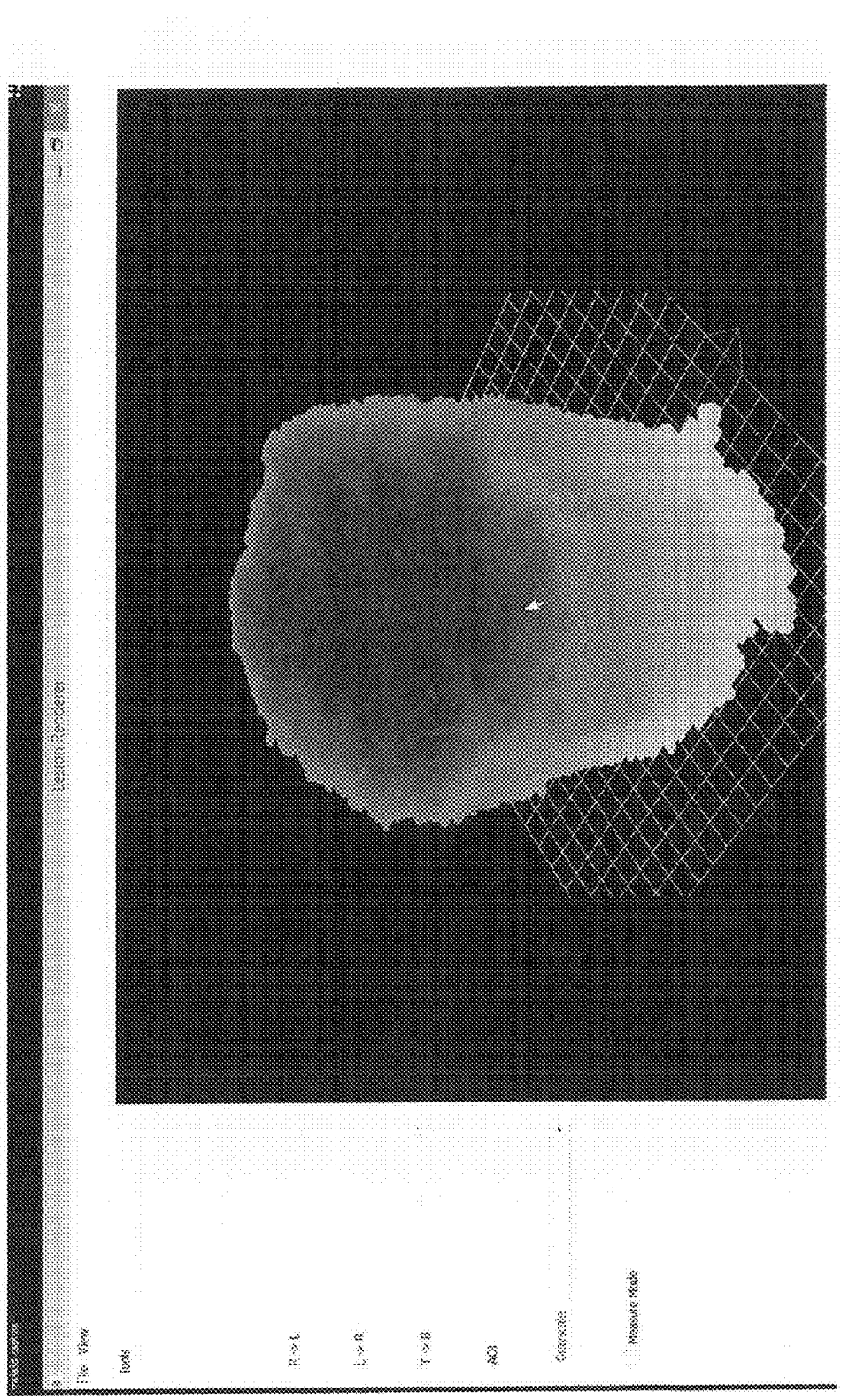
FIG. 5, also referred to as Image 5, shows a zoomed-in 3D gray-scale image created by the present inventive system FIG. 6, also referred to as Image 6, is a 3D gray-scale image created by the present inventive system with the top of the lesion removed.
Figure 6:
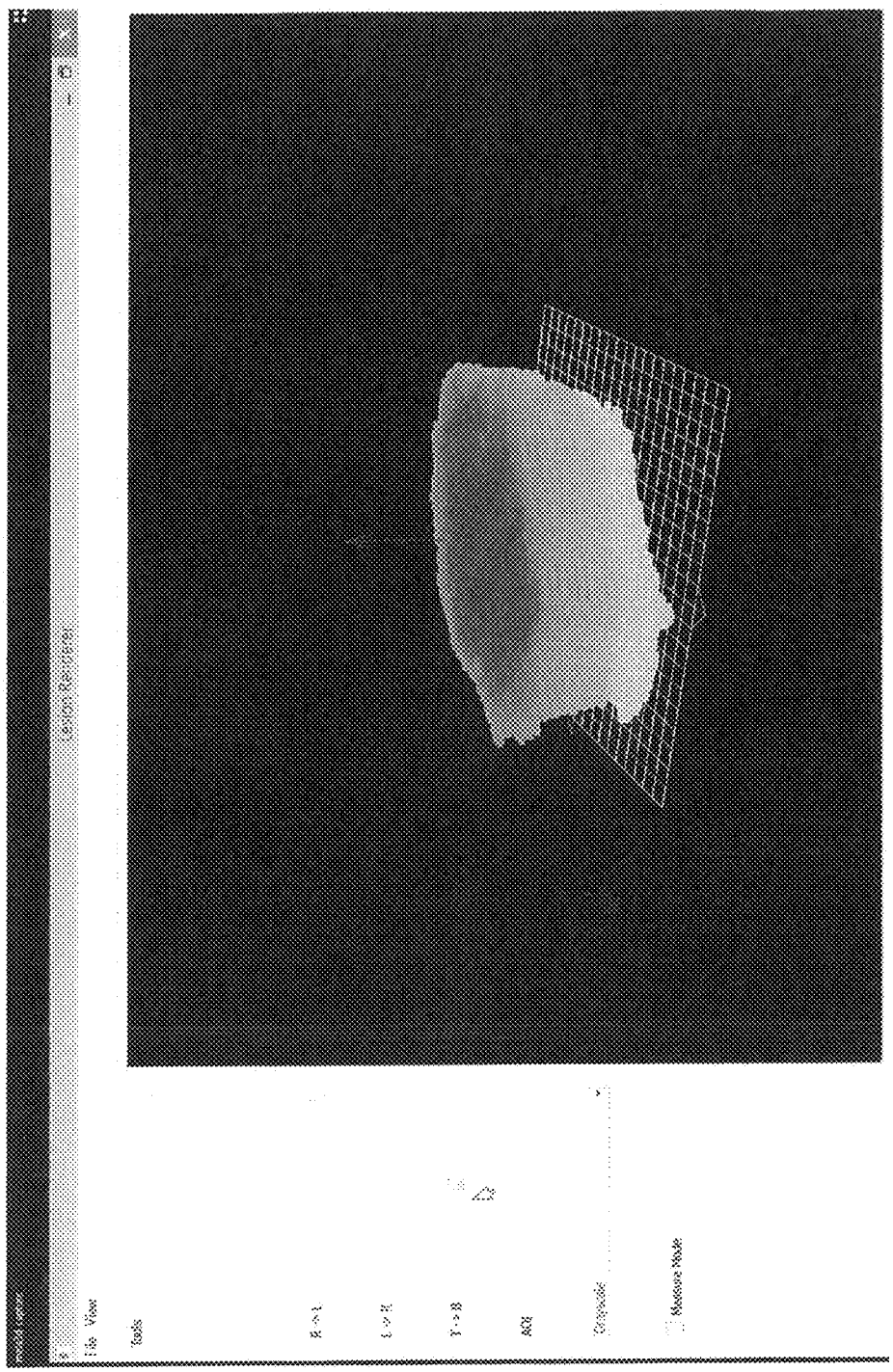

FIG. 5, also referred to as Image 5, shows a zoomed-in 3D gray-scale image created by the present inventive system FIG. 6, also referred to as Image 6, is a 3D gray-scale image created by the present inventive system with the top of the lesion removed.

Figure 7:
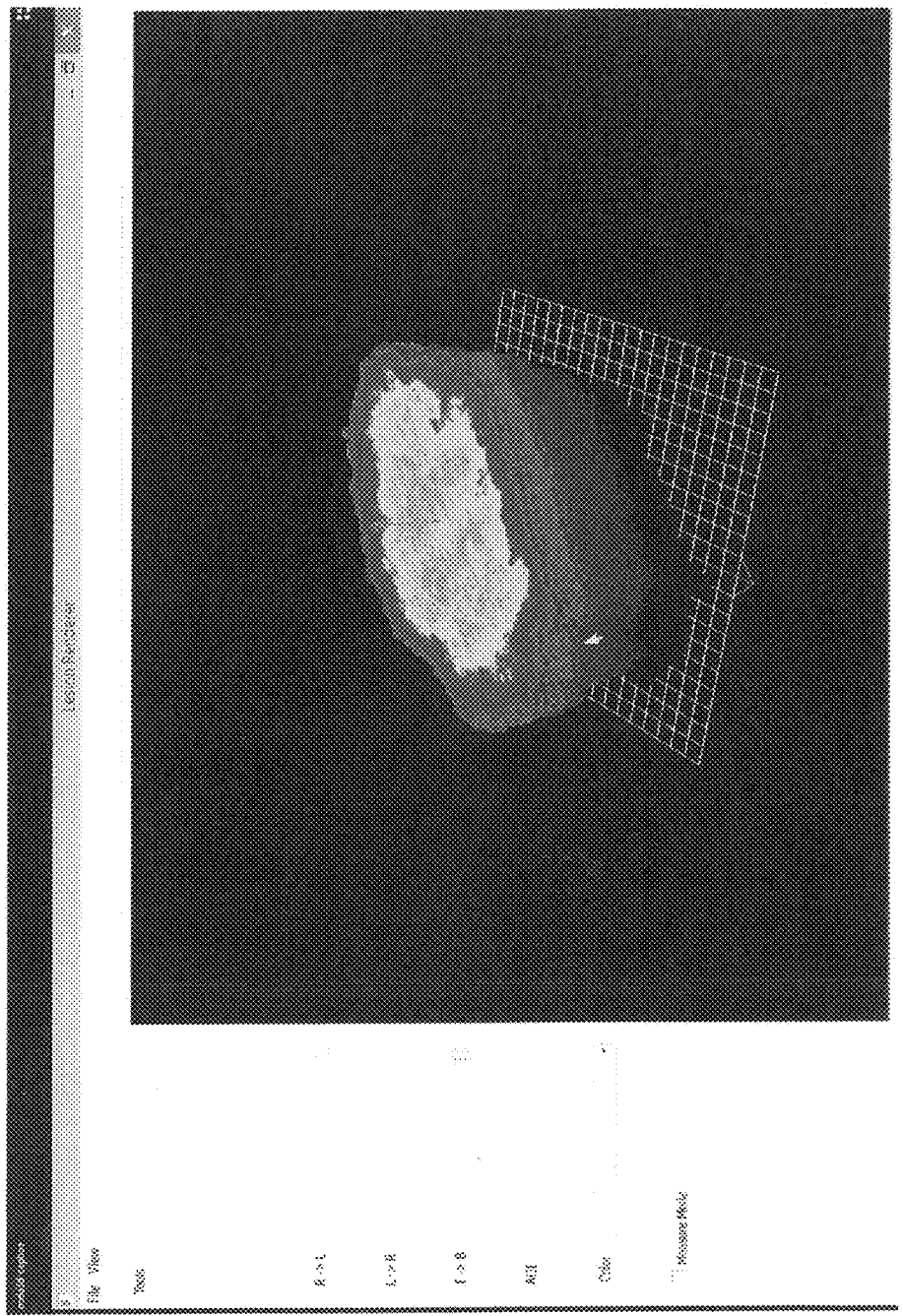
FIG. 7, also referred to as Image 7, shows a 3D image of a lesion colorized according to "texture" created by the present inventive system.

FIG. 7, also referred to as Image 7, shows a 3D image of a lesion colorized according to "texture" created by the present inventive system.

Figure 8:
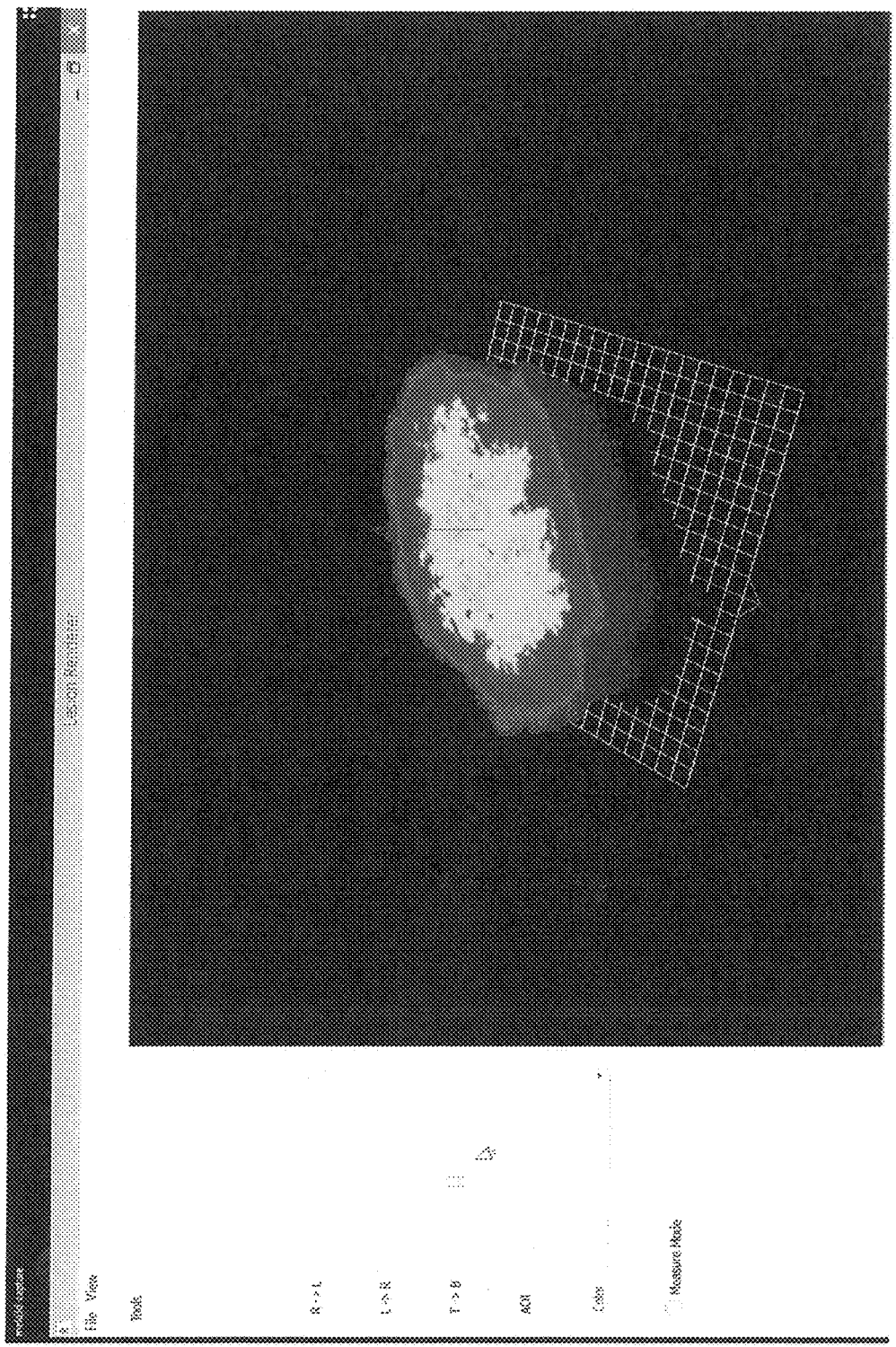
FIG. 8, also referred to as Image 8, shows the lesion of FIG. 7 with the top "sliced" off to show the interior.

FIG. 8, also referred to as Image 8, shows the lesion of FIG. 7 with the top "sliced" off to show the interior.

Figure 9:
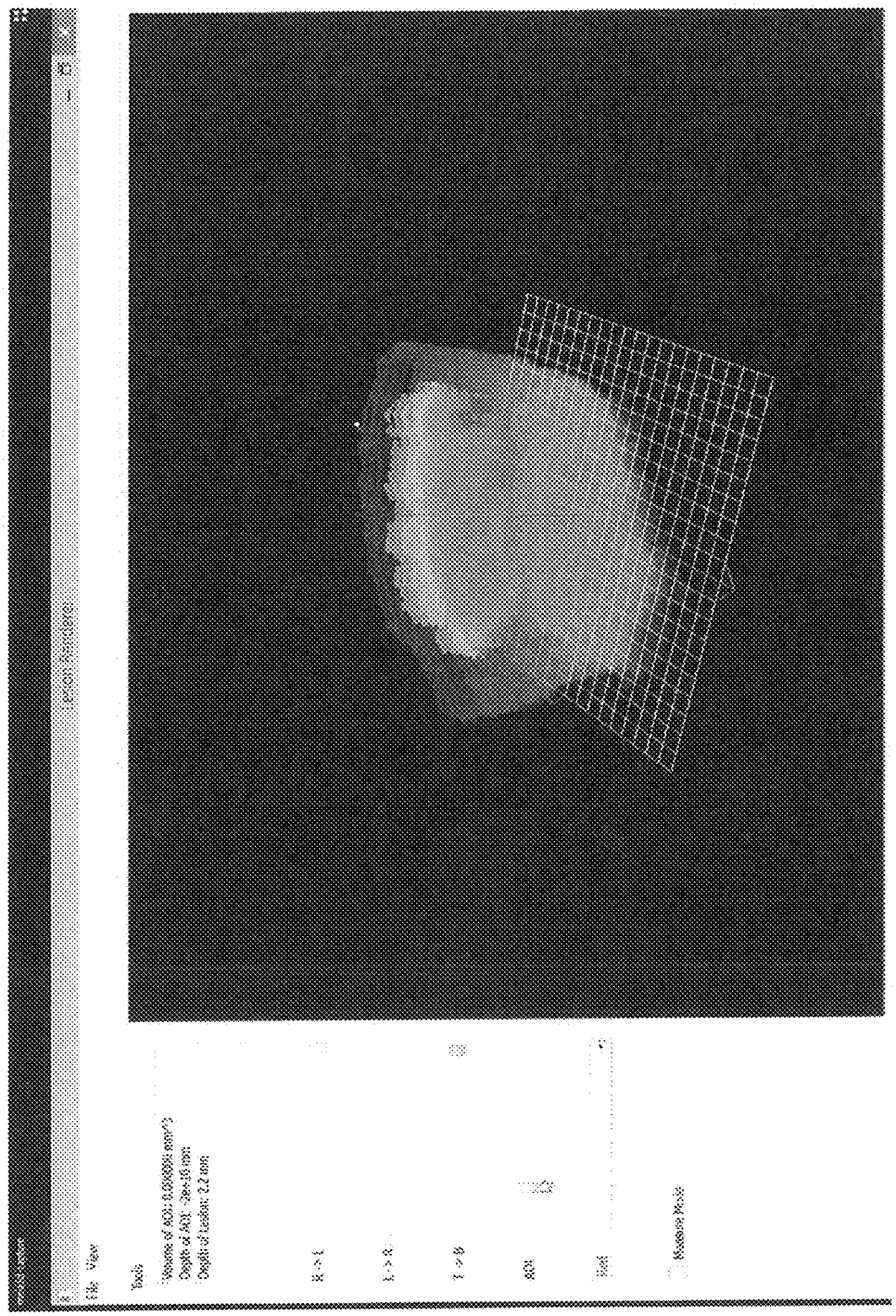
FIG. 9, also referred to as Image 9, shows a 3D image of a lesion created by the present inventive system where the threshold for showing "texture" has been adjusted.

FIG. 9, also referred to as Image 9, shows a 3D image of a lesion created by the present inventive system where the threshold for showing "texture" has been adjusted.

Figure 10:
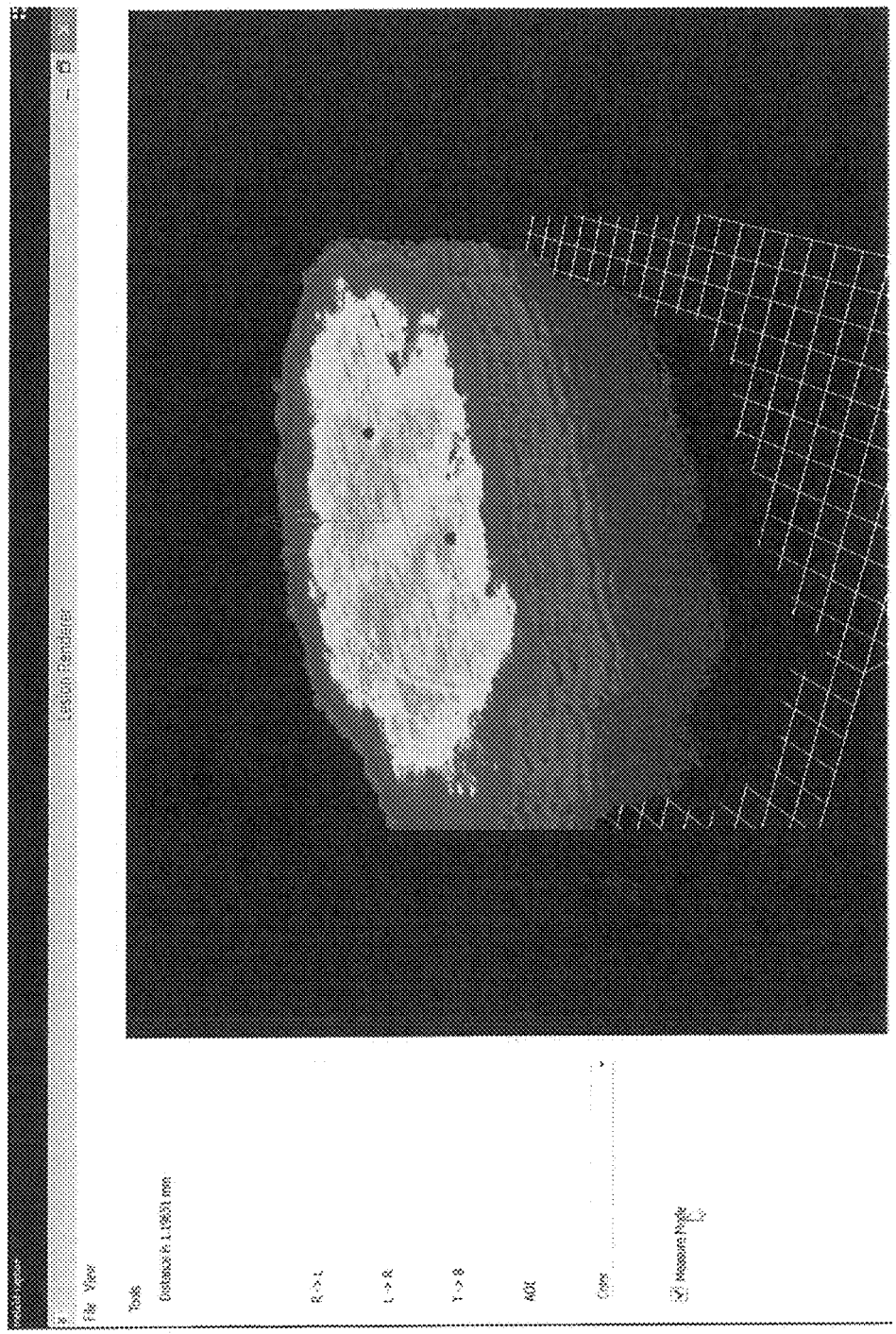
FIG. 10, also referred to as Image 10, shows the operation of the measuring mode in the Lesion Renderer embodiment of the present invention.

FIG. 10, also referred to as Image 10, shows the operation of the measuring mode in the Lesion Renderer embodiment of the present invention.

FIG. 11 illustrates texture to plane mapping in the OpenGL embodiment of the present invention.

FIGS. 12A and 12B illustrates a complete lesion point cloud in the OpenGL embodiment of the present invention.

FIGS. 13A and 13B illustrates the variance of an intermediate pixel (at a specific width and height) in a lesion as selected by user in the OpenGL embodiment of the present invention.

FIG. 14 illustrates a segmented lesion rendered in the OpenGL embodiment of the present invention in which the black region is background.

Figure 15:
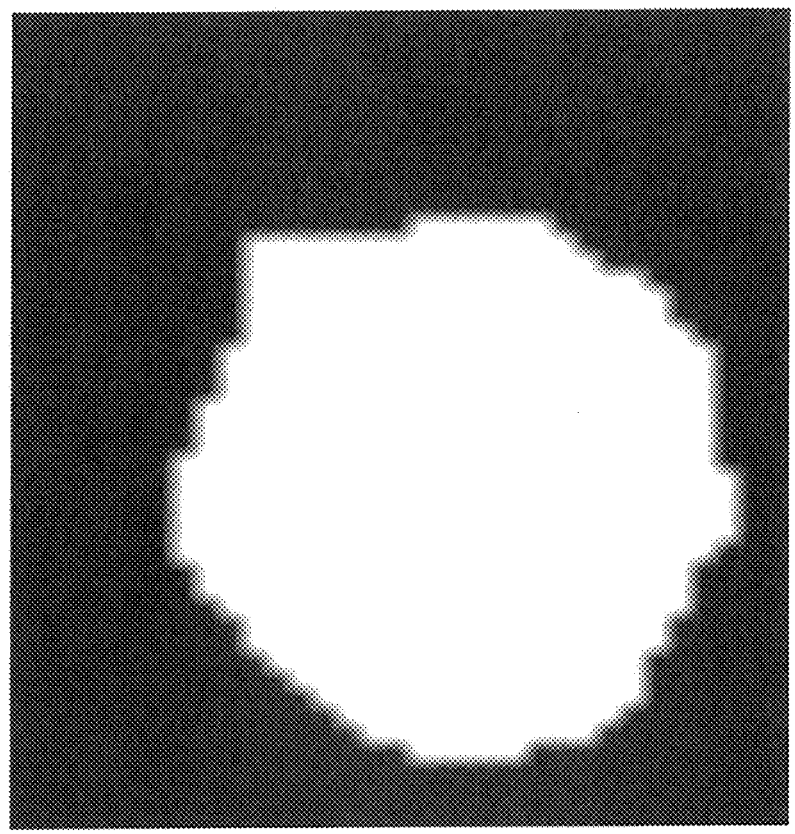
FIG. 15 illustrates a binary mask used to define foreground in an image rendered in the OpenGL embodiment of the present invention.

FIG. 15 illustrates a binary mask used to define foreground in an image rendered in the OpenGL embodiment of the present invention.

FIG. 16 illustrates a segmented lesion rendered in the OpenGL embodiment of the present invention.

DETAILED DESCRIPTION

Overview

Medical diagnostic imaging is performed to acquire data about the state of human body parts, including internal organs as well as skin, which is an external organ. In the case of skin, the imaging with visible and near infrared light can be performed in vivo or in vitro to a depth of approximately 2.5 millimeters. In the current invention of Optical Spectral Imaging ("OSI"), the data acquired through this multispectral imaging is processed and analyzed to derive metrics of small volume elements ("voxels") to a depth of approximately 2.5 millimeters, and to provide three dimensional ("3D") representations thereof. Such imaging information can provide metrics and conclusions about the tissue being examined. OSI may assist in improving discordance levels among pathologists by communicating the area of interest to the pathologist to target while sectioning and diagnosing the lesion, with additional sections being reviewed for high-risk lesions or as deemed necessary by the dermatologist.

The system initially yields 10 images, each resulting from a different wavelength and located at an estimated perpendicular depth from the optical center of the camera. Each image contains a slightly more submersed (from the surface of the skin) image of a lesion than the previous. The algorithm employed begins with an image segmentation procedure which automatically identifies which pixels belong to the lesion (and which pixels belong to the background, or normal tissue) at each depth slice, or image layer, of the system. Since the shape of the lesion will change, however slightly, as you move further into the skin, accurate image segmentation is essential to properly capturing the shape of the lesion in 3D. The segmentation procedure yields formation of binary images at each depth slice, meaning an image comprising pixels that can have only 1 of 2 values: 255 if it is part of the lesion, and 0 otherwise. Each pixel location is also defined in terms of 3D spacing because of the known camera calibration of the system, and so 20 microns of separation can be assumed pixel-to-pixel. Using the estimated depth values of each slice, the binary images are transformed into a 3D point cloud using only information from the marked pixels, the pixel spacing (20 micron spacing), and the estimated optical depth distance as the z-coordinates.

To produce a smoother 3D representation, further 3D points are interpolated from the known 3D points in the point cloud using bilinear interpolation. Finally, a voxel reconstruction algorithm grids the 3D space into an even spacing of voxels at a known size, and by voting, each voxel is filled (or left empty) with a known color value which may come from various sources, such as the original imagery or any technical information, such as "texture" or melatonin. This allows for representation of the lesion in 3D with a smooth surface and for filling-in the internals of the lesion with the known color information from the imagery. Then, one can rotate, zoom, and even look inside the 3D lesion with the interpolated volume. Additionally, one may also (possibly) extrapolate 2D images at depths that the MelaFind system did not originally capture by back-projecting the 3D volume into the camera at various depths and interpolating the color values.

Optical Spectral Imaging can be presented to the user in a format via a computer user interface that allows user interaction and manipulation with any selected area of a 3-dimensional image in order to view and quantify targeted features. The user may select the area of interest and quantify information as generated by OSI. Different characteristics can be targeted by the user and a variety of outputs can be selected and manipulated. OSI assigns color codes to quantified algorithmic values as sourced from multispectral images in order to communicate to the user the level of disorganization or other features as imaged by multispectral imaging and transformed into OSI. The visual communication platform through the user interface allows the user to drive the operation and determine his/her area of interest in order to quantify such imaging information.

Users in different locations can share the OSI data and information. For example, the diagnostic imaging can be performed by a user at one location, while the acquired data can be analyzed by another user (or a machine of another user) at a different location.

First Example Implementation

Obtaining Multi-Spectral Images

The inventive system first obtains multi-spectral images. This can be achieved using the hardware and some of the software used with the MelaFind computer-controlled multi-spectral imaging and analysis system, in which ten distinct spectral bands are used to illuminate a skin lesion with wavelengths distributed over visible to near-infrared ranges, from 430 nm (blue) through 950 nm (near infrared spectrum). Appendix Image 1 illustrates the MelaFind optical scanner being held by a medical professional or technician against a region of interest on the back of a patient. Appendix Image 2 shows the wavelengths used to obtain data from various depths below the surface of the skin and examples of the images that can be created using the existing MelaFind system.

In use, the imaging assembly illuminates the skin with light through a thin layer of alcohol, via an illumination circuit containing light-emitting diodes (i.e. LED) composed to generate ten different wavelengths of light, turned on and off in rapid sequence under computer control. A Complementary Metal Oxide Semiconductor (CMOS) sensor inside the imaging assembly captures the set of ten images. Each of the ten images is labeled with its nominal wavelength of light. An automatically generated "segmentation mask" separates the lesion or other features of interest from the surrounding skin, the operation of which is further described below. The ten-image set is then sent for analysis to the on-board computer. One part of the computer's Operating Systems (OS) software automatically checks the image quality and alerts the user to retake images that are not satisfactory, which may be done as specified in U.S. Pat. Nos. 6,081,612 and 6,208,749.

Segmentation Mask Operation

The segmentation algorithm isolates the pixels in the images which belong to the lesion from those that do not (i.e., all background pixels). In practice, the "lesion" may not be a "lesion" in the medical sense, but for purposes of this invention may be considered any tissue or cell structure of interest that can be differentiated from the surrounding tissue based on characteristics such as blood volume saturation, oxygen saturation, or other characteristics that can be identified based on differential reflectance or absorption of light. The algorithm is a completely automated approach, requiring no user input to isolate the lesion. The segmentation is performed at each of the bands, one-by-one, to best capture the shape of the lesion (rather than only segmenting the top-most band and using that throughout the remaining bands, as was done in the existing MelaFind system). Alternatively, the tissue or cell structure of interest may be differentiated from the surrounding tissue based on characteristics such as blood volume saturation, oxygen saturation, or other characteristics that can be identified based on differential reflectance or absorption of light, as taught by, for example, PCT Application PCT/US11/64723 (filed Dec. 13, 2011), PCT Application PCT/US12/58065 (filed Sep. 28, 2012), PCT Application PCT/US13/71269 (filed Nov. 21, 2013), the contents of which are incorporated by reference in their entireties herein.

In the present system, in one embodiment best adapted to identifying lesions and tissue of interest that is generally centrally located in the images, it is assumed that the top-most ("band 0"), 430 nm image, has the best contrast to distinguish the lesion from the background. This is used to initialize all of the remaining images as follows: in the band-0 image, the system seeks to define a region-of-interest (ROI), defined as a rectangular bounding box, which best encompasses the lesion in the image. This allows for immediate disposal of a majority of the image, as this bounding box will suffice to initialize all other remaining images as the contrast decreases. Once the ROI is determined, the system performs an adaptive histogram thresholding in the remaining images within this ROI to associate each pixel as a foreground lesion pixel or as a background non-lesion pixel. More details on each follow below.

Initializing the Region-of-Interest on Band-0 for Segmentation

In order to find the ROI around the lesion in the first image, the system first performs an Expectation-Maximization (EM) unsupervised clustering of the pixels. Using the gray-scale values from the pixels, or other values determined based on the light absorbing or reflecting or other characteristics of the tissue of interest, all pixels in the entire image are collected into a single matrix dataset. The system then seeks to automatically divide these pixels into two groups: foreground and background, based only on the gray-scale or other values. The idea here is that lesion pixels are usually darker or have higher or lower values than background pixels, but defining what "dark", "higher", or "lower" means across all patients in a global sense is difficult, if not impossible. So instead, the system finds the best separation amongst the pixels on a per-patient basis. The EM algorithm is an iterative method for fitting a statistic model to a dataset by finding the maximum likelihood for the parameters of the statistic model. In this case, the system uses a Gaussian Mixture Model (GMM), seeking to maximize the parameters according to the mean, covariance, and mixture components to the dataset using the EM approach. The mean and covariance of each of the two groups represents the lesion-versus-non-lesion groups. In the end, this EM/GMM method allows the algorithm to assign a class-conditional probability at every pixel, meaning one can assign a probability of being in the lesion class as well as the probability of being in the non-lesion class, at every pixel. If the EM clustering works as designed, the probability at a lesion pixel will yield a higher probability in that group from the GMM than the non-lesion group.

If desired, the ROI can be further refined by attempting to eliminate spurious pixels in the image, which may be due to hairs or other tissue features that are not of interest, which can throw off the ROI estimate. To compensate for this, the system can add a prior probability model, such as a Gaussian weighting kernel, to the EM/GMM model which makes some assumption about the location or shape of the lesion. For example, a melanoma lesion would be roughly centered in the image. This does not need to be exact, and to achieve this prior model, the system constructs a Gaussian weighting function which weights pixels in the center of the image higher than those towards the edges of the image. This, along with the EM/GMM unsupervised clustering, allows the algorithm to select and divide pixels and eliminate those spurious detections towards the edges of the image. In practice, for the prior Gaussian model, the mean is set at the exact center of the image and the standard deviation is set as ⅛ of the image dimensions. Then, the system goes through the entire image, pixel-by-pixel, and computes the class-conditional probabilities of both classes, using both the EM/GMM model estimate and the prior Gaussian weighting kernel. Finally, using this information, the system automatically chooses which of the two classes is the lesion class by selecting that class which has the darker/lower mean value from the GMM estimate.

The system automatically selects a threshold on the final probabilities by constructing a histogram of the probabilities from the lesion class, accumulating a Cumulative Distribution Function (CDF), and then cutting off the threshold at 85% of the energy of the CDF. In the end, using the final probability values from the lesion class along with this automatically determined cutoff, the system can threshold the pixels and produce a bounding box or boxes for the ROI estimate to isolate the entire lesion or tissue of interest in the first image.

Applying the ROI Estimate to Segment all Remaining Images

Using the ROI from the first image, the system applies a well-known adaptive gray-thresholding algorithm called Otsu's Method. The ROI is important because the adaptive thresholding will not yield an optimal result if the entire image is considered; however, by just focusing on the lesion and a small region around it, the system is able to extract an optimal gray-level threshold using a histogram of the lesion within the ROI. The threshold then allows the system to assign a value of 255 to all lesion pixels and a value of 0 to all other pixels. The system does this separately at each band image because the gray-level threshold will change from band-to-band. However, the same ROI is used to extract the gray-level threshold from the Otsu algorithm, as this only needs to be a rough estimate around the lesion. The Otsu algorithm assumes that the histogram of pixels is bi-modal (meaning there are only two main classes amongst the pixels, which is true for the lesion/non-lesion assumption), and it calculates the optimal threshold separating these two classes so that their combined spread (intra-class variance) is minimal.

In the end, the system is able to segment all images from the imaging system and assign a binary value to each pixel to isolate the lesion pixels from the non-lesion pixels.

Additionally, the system employs a method to halt the segmentation where the algorithm deems the lesion is no longer visible. Because it is possible that some lesions don't exist deep enough to reach all 10 image depths, it is beneficial to ignore those images where the segmentation has yielded a result that suggests that the lesion is not visible. In this way, the 3D representation of the present invention more accurately represents the full shape of the lesion, without any additional non-lesion information. This is achieved as follows: each segmented image comprises a binary mask yielding which pixels belong to the lesion and which pixels do not belong to the lesion in that image. The system collects the 2D pixel locations (u,v) of all highlighted pixels in a given segmentation mask and computes a Shape feature descriptor using Image Moments. Image Moments are various kinds of weighted averages of an image's pixel intensities, or some function of these averages which is usually chosen to provide some invariance properties. The present system uses the well-known "Hu Invariants" (See http://ieeexplore.ieee.org/xpl/login.jsp?tp=&arnumber=1057692&url=http%3A%2F%2Fieeexplore.ieee.org%2Fxpls%2Fabs_all.jsp%3Farnumber%3D1057692). These yield a 7-element "descriptor", meaning a vector with 7 numbers, each of which uniquely describe the shape of the lesion on this particular segmentation mask. Beginning with the first image (image "0"), the system computes the Hu Moment as $H_0$. Then, the system computes every subsequent Hu Moment at the next image down in the depth dimension, according to the bandwidths, and calculates the Euclidean distance of each next Hu Moment to the previous Hu Moment. In this way, $H_0$ from image 0 is compared with $H_1$ from image 1, and a "shape distance" is computed. The system does this repetitively and pairwise, between $H_1$ and $H_2$, $H_2$ and $H_3$, and so on, for all ten images (i.e., between $H_8$ and $H_9$). If the Euclidean distance for any pairwise check is too large, defined by a Euclidean distance threshold that is empirically determined (e.g., 0.04), the system immediately stops and labels that image as the last valid image representing the lesion. The intuitive explanation for this is that the shape of the lesion, from image to image, should not change significantly. However, if the segmentation were to fail because the contrast of the lesion is too low, the shape will vary significantly and this will be captured by the Hu Moment shape distance checks of the present system. In this way, any further image is deemed to not show the lesion as visible and therefore is ignored. This allows the system to only consider those pixels which are likely to be a part of the lesion and not process the pixels which don't contain the lesion.

This technique can also optionally be used for the melanoma scoring system, as disclosed in U.S. Pat. No. 6,208,749) to improve the scoring accuracy. In that system, a single segmentation mask was used to score all pixels from all images within that mask. However, if the lesion doesn't penetrate deep enough to be contained within all 10 images, then inevitably some pixels will be included in the score which have nothing to do with the lesion, and those pixels will only serve as "noise" in the final score. With the approach of the present system, those pixels which are unlikely to be from the lesion can be ignored, thus reducing the noise in the computation to retrieve a more accurate melanoma score.

Reconstructing the Lesion into a Three Dimensional Image

After checking image quality and completing segmentation, the on board computer contains three sets of images of the skin lesion, which may be displayed as a three dimensional image to the user. Using the segmented lesion pixels, the system is able to construct a point cloud as follows: at every pixel which survives the segmentation algorithm, the system assigns an (x, y, z) point location in units of millimeters (mm). The imaging system is known to have a pixel size of, for example, 20×20 microns, and so the (x,y) location of any pixel (u,v) in any image is transformed to a metric location as follows:

x=u*0.02; // u is the horizontal pixel location, and x is in mm;

y=v*0.02; // v is the vertical pixel location, and y is in mm;

where 0.02 represents 20 microns in mm to transform any pixel to a mm unit. Finally, the z-component comes from the known depths that each bandwidth penetrates the tissue, as a planar representation. In the end, only the segmented lesion pixels are transformed to 3D using this transformation from pixels to mm.

The system defines "texture" or melatonin in images by convolving each gray-scale image with a pre-defined kernel that highlights spatial gradients in the image. A "convolution" is a mathematical operation on two functions (in the present case, the image is one function and the pre-defined kernel is the other function), producing a third function (in the present case, this would be the texture image). In image processing, convolving images with kernels typically highlights different characteristics of the image. In this case, the objective is to highlight where local spatial gradients are high, i.e., where nearby pixels in small square neighborhoods have very different values (referred to as high texture), conversely marking those areas with very similar values in small neighborhoods within the image having low texture. A convolution allows the system to estimate this with a single operation. The kernel, k, that the system uses to compute the texture image via convolution is a 3×3 matrix defined as follows:

k=[−2.0 1.0 −2.0;
1.0 8.0 1.0;
−2.0 1.0 −2.0]

To assign a color, the system knows the color from the original (u, v) used to create (x_k, y_k, z_k), so this can be looked up directly in the image. So, for example, referring to the original gray-scale image at level k as I_k, and the associated "texture" image as T_k, the system can assign a gray-scale color to (x_k, y_k, z_k) by taking the pixel value at I_k(v, u), and similarly, the system can retrieve the RGB color associated with the texture image T_k as T_k(v, u). Then, when the 3D point is rendered, the system can assign the appropriate color straight from the image.

It is further possible to "fill in" the 3D image of the present invention by interpolating data in planes between each of the 10 images measured at each different wavelength. Weighted averages of the data from adjacent measured images can be calculated to create an interpolated "image." The present invention achieves this via bilinear interpolation, where the key idea is to perform linear interpolation first in one direction and then again in the other direction. By interpolating a pixel from two different images at that same pixel location, bilinear interpolation allows the system to take a contribution from both images to produce the "interpolated" value. Linear interpolation, on the other hand, would be to use some weighted version of that pixel from only one image. The present system could use linear interpolation (as well as any other known method of interpolation), but bilinear interpolation produces more accurate results. For example, static depths can be assigned to each image according to the bandwidth (band 0=0.4 mm, band 1=0.7 mm, band 2=0.8 mm, band 3=0.9 mm, band 4=1.3 mm, band 5=1.7 mm, band 6=1.9 mm, band 7=2.0 mm, band 8=2.2 mm, and band 9=2.5 mm). Therefore, using bilinear interpolation, the system can interpolate any image at any depth using the two closest images from this original set of 10 images, according to their depths. Suppose the system wanted to interpolate an image at 0.5 mm. First, it would go through the list of 10 images listed above and find the two consecutive images with the closest depths, one above and one below the desired depth. This would yield the images at 0.4 mm (band 0) and 0.7 mm (band 1). The appropriate weights are then assigned to linearly interpolate first forward from 0.4 mm and then backwards from 0.7 mm, and this is done simultaneously. More specifically, given a desired depth, the depths of the two closest consecutive images, $I_0$ and $I_1$, are found from the original set of 10, as d0 and d1. The system then computes weights on these images as:

$$w0=1.0-((desiredDepth-d0)/(d1-d0))$$

$$w1=1.0-((d1-desiredDepth)/(d1-d0))$$

These weights then determine how to weight the pixel values from each pixel in $I_0$ and $I_1$ in the interpolated image, referred to as $I_{int}$. For example, considering any given pixel (u, v), the system computes:

$$I_{int}(u,v)=w0*I_0(u,v)+w1*I_1(u,v)$$

Examples of the 3D images thereby produced are illustrated in the Images in the Appendix, starting with Image 3. The 3D images, once created, can be rotated in space in the Lesion Renderer embodiment of the present invention. Rotation and other image manipulation is enabled by using programming techniques well known in the art for manipulating computer-rendered 3D images. The 3D images can also be "sliced" to show interior portions from left to right, from right to left, and from top to bottom, using programming techniques known in the art. In the Lesion Renderer used with this embodiment of the present invention, this "slicing" is accomplished by sliding the bars on the left hand side of the Renderer, as shown in Image 3.

Image 3 shows a multispectral gray-scale image of a lesion created by the present inventive system. The 3D image was created by using 2D images taken at successive layers, up to 2.5 mm deep into the skin below the lesion, as described above. The gray-scale tone of each pixel corresponds to a "texture" or other parameter calculated for each pixel, which may be calculated according to the method described in U.S. Pat. Nos. 6,081,612 and 6,208,749 or as described elsewhere herein. As the pixels get darker, the imaged tissue is more disorganized. A 3D gray-scale image with the right side of the lesion removed to show the interior of the lesion, as is possible using the system of the present invention, is shown in Image 4. A zoomed-in 3D gray-scale image is shown in Image 5. A 3D gray-scale image with the top of the lesion removed is shown in Image 6.

It is also possible to render images of the lesion using pseudo-colored representations of features. Image 7 shows a 3D image of a lesion colorized according to "texture." Image 8 shows the same lesion with the top "sliced" off to show the interior. For areas of homogeneity, the algorithm colors the location with cool colors. For areas of high disorganization, the algorithm colors them with warm colors.

The images may be rendered in gray-scale or false color to reflect any of the parameters described in U.S. Pat. Nos. 6,081,612 and 6,208,749, and as set forth herein. For example, the images could be rendered in grayscale or color according to the amount of asymmetry of the lesion. This asymmetry calculation works by first finding the major axis of the lesion. The algorithm then folds the lesion in half along that imaginary line and measures and displays a difference of the two halves. In areas where there is significant asymmetry, it colors the area with warm colors like reds, oranges, and yellows. For areas showing little to no asymmetry, the feature colors the location with cool colors like blues, greens, or black.

Likewise, the grayscale or false color may be applied using parameters determined by direct comparison with lesions previously labeled by experienced medical professionals. By cycling through every possible texture value, texture values can be correlated with clinical observations regarding the depth of cell disorganization, and optimal threshold levels for rendering texture can be determined.

Image 9 shows a 3D image of a lesion where the threshold for showing "texture" has been adjusted. An RGB color is assigned to each 3D point according to the value of the real-valued texture at that 3D point, which is retrieved from the appropriate image. Blue signifies a very high texture, and red signifies a very low texture. All other points are scaled evenly in between blue and red towards green. The slider bar, as shown in Image 9, adjusts a threshold that is used to "hide" or "show" points based on the value of their texture. In other words, each position of the slider bar specifies some threshold on the texture values. For a given value, all 3D points that are larger than that texture threshold value are hidden, while all 3D points that are smaller or equal to that threshold value are shown. By adjusting the threshold with the slider bar, one can observe how the 3D points are distributed based on their texture values. As shown in Image 9, a very low fixed background level of grey color is applied so that the viewer can see in ghostly form the outlines of the entire lesion, so that the areas of high disorganization are seen "floating" inside the lesion. In this way, those 3D points which do not conform to the given texture threshold value from the slider bar are drawn with a lower alpha value, and are much more transparent. This is done so one can observe where the highlighted 3D points are located relative to the rest of the lesion, using different levels of transparency.

The 3D lesion imaging system of the present invention can also be used to image tissue that has been removed from a patient. The removed tissue may be fixed in some material like paraffin, for example, before it is imaged. Similarly, a viewer may also prepare a 3D image of a lesion using the imager of the present invention and then use the 3D image while directly examining the lesion. By viewing the tissue directly under a microscope, while also referring to a previously prepared 3D image of the lesion, it is possible to improve analysis and diagnosis of lesions.

Image 10 shows the operation of the measuring mode in the Lesion Renderer embodiment of the present invention. The distance between the two red dots shown on the lesion is 1.19651 mm, as displayed in the upper left hand of the Lesion Renderer image. Alternatively, the measuring mode can switch to a 2D point cloud to ensure consistent dimensionality for depth measurement.

OpengGL Rendering

Another embodiment of the 3D lesion visualization application is described below in subsections A, B, C and D. For example, the prior art MelaFind system extracts lesion appearance in gray scale images at 10 different depths beneath the skin surface. One can convert this information to other textures for better understanding of shape and intensity variations using RGB coloring. Thus, to display a single layer of lesion with size 1024×1280, one needs total 1310720 vertices, and texture color for each vertex. The memory requirement to store this information would be (1310720×3 (vertex, XYZ)+1310720×3 (texture, RGB)) units.

As opengl doesn't store the state of vertices and texture, the complete information is required to be transferred to an opengl context on every small change in the display angles. This operation with such a high volume of information results in a high turnaround time leading to a considerable lag while moving point cloud. One of the options to reduce the data transfer time could be to store vertices and textures in the GPU buffer (VBOs or VAOs), and get shaders to load this information to the opengl context. This option fails due to the limitation on the graphic card memory for the Surface Pro 3.

As all the pixels in a single layer of lesion image are assumed to be at same depth and at relative position w.r.t the other pixels, depth (z, same for all pixels in an image), X and Y position is known for each pixel. This assumption can be used to reduce the number of vertices to 4, independent of the image size. It also makes feasible to store the texture (color for all the pixels) on the GPU buffer. Once the texture information is transferred to the buffer, opengl could refer this information with faster turnaround time resulting in a smooth movements of point cloud. Following sections explain the step by step procedure to achieve the proposed method.

Preferably, the 3D visualization system for lesion supporting grayscale, RGB and irregular (non rectangular) objects rendering. The proposed method is being adapted to handle all the requirements. Following topics explain procedures with code snippets to achieve every requirement.

A. Transferring Textures to the GPU Buffer:

This is done only once for an image in the opengl context—not every display call. When not required, it is cleared from the memory. At one time one needs to load texture for every layer in a lesion, including the interpolated layers.

Every texture in the opengl context is identified by a unique id (interger). First a request is made to the opengl context to generate the required number of texture ids. A custom integer could also be used, but there are chances of it colliding with a reserved number.

```
GLuint tex; glGenTextures(1, &tex); // for one texture
OR
GLuint *tex; tex = new GLuint[n]; glGenTextures(n, tex);//for n number of texture ids
```

Now for each texture load an image, for this purpose GLEW is used. GLEW is a very light utility around the glut, it is used specifically for loading images to textures. As the MelaFind vision system is using opencv Mat for storing image information, a code snippet is written to transfer Mat information to the GPU buffer (texture mapping). Every line in the code snippet is explained with comments:

Select the texture id

First, select the texture id for which the given image should be transferred to the buffer or binding an image to texture id.

glBindTexture(GL_TEXTURE_2D, textureID);

Since the number of pixels in original image is resolution independent, they won't always match pixels while displaying. This happens when a texture image is stretched beyond its original size (more number of vertices) or when it's sized down. OpenGL offers various methods to decide on the sampled color when this happens.

```
glTexParameteri(GL_TEXTURE_2D, GL_TEXTURE_MIN_FILTER, GL_LINEAR); //set to linear interpolation
glTexParameteri(GL_TEXTURE_2D, GL_TEXTURE_MAG_FILTER, GL_LINEAR); //set to linear interpolation
```

When a texture needs to be applied to a surface with more number of vertices than the number of pixels in the original image, interpolation should be avoided. There could be multiple option to handle such case. The options are GL_REPEAT, GL_MIRRORED_REPEAT, GL_CLAMP_TO_EDGE and GL_CLAMP_TO_BORDER. This functionality is not being used in this embodiment of the lesion rendering system, but it could be.

```
glTexParameteri(GL_TEXTURE_2D, GL_TEXTURE_WRAP_S, wrap_Filter);
glTexParameteri(GL_TEXTURE_2D, GL_TEXTURE_WRAP_T, wrap_Filter);
```

Now, calling a glew routine to load the mat information in the referenced texture,

```
glTexImage2D(GL_TEXTURE_2D,  // Type of texture
    0,   // Pyramid level (for mip-mapping) - not useful in the system
    GL_RGBA,  //Internal colour format to convert to
    image_height,  // number of rows in an image
    image_width,   // Image height i.e. 480 for Kinect in standard mode
    0,   // Border width in pixels (can either be 1 or 0)
    input_Colour_Format,  // Input image format (i.e. GRAY, RGB and RGBA .)
    GL_UNSIGNED_BYTE,  // Image data type
    mat.ptr( ));  // The actual image data itself
```

These steps would bind an image with a texture id in the opengl context.

In order to clear the buffers when not required or new set of textures needs to be loaded,

```
GLuint tex; glDeleteTextures(1, &tex); //for one texture
GLuint *tex; tex = new GLuint[n]; glDeleteTextures(n, tex); //for a number of texture ids
```

B. Displaying a Complete Image Using 4 Vertices:

Every 2D texture in the opengl context is mapped in the a unit coordinate system, where 4 corners are mapped to (0,0), (0,1), (1,0) and (1,1). This coordinate system can be used to extract a specific part of a loaded texture, be it a point, line, triangle, square or polygon in general. FIG. 11 visually shows mapping of a triangular texture to a 3D plane.

This could be achieved using a simple code snippet,

```
glEnable(GL_TEXTURE_2D);
    glBindTexture(GL_TEXTURE_2D, texture_id); //the texture want to use, it should
    already be loaded
    glBegin(GL_TRIANGLES);
        glTexCoord2f(0.0, 0.0); glVertex3f(0.0, 0.0, 0.0);
        glTexCoord2f(0.0, 1.0); glVertex3f(0.0, 1.0, 0.0);
        glTexCoord2f(1.0, 1.0); glVertex3f(1.0, 1.0, 1.0);
    glEnd( );
glDisable(GL_TEXTURE_2D);
```

As explained earlier, the pixels in an image are at same depth (Z) and having a relative position (X and Y), use of Square (Quad) reduces the number of vertices required to describe image pixels to vertices mapping. We could have a complete texture mapped to a horizontal plane (having fixed width w and height h) placed at a predefined value (depth, z) on the Z axis and around the origin. This can be done using the following code

```
glEnable(GL_TEXTURE_2D);
    glBindTexture(GL_TEXTURE_2D, texture_id);
    glBegin(GL_QUADS);
        glTexCoord2f(1.0f, 1.0f); glVertex3f(-w/2, h/2, z);
        glTexCoord2f(0.0f, 1.0f); glVertex3f(w/2, h/2, z);
        glTexCoord2f(0.0f, 0.0); glVertex3f(0.0f, 0.0f); glVertex3f( w/2, h/2, z);
        glTexCoord2f(1.0f, 0.0f); glVertex3f(-w/2, -h/2, z);
    glEnd( );
glDisable(GL_TEXTURE_2D);
```

This is done for all the layers in a lesion by changing the texture_id and replacing z with a desired depth to display complete lesion point cloud in 3D as shown in FIGS. 12A and 12B. If the area of plane (in pixels) is bigger than the actual number of pixels in the mapped texture, the defined magnification filter would be applied by opengl before display.

C. Displaying an Image with Cutoff:

In the lesion explorer, one needs a way to observe the variance of an intermediate pixel (at a specific width and height) in a lesion. This is selected by user using the sliders in the User Interface ("UI") as shown in FIGS. 13A (full size lesion rendering) and 13B (partial lesion rendering).

Complete image display using method explained till now is not essential for this functionality (as shown in FIG. 13A). To handle this case partial texture mapping is done based on the user selected cutoffs (as shown in FIG. 13B). The cutoffs are restricted between 0 and 1. Total 3 cutoffs are used for each axis, X, Y and z axes mapped to width, height and depth respectively. The partial texture mapping is done using the following code snippet.

```
if z is within the z_cutoff
    glEnable(GL_TEXTURE_2D);
        glBindTexture(GL_TEXTURE_2D, texture_id);
        glBegin(GL_QUADS);
            glTexCoord2f(1.0f, 1.0f - y_cutoff); glVertex3f( -w/2, h/2- h * y_cutoff, z);
            glTexCoord2f(0.0f + x_cutoff, 1.0f - y_cutoff); glVertex3f(w/2 - w * x_cutoff,
            h/2 - h * y_cutoff, z);
            glTexCoord2f(0.0f + x_cutoff, 0.0); glVertex3f( w/2 - w * x_cutoff, -h/2, z);
            glTexCoord2f(1.0f, 0.0f);
            glVertex3f(-w/2, -h/2, z);
```

```
glEnd( );
glDisable(GL_TEXTURE_2D);
```

D. Displaying an Irregular Object:

Approaches explained till now are enough for displaying lesion images in full and partial sizes. However, it can only display multiple rectangular textures with specific height and width placed at specific depths in 3D. Generally lesions are of irregular shape as shown in the images below.

It is stored in a normal rectangular image holder (Mat in opencv), black are in the FIG. 14 is background. An additional binary image (FIG. 15) is used to define the foreground (lesion) pixels within a segmented lesion image. The size (width and height in pixels) is same of both the images. The pixels with binary value 1 are part of lesion, the pixels with binary value 0 belong to the background.

To display only the lesion pixels, one of the approach could be to look up the binded texture buffer for all pixels one by one.

```
glBegin(GL_POINTS);
    if a point is part of lesion
        glTexCoord3f(R, G, B); glVertex3f( X, Y, Z);
glEnd( );
```

The color (R, G and B) for every pixel could be extracted from a texture buffer by querying at a coordinate. The coordinate for a point is found by normalizing the width and height between 0 and 1, and rounding off the number to the nearest whole number.

The approach has a limitation as lookup is done for every pixel. In this approach it is not useful to load textures in the GPU buffer, as each pixel is read again in the code and sent to the opengl context. The resolution might also be very low. So, one possibility is to do look up from the original image, which may lead to a large turnaround time in displaying a full size point cloud.

Another solution is to do pixel filtration on the fragment shader. The fragment shader could be customized to skip the pixels not part of the foreground. As the opengl supports RGBA rendering, the alpha channel shader is directly used to achieve filtration.

A rectangular lesion image is first converted to the RGBA format by attaching the binary image as an alpha channel. For a gray scale image (single channel image), present channel is repeated three times and the binary image is added as the fourth channel. For a colored (RGB) image, the binary image is added as the fourth channel. The RGBA images for all the layers are loaded in the opengl buffer and displayed using same techniques explained above. The only required change is enabling ALPHA_TEST as shown below,
glEnable(GL_ALPHA_TEST); glAlphaFunc(GL_GREATER, 0.0f);

This forces the fragment shader to avoid the background. Thus, an irregular shaped lesion could be displayed in opengl with a shorter turnaround time, as shown in FIG. 16.

Exposure Times for Obtaining Images

Exposure times and values are calculated during the imaging process. After the main control loop receives the trigger event (i.e. the user presses a triggering mechanism that starts the imaging process), the operating system (OS) goes through the following steps to capture eleven high resolution images and send the images to the host computer:

1. Capture a low resolution image (320×256×8-bit) at 430 nm (band 0).
2. Estimate the nominal exposure times for all the bands using the low resolution image.

A "skin_type_adjuster" is calculated to compensate for band-to-band differences that depend on skin type, as determined experimentally:

skin_type_adjuster=(−0.007×blue_band_LED-current× MAXIMUM_AVG/preview-average+1.245)×100/(100+ band_index) where preview-average is the intensity average of the low resolution image (320×256×8-bit).

MAXIMUM_AVG=60, which is the maximum 8-bit intensity average.

3. Optional use of high dynamic range imaging to produce segmentations that are independent of skin pigment:

High dynamic range (HDR) images allow for more than 8 bits per imaging channel to widen the span of the visual dynamic range that an image can capture simultaneously. In one aspect of the present inventive system, HDR can be achieved by first computing the camera's response function (possibly separately for each wavelength, or possibly for all wavelengths taken together). This works by collecting a series of images from the camera, each at different exposure times. A minimum of 3 images is required; however, more images (and at more exposures) will yield a better HDR solution. Using the images and associated exposure times, the camera response is estimated using a known method (See http://www.pauldebevec.com/Research/HDR/debevec-siggraph97.pdf). Then the camera response and a known weighting scheme is used to combine the images into a single HDR image, where each pixel contains values with a 32-bit range (rather than an 8-bit range), capturing a wider range of lighting conditions. Optionally, the 32-bit HDR image can then be mapped back into an 8-bit image which retains the properties of the HDR range using a process called tone-mapping. For this, a bilateral filter with a gamma correction allows for mapping back into a more visible 8-bit imaging range.

Other Example Implementations (1) Providing output that identifies for the pathologist where in the tissue the biopsy slice should be taken, based on the 3D representation of the tissue or of metrics associated with the tissue. The 3D representation can show the pathologist the concentration of malignancy texture (or cellular disorganization), based on which the pathologist can take the slices more precisely than with a collection of 2D images. The 3D rendering can be color-coded at each 3D location with information from the 2D texture images so that the pathologist can visually correlate low and high texture areas geometrically within the 3D representation of the lesion.

(2) Tele-dermatology—allowing for remote consultation, so that the technician operating the optical scanner on the patient is remotely located from the physician, surgeon, or dermapathologist who is viewing and manipulating the 3D image created by the system of the present invention. The remote medical professional can then instruct the technician, for example, on where and how to operate the scanner and where to biopsy the patient's skin or tissue.

(3) Providing volume metrics output that identifies for the dermatologist how deep and vast suspected tissue has penetrated into the skin—based on the 3D representation of the tissue or of metrics associated with the tissue. The 3D representation can show the dermatologist the volume and depth penetration of malignant texture (or cellular disorganization), which can aid the dermatologist with diagnosis more accurately than if the diagnosis was based solely on a collection of 2D images. In addition, the system can calculate a total value for any feature or characteristic identified, such as average or total texture disorganization within a lesion.

(4) Providing surface characteristics and volume metrics output that identifies for the surgeon the topographical area with a field of depth (e.g. topical height variations along with width and length of a designated area of the skin's tissue to be excised)—based on the 3D representation of the tissue or of volume based metrics associated with the tissue. The 3D representation can show the surgeon the volume and depth penetration of malignancy texture (or cellular disorganization), based on which the surgeon can excise more precisely than excision based solely on a collection of 2D images.

(5) Providing metrology—using the 3D representation, the pathologist can select various points on the model and measure the distances between these points precisely. Furthermore, using the interpolated volume, the pathologist can zoom to sub-surface data and observe and measure on sub-surface tissue.

(6) Using the texture image representation, the pathologist can define a cutoff value to identify an area-of-interest, specifying suspicious locations of tissue either on the surface and/or the interior of the lesion. The system can automatically extract these regions of interest and highlight them to easily signify the regions of the lesion to address.

(7) The system can be extended to capture a stream of images at each wavelength over time to produce a 3D video rather than a single set of 3D images. This would allow for a live intervention either directly or remotely, where tools may be tracked and viewed with respect to the lesion in 3D, to further assist in excising tissue and identifying only the portion desired to be removed. This live interaction can be incorporated into the 3D rendering system, showing temporal dynamically changing information during the intervention.

(8) Similar to the classifier mentioned previously which works on the 2D images, 3D geometric analysis can be incorporated to assess correlations between melanoma and non-melanoma lesions.

Possible Other Implementations Other than on Skin Tissue

The system can be used to monitor how wounds heal over time.

If used intra-operatively, the system can be used for monitoring tumors beneath the surface of organs, which would eliminate the need for expensive CT/MRI scans which are difficult or impossible to use intra-operatively. This would allow for better situational awareness during a biopsy or during removal of cancerous tissue.

Often during emergency situations, ER physicians are trying to locate the source of a bleed which is internal and difficult to isolate. Being able to scan to sub-surface levels of the body can help to more quickly isolate the source of bleeds in such and other emergency situations.

Cochlear applications. The small structures of the ear, internally and externally, can be visualized.

Pathology imaging of biopsy samples. When applied to an in-vitro sample such as paraffin, OSI can be used to determine the location of sectioning the tissue in order to ensure the most disorganized tissue is reviewed by the pathologist under the microscope. The technique can also be applied to understand how much of the lesion has been discarded by imaging both sides of a paraffin sample after sectioning, thus evaluating the performance of the grosser. Similarly, the imaging can be used to determine how far into the paraffin the current lesion has been sectioned.

Surgery biopsy and tissue related image guidance. The imaging of the present invention may be used either as a live video feed or through images in order to guide surgeons and physician in excisions by determining features such as lesion volume and area of disorganization. In addition, the ability to image surrounding tissue allows the physician to determine a baseline of tissue features, thus utilizing imaging to guide margins when visually unattainable.

Ex vivo imaging of tissue. A 3D image sample of a lesion may be obtained after it has been excised from the body to help grossers image the portion of the lesion for sectioning prior to setting the lesion in paraffin.

Determining margins for surgery, both pre and post excision. A 3D image may be used to visualize any selected remaining tissue "left behind" after surgery or may be used for surgery planning to identify margin for excision.

Other applications may be in guiding surgeons and interventionists in the evaluation of other tissue constructs other than potentially cancerous lesions. Interventional cardiologists may benefit from examining vessel wall tissue organization as well as myocardial wall cell construct. General surgeons may benefit from using the inventive technology to examine tissue in exploratory procedures. Plastic and Aesthetic physicians may use the images created to evaluate skin properties before and after aesthetic procedures. Digital visualization of tissue vascularity, construct of fibrin and collagen, angiogenesis, hair follicles, depth of wrinkles, and other dermal features may assist in documentation of wrinkles and enable measurement of treatment outcomes.

The description of certain embodiments of this invention is intended to be illustrative and not limiting. Therefore, although the present invention has been described in relation to particular embodiments thereof, many other variations and other uses will be apparent to those skilled in the art. It is understood therefore that the present invention is not limited by the specific disclosure herein, but only by the broadest scope of the appended claims. Possible and known variations for the systems and methods described herein can be implemented in a number of different ways as long as the operation of the inventive system and method falls within the appended claims.

The invention claimed is:

1. A method of non-destructive imaging of an anomalous tissue in a region of interest, the method comprising:
   a) illuminating the region of interest with light in multiple spectral bands, each of the spectral bands being associated with a respective predetermined depth value in the tissue;
   b) capturing, with a camera, a two-dimensional image of the region of interest under illumination by the light in each of the spectral bands;
   c) identifying a first anomaly area containing the anomalous tissue within the image of a topmost spectral band;
   d) applying the first anomaly area to each of the images of the spectral bands that are deeper than the topmost;
   e) segmenting each of the images of the deeper spectral bands, one by one, wherein the segmenting automatically identifies pixels belonging to the anomalous tissue, isolating a shape of the anomalous tissue;
f) halting the segmentation of the images of the deeper spectral bands when the anomalous tissue is no longer detected;
g) determining a set of data points for each of the segmented images, wherein each set of data points has lateral position data defining a position within a respective spectral plane at a respective depth value;
h) transforming each set of data points for each segmented image into a single three-dimensional anomaly volume by additionally applying the predetermined depth value to each of the respective set of data points for each segmented image, yielding transformed sets of data points, respectively, each data point within each of the transformed sets of data points thereby assigning lateral position and depth data values;
i) rendering an image of the three-dimensional anomaly volume by plotting the transformed sets of data points; and
j) displaying the rendered image to a user.

2. The method of claim 1, wherein the segmentation comprises segmenting the image of the deeper spectral bands into a binary image.

3. The method of claim 1, wherein the camera includes optical components and a sensor.

4. The method of claim 3, wherein of each of the predetermined depth values is based on the respective spectral band of light and optical calibration of the camera.

5. The method of claim 3, wherein the sensor is a complementary metal oxide semiconductor-type sensor.

6. The method of claim 1, wherein the multiple spectral bands of light are provided by one or more light-emitting diodes.

7. The method of claim 1, further comprising rendering texture within the image of the three-dimensional anomaly volume by additionally processing at least one of the spectral band anomaly areas with a pre-defined computation, in order to illustrate differences in spatial gradient.

8. The method of claim 1, wherein:
the topmost spectral band is a wavelength of light of about 430 nm and the first depth value is about 0.4 mm.

9. The method of claim 1 wherein identifying the region of interest comprises the following steps:
performing an Expectation Maximization (EM) and Gaussian Mixture Model (GMM) clustering of the pixels;
automatically dividing all of the pixels into the anomalous tissue or a background and assigning a conditional probability at every pixel for being in an anomalous tissue class or a non-anomalous tissue class;
selecting a threshold on a final probability;
accumulating a Cumulative Distribution Function; and
cutting off the threshold to produce a bounding box for the anomalous tissue.

10. The method of claim 9 further comprising adding a Gaussian weighting kernel to the EM/GMM model to eliminate spurious pixels.

11. A system for non-destructive imaging of an anomalous tissue in a region of interest, comprising:
a) a source of illumination of light in multiple spectral bands;
b) a camera for acquiring digital images of the region of interest based on the light re-emitted from the region of interest when illuminated at multiple each of the at least two spectral bands, the digital image comprising digital signals whose values are a function of a condition of the region of interest;
c) a memory for storing the digital images;
d) a digital processor adapted and configured for
 i) processing the digital image of a topmost spectral band stored in memory and computing an estimated value of parameters which are a function of the processed topmost image to define a first anomaly area;
 ii) processing and applying the first anomaly area to each of the deeper spectral band images;
 iii) segmenting each of the images of the deeper spectral bands, one by one, wherein the segmenting automatically identifies pixels belonging to the anomalous tissue, isolating a shape of the anomalous tissue;
 iv) halting the segmentation of the images of the deeper spectral bands when the anomalous tissue is no longer detected;
 v) determining a set of data points for each of the segmented images, wherein each set of data points has lateral position data defining a position within a respective spectral plane at a respective depth value;
 vi) transforming the each set of data points for each segmented image into a single three-dimensional anomaly volume; and
 vii) rendering an image of the three-dimensional anomaly; and
e) a display adapted and configured for displaying the rendered image to a user.

12. A non-transitory computer-readable storage medium comprising a plurality of instructions configured to execute on at least one computer processor to enable the computer processor to:
a) initiate illumination of a region of interest with light in multiple spectral bands, each of the spectral bands being associated with a respective predetermined depth value in the tissue;
b) initiate capture, with a camera, a two-dimensional image of the region of interest under illumination by the light in each of the spectral bands;
c) identify a first anomaly area containing the anomalous tissue within the image of a topmost spectral band;
d) apply the first anomaly area to each of the images of the spectral bands that are deeper than the topmost;
e) segment each of the images of the deeper spectral bands, one by one, wherein the segmenting automatically identifies pixels belonging to the anomalous tissue, isolating a shape of the anomalous tissue;
f) halt the segmentation of the images of the deeper spectral bands where the anomalous tissue is no longer detected;
g) determine a set of data points for each of the segmented images, wherein each set of data points has lateral position data defining a position within a respective spectral plane at a respective depth value;
h) transform each set of data points for each segmented image into a single three-dimensional anomaly volume by additionally applying the predetermined depth value to each of the respective setoff data points for each segmented image, yielding transformed sets of data points, respectively, each data point within each of the transformed sets of data points thereby assigning lateral position and depth data values;

i) render an image of the three-dimensional anomaly volume by plotting the transformed sets of data points; and
j) display the rendered image to a user.

* * * * *